(12) United States Patent
Keller et al.

(10) Patent No.: US 11,364,268 B2
(45) Date of Patent: Jun. 21, 2022

(54) **INACTIVATED *BACILLUS COAGULANS* AND USES THEREOF FOR INCREASING PHYSICAL PERFORMANCE**

(71) Applicant: Ganeden Biotech, Inc., Mayfield Heights, OH (US)

(72) Inventors: David Keller, Beachwood, OH (US); Howard Allen Cash, Mentor, OH (US); Sean Farmer, North Miami Beach, FL (US)

(73) Assignee: Ganeden Biotech, Inc., Mayfield Heights, OH (US)

(*) Notice: Subject to any disclaimer, the term of this patent is extended or adjusted under 35 U.S.C. 154(b) by 24 days.

(21) Appl. No.: 16/625,661

(22) PCT Filed: Jun. 21, 2018

(86) PCT No.: PCT/US2018/038751
§ 371 (c)(1),
(2) Date: Dec. 20, 2019

(87) PCT Pub. No.: WO2018/237143
PCT Pub. Date: Dec. 27, 2018

(65) Prior Publication Data
US 2021/0154242 A1    May 27, 2021

Related U.S. Application Data

(60) Provisional application No. 62/522,817, filed on Jun. 21, 2017.

(51) Int. Cl.
*A61K 35/74* (2015.01)
*A23L 33/135* (2016.01)

(52) U.S. Cl.
CPC ............ *A61K 35/74* (2013.01); *A23L 33/135* (2016.08)

(58) Field of Classification Search
None
See application file for complete search history.

(56) References Cited

U.S. PATENT DOCUMENTS

| | | |
|---|---|---|
| 2011/0027348 A1 | 2/2011 | Feher |
| 2012/0251512 A1 | 10/2012 | Farmer et al. |
| 2016/0074495 A1* | 3/2016 | Farmer .............. A61P 37/04 424/246.1 |
| 2017/0000872 A1 | 1/2017 | Farmer et al. |

FOREIGN PATENT DOCUMENTS

WO    WO-2015017625 A1 *  2/2015  ............ A23L 33/10

OTHER PUBLICATIONS

Guglielmetti et al., "A Dairy Bacterium Displays in Vitro Probiotic Properties for the Pharyngeal Mucosa by Antagonizing Group A Streptococci and Modulating the Immune Response," Infection and Immunity, 78:11 pp. 4734-4743, 2010.
Bouhy, et al., "Delayed GM-CSF Treatment Stimulates Axonal Regeneration and Functional Recovery in Paraplegic Rats via an Increased BDNF Expression by Endogenous Macrophages," The FASEB Journal, vol. 10, pp. 1239-1241, 2006.
The International Search Report and the Written Opinion from Corresponding International Application No. PCT/US2018/038751 dated Sep. 7, 2018.

* cited by examiner

*Primary Examiner* — Brian Gangle
(74) *Attorney, Agent, or Firm* — Sughrue Mion, PLLC

(57) ABSTRACT

The present subject matter provides, inter alia, compositions and methods comprising inactivated, non-viable, or dead *Bacillus coagulans* bacteria such as whole dead bacterial spores and/or cells and/or particles that comprise inactivated, non-viable, or dead *Bacillus coagulans* bacteria. Compositions and methods comprising *Bacillus coagulans* peptidoglycan and/or lipoteichoic acid are also provided.

23 Claims, 20 Drawing Sheets
Specification includes a Sequence Listing.

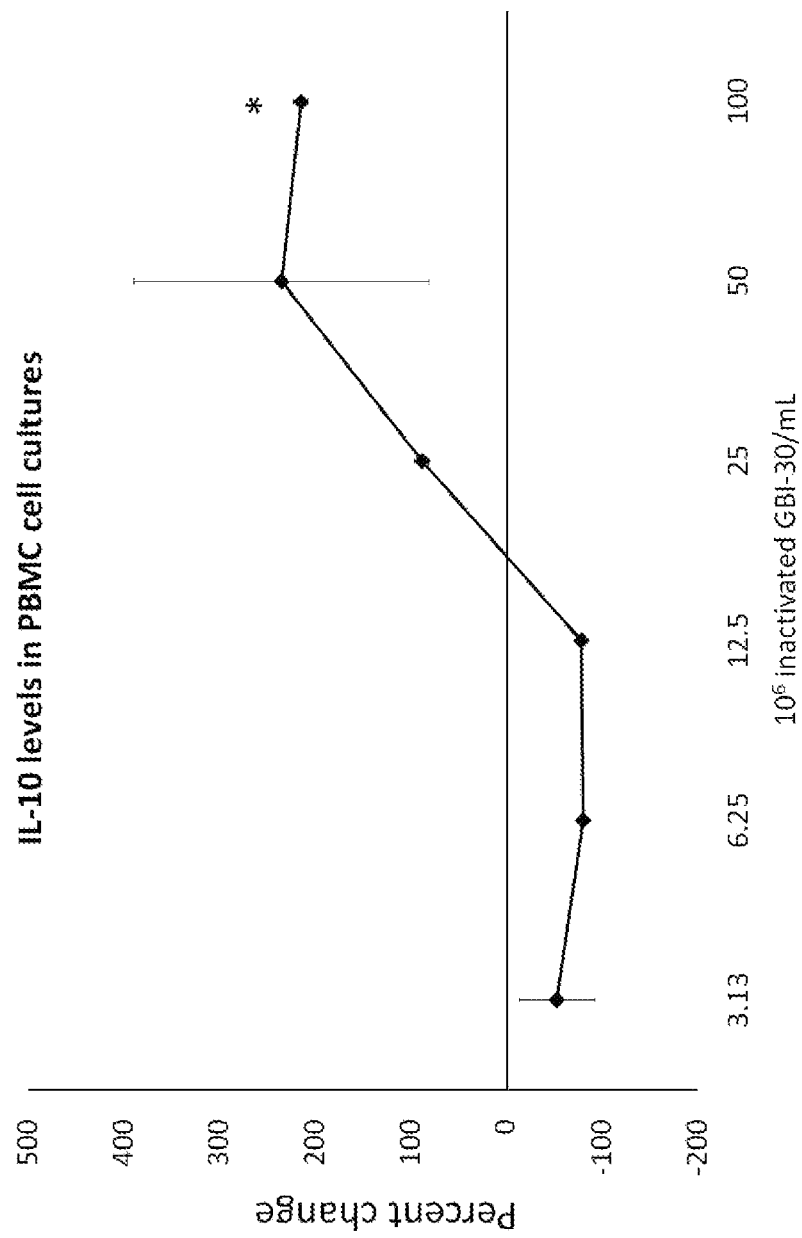

SEQUENCE LISTING

```
<160> NUMBER OF SEQ ID NOS: 49

<210> SEQ ID NO 1
<211> LENGTH: 207
<212> TYPE: PRT
<213> ORGANISM: Homo sapiens

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95
```

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
            115                 120                 125

Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 2
<211> LENGTH: 168
<212> TYPE: PRT
<213> ORGANISM: Homo sapiens

<400> SEQUENCE: 2

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Ala Gly Cys Leu Ser Gln Leu His Ser Gly Leu Phe Leu Tyr Gln
65                  70                  75                  80

Gly Leu Leu Gln Ala Leu Glu Gly Ile Ser Pro Glu Leu Gly Pro Thr
                85                  90                  95

Leu Asp Thr Leu Gln Leu Asp Val Ala Asp Phe Ala Thr Thr Ile Trp
            100                 105                 110

Gln Gln Met Glu Glu Leu Gly Met Ala Pro Ala Leu Gln Pro Thr Gln
        115                 120                 125

Gly Ala Met Pro Ala Phe Ala Ser Ala Phe Gln Arg Arg Ala Gly Gly
    130                 135                 140

Val Leu Val Ala Ser His Leu Gln Ser Phe Leu Glu Val Ser Tyr Arg
145                 150                 155                 160

Val Leu Arg His Leu Ala Gln Pro
                165

<210> SEQ ID NO 3
<211> LENGTH: 204
<212> TYPE: PRT
<213> ORGANISM: Homo sapiens

<400> SEQUENCE: 3

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

```
Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
                115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
                195                 200

<210> SEQ ID NO 4
<211> LENGTH: 171
<212> TYPE: PRT
<213> ORGANISM: Homo sapiens

<400> SEQUENCE: 4

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
                35                  40                  45

Glu Gln Val Arg Lys Ile Gln Gly Asp Gly Ala Ala Leu Gln Glu Lys
    50                  55                  60

Leu Val Ser Glu Ala Gly Cys Leu Ser Gln Leu His Ser Gly Leu Phe
65                  70                  75                  80

Leu Tyr Gln Gly Leu Leu Gln Ala Leu Glu Gly Ile Ser Pro Glu Leu
                85                  90                  95

Gly Pro Thr Leu Asp Thr Leu Gln Leu Asp Val Ala Asp Phe Ala Thr
                100                 105                 110

Thr Ile Trp Gln Gln Met Glu Glu Leu Gly Met Ala Pro Ala Leu Gln
                115                 120                 125

Pro Thr Gln Gly Ala Met Pro Ala Phe Ala Ser Ala Phe Gln Arg Arg
    130                 135                 140

Ala Gly Gly Val Leu Val Ala Ser His Leu Gln Ser Phe Leu Glu Val
145                 150                 155                 160

Ser Tyr Arg Val Leu Arg His Leu Ala Gln Pro
                165                 170

<210> SEQ ID NO 5
<211> LENGTH: 207
<212> TYPE: PRT
<213> ORGANISM: Homo sapiens

<400> SEQUENCE: 5
```

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
            115                 120                 125

Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
            195                 200                 205

<210> SEQ ID NO 6
<211> LENGTH: 204
<212> TYPE: PRT
<213> ORGANISM: Homo sapiens

<400> SEQUENCE: 6

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
        130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175
```

Arg Ala Gly Gly Val Leu Val Ala Ser His Leu Gln Ser Phe Leu Glu
            180                 185                 190

Val Ser Tyr Arg Val Leu Arg His Leu Ala Gln Pro
            195                 200

<210> SEQ ID NO 7
<211> LENGTH: 171
<212> TYPE: PRT
<213> ORGANISM: Homo sapiens

<400> SEQUENCE: 7

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Ala Gly Cys Leu Ser Gln Leu His Ser Gly Leu Phe
65                  70                  75                  80

Leu Tyr Gln Gly Leu Leu Gln Ala Leu Glu Gly Ile Ser Pro Glu Leu
                85                  90                  95

Gly Pro Thr Leu Asp Thr Leu Gln Leu Asp Val Ala Asp Phe Ala Thr
            100                 105                 110

Thr Ile Trp Gln Gln Met Glu Glu Leu Gly Met Ala Pro Ala Leu Gln
        115                 120                 125

Pro Thr Gln Gly Ala Met Pro Ala Phe Ala Ser Ala Phe Gln Arg Arg
    130                 135                 140

Ala Gly Gly Val Leu Val Ala Ser His Leu Gln Ser Phe Leu Glu Val
145                 150                 155                 160

Ser Tyr Arg Val Leu Arg His Leu Ala Gln Pro
                165                 170

<210> SEQ ID NO 8
<211> LENGTH: 1602
<212> TYPE: DNA
<213> ORGANISM: Artificial Sequence
<220> FEATURE:
<223> OTHER INFORMATION: A non-limiting example of a nucleotide sequence
      that encodes human G-CSF (cDNA sequence).

<400> SEQUENCE: 8
agtcgtggcc ccaggtaatt tcctcccagg cctccatggg gttatgtata aaggcccccc        60
tagagctggg cccaaaaaca gcccggagcc tgcagcccag ccccacccag acccatggct      120
ggacctgcca cccagagccc catgaagctg atggccctgc agctgctgct gtggcacagt      180
gcactctgga cagtgcagga agccaccccc ctgggcctg ccagctccct gccccagagc       240
ttcctgctca agtgcttaga gcaagtgagg aagatccagg gcgatggcgc agcgctccag      300
gagaagctgg tgagtgagtg tgccacctac aagctgtgcc accccgagga gctggtgctg      360
ctcggacact ctctgggcat cccctgggct cccctgagca gctgccccag ccaggccctg      420
cagctggcag gctgcttgag ccaactccat agcggccttt tcctctacca ggggctcctg      480
caggccctgg aagggatctc ccccgagttg gtgccaccct ggacacact gcagctggac      540 gtcgccgact ttgccaccac catctggcag cagatggaag aactgggaat ggccccctgcc     600

```
ctgcagccca cccagggtgc catgccggcc ttcgcctctg ctttccagcg ccgggcagga    660
ggggtcctgg ttgcctccca tctgcagagc ttcctggagg tgtcgtaccg cgttctacgc    720
caccttgccc agccctgagc caagccctcc ccatcccatg tatttatctc tatttaatat    780
ttatgtctat ttaagcctca tatttaaaga cagggaagag cagaacggag ccccaggcct    840
ctgtgtcctt ccctgcattt ctgagtttca ttctcctgcc tgtagcagtg agaaaaagct    900
cctgtcctcc catccctgg actgggaggt agataggtaa ataccaagta tttattacta    960
tgactgctcc ccagccctgg ctctgcaatg ggcactggga tgagccgctg tgagcccctg   1020
gtcctgaggg tccccacctg ggacccttga gagtatcagg tctcccacgt gggagacaag   1080
aaatccctgt ttaatattta acagcagtg ttccccatct gggtccttgc acccctcact    1140
ctggcctcag ccgactgcac agcggcccct gcatccccct tggctgtgagg ccctggaca   1200
agcagaggtg gccagagctg ggaggcatgg ccctggggtc ccacgaattt gctggggaat   1260
ctcgttttc ttcttaagac ttttgggaca tggtttgact cccgaacatc accgacgcgt   1320
ctcctgtttt tctgggtggc ctcggacac ctgccctgcc ccacgagggg tcaggactgt    1380
gactcttttt agggccaggc aggtgcctgg acatttgcct tgctggacgg ggactgggga   1440
tgtgggaggg agcagacagg aggaatcatg tcaggcctgt gtgtgaaagg aagctccact   1500
gtcaccctcc acctcttcac cccccactca ccagtgtccc ctccactgtc acattgtaac   1560
tgaacttcag gataataaag tgtttgcctc caaaaaaaaa aa                      1602

<210> SEQ ID NO 9
<211> LENGTH: 144
<212> TYPE: PRT
<213> ORGANISM: Homo sapiens

<400> SEQUENCE: 9

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 10
<211> LENGTH: 144
<212> TYPE: PRT
<213> ORGANISM: Homo sapiens

<400> SEQUENCE: 10

Met Trp Leu Gln Ser Leu Leu Leu Leu Gly Thr Val Ala Cys Ser Ile
1               5                   10                  15
```

```
Ser Ala Pro Ala Arg Ser Pro Ser Thr Gln Pro Trp Glu His
        20              25              30

Val Asn Ala Ile Gln Glu Ala Arg Leu Leu Asn Leu Ser Arg Asp
            35              40              45

Thr Ala Ala Glu Met Asn Glu Thr Val Glu Val Ile Ser Glu Met Phe
 50              55              60

Asp Leu Gln Glu Pro Thr Cys Leu Gln Thr Arg Leu Glu Leu Tyr Lys
 65              70              75              80

Gln Gly Leu Arg Gly Ser Leu Thr Lys Leu Lys Gly Pro Leu Thr Met
                85              90              95

Met Ala Ser His Tyr Lys Gln His Cys Pro Pro Thr Pro Glu Thr Ser
            100             105             110

Cys Ala Thr Gln Ile Ile Thr Phe Glu Ser Phe Lys Glu Asn Leu Lys
        115             120             125

Asp Phe Leu Leu Val Ile Pro Phe Asp Cys Trp Glu Pro Val Gln Glu
        130             135             140
```

<210> SEQ ID NO 11
<211> LENGTH: 800
<212> TYPE: DNA
<213> ORGANISM: Artificial Sequence
<220> FEATURE:
<223> OTHER INFORMATION: A non-limiting example of a nucleotide sequence
      that encodes human GM-CSF (cDNA sequence).

<400> SEQUENCE: 11

```
acacagagag aaaggctaaa gttctctgga ggatgtggct gcagagcctg ctgctcttgg      60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg gagctgtaca agcaggggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caagagaaac ctgaaggact    420
ttctgcttgt catcccctttt gactgctggg agccagtcca ggagtgagac cggccagatg    480
aggctggcca gccgggggag ctgctctctc atgaaacaag agctagaaac tcaggatggt    540
catcttggag ggaccaaggg gtgggccaca gccatggtgg gagtggcctg gacctgccct    600
gggccacact gaccctgata caggcatggc agaagaatgg gaatatttta tactgacaga    660
aatcagtaat atttatatat ttatattttt aaaatattta tttatttatt tatttaagtt    720
catattccat atttattcaa gatgttttac cgtaataatt attattaaaa atatgcttct    780
acttgaaaaa aaaaaaaaaa                                                800
```

<210> SEQ ID NO 12
<211> LENGTH: 143
<212> TYPE: PRT
<213> ORGANISM: Homo sapiens

<400> SEQUENCE: 12

```
Met Gln Ala Phe Arg Ile Trp Asp Val Asn Gln Lys Thr Phe Tyr Leu
 1               5                  10                  15

Arg Asn Asn Gln Leu Val Ala Gly Tyr Leu Gln Gly Pro Asn Val Asn
             20                  25                  30

Leu Glu Glu Lys Ile Asp Val Val Pro Ile Glu Pro His Ala Leu Phe
```

```
                35                  40                  45
Leu Gly Ile His Gly Gly Lys Met Cys Leu Ser Cys Val Lys Ser Gly
         50                  55                  60
Asp Glu Thr Arg Leu Gln Leu Glu Ala Val Asn Ile Thr Asp Leu Ser
 65                  70                  75                  80
Glu Asn Arg Lys Gln Asp Lys Arg Phe Ala Phe Ile Arg Ser Asp Ser
                 85                  90                  95
Gly Pro Thr Thr Ser Phe Glu Ser Ala Ala Cys Pro Gly Trp Phe Leu
            100                 105                 110
Cys Thr Ala Met Glu Ala Asp Gln Pro Val Ser Leu Thr Asn Met Pro
        115                 120                 125
Asp Glu Gly Val Met Val Thr Lys Phe Tyr Phe Gln Glu Asp Glu
    130                 135                 140

<210> SEQ ID NO 13
<211> LENGTH: 143
<212> TYPE: PRT
<213> ORGANISM: Homo sapiens

<400> SEQUENCE: 13

Met Gln Ala Phe Arg Ile Trp Asp Val Asn Gln Lys Thr Phe Tyr Leu
 1               5                  10                  15
Arg Asn Asn Gln Leu Val Ala Gly Tyr Leu Gln Gly Pro Asn Val Asn
             20                  25                  30
Leu Glu Glu Lys Ile Asp Val Val Pro Ile Glu Pro His Ala Leu Phe
         35                  40                  45
Leu Gly Ile His Gly Gly Lys Met Cys Leu Ser Cys Val Lys Ser Gly
     50                  55                  60
Asp Glu Thr Arg Leu Gln Leu Glu Ala Val Asn Ile Thr Asp Leu Ser
 65                  70                  75                  80
Glu Asn Arg Lys Gln Asp Lys Arg Phe Ala Phe Ile Arg Ser Asp Ser
                 85                  90                  95
Gly Pro Thr Thr Ser Phe Glu Ser Ala Ala Cys Pro Gly Trp Phe Leu
            100                 105                 110
Cys Thr Ala Met Glu Ala Asp Gln Pro Val Ser Leu Thr Asn Met Pro
        115                 120                 125
Asp Glu Gly Val Met Val Thr Lys Phe Tyr Phe Gln Glu Asp Glu
    130                 135                 140

<210> SEQ ID NO 14
<211> LENGTH: 177
<212> TYPE: PRT
<213> ORGANISM: Homo sapiens

<400> SEQUENCE: 14

Met Glu Ile Cys Arg Gly Leu Arg Ser His Leu Ile Thr Leu Leu Leu
 1               5                  10                  15
Phe Leu Phe His Ser Glu Thr Ile Cys Arg Pro Ser Gly Arg Lys Ser
             20                  25                  30
Ser Lys Met Gln Ala Phe Arg Ile Trp Asp Val Asn Gln Lys Thr Phe
         35                  40                  45
Tyr Leu Arg Asn Asn Gln Leu Val Ala Gly Tyr Leu Gln Gly Pro Asn
     50                  55                  60
Val Asn Leu Glu Glu Lys Ile Asp Val Val Pro Ile Glu Pro His Ala
 65                  70                  75                  80
Leu Phe Leu Gly Ile His Gly Gly Lys Met Cys Leu Ser Cys Val Lys
```

```
                      85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
            115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 15
<211> LENGTH: 180
<212> TYPE: PRT
<213> ORGANISM: Homo sapiens

<400> SEQUENCE: 15

Met Ala Leu Ala Asp Leu Tyr Glu Glu Gly Gly Gly Gly Gly Gly Glu
1               5                   10                  15

Gly Glu Asp Asn Ala Asp Ser Lys Glu Thr Ile Cys Arg Pro Ser Gly
                20                  25                  30

Arg Lys Ser Ser Lys Met Gln Ala Phe Arg Ile Trp Asp Val Asn Gln
            35                  40                  45

Lys Thr Phe Tyr Leu Arg Asn Asn Gln Leu Val Ala Gly Tyr Leu Gln
        50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
                100                 105                 110

Ile Thr Asp Leu Ser Glu Asn Arg Lys Gln Asp Lys Arg Phe Ala Phe
            115                 120                 125

Ile Arg Ser Asp Ser Gly Pro Thr Thr Ser Phe Glu Ser Ala Ala Cys
        130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180

<210> SEQ ID NO 16
<211> LENGTH: 159
<212> TYPE: PRT
<213> ORGANISM: Homo sapiens

<400> SEQUENCE: 16

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
                20                  25                  30

Arg Asn Asn Gln Leu Val Ala Gly Tyr Leu Gln Gly Pro Asn Val Asn
            35                  40                  45
```

```
Leu Glu Glu Lys Ile Asp Val Val Pro Ile Glu Pro His Ala Leu Phe
         50                  55                  60

Leu Gly Ile His Gly Gly Lys Met Cys Leu Ser Cys Val Lys Ser Gly
 65                  70                  75                  80

Asp Glu Thr Arg Leu Gln Leu Glu Ala Val Asn Ile Thr Asp Leu Ser
                 85                  90                  95

Glu Asn Arg Lys Gln Asp Lys Arg Phe Ala Phe Ile Arg Ser Asp Ser
             100                 105                 110

Gly Pro Thr Thr Ser Phe Glu Ser Ala Ala Cys Pro Gly Trp Phe Leu
         115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155
```

```
<210> SEQ ID NO 17
<211> LENGTH: 177
<212> TYPE: PRT
<213> ORGANISM: Homo sapiens

<400> SEQUENCE: 17

Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
                 20                  25                  30

Ser Lys Met Gln Ala Phe Arg Ile Trp Asp Val Asn Gln Lys Thr Phe
             35                  40                  45

Tyr Leu Arg Asn Asn Gln Leu Val Ala Gly Tyr Leu Gln Gly Pro Asn
 50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

```
<210> SEQ ID NO 18
<211> LENGTH: 159
<212> TYPE: PRT
<213> ORGANISM: Homo sapiens

<400> SEQUENCE: 18

Met Ala Leu Glu Thr Ile Cys Arg Pro Ser Gly Arg Lys Ser Ser Lys
 1               5                  10                  15

Met Gln Ala Phe Arg Ile Trp Asp Val Asn Gln Lys Thr Phe Tyr Leu
                 20                  25                  30
```

Arg Asn Asn Gln Leu Val Ala Gly Tyr Leu Gln Gly Pro Asn Val Asn
         35                  40                  45

Leu Glu Glu Lys Ile Asp Val Val Pro Ile Glu Pro His Ala Leu Phe
 50                  55                  60

Leu Gly Ile His Gly Gly Lys Met Cys Leu Ser Cys Val Lys Ser Gly
 65                  70                  75                  80

Asp Glu Thr Arg Leu Gln Leu Glu Ala Val Asn Ile Thr Asp Leu Ser
             85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
            115                 120                 125

Cys Thr Ala Met Glu Ala Asp Gln Pro Val Ser Leu Thr Asn Met Pro
 130                 135                 140

Asp Glu Gly Val Met Val Thr Lys Phe Tyr Phe Gln Glu Asp Glu
 145                 150                 155

<210> SEQ ID NO 19
<211> LENGTH: 180
<212> TYPE: PRT
<213> ORGANISM: Homo sapiens

<400> SEQUENCE: 19

Met Ala Leu Ala Asp Leu Tyr Glu Glu Gly Gly Gly Gly Gly Gly Glu
 1               5                  10                  15

Gly Glu Asp Asn Ala Asp Ser Lys Glu Thr Ile Cys Arg Pro Ser Gly
             20                  25                  30

Arg Lys Ser Ser Lys Met Gln Ala Phe Arg Ile Trp Asp Val Asn Gln
             35                  40                  45

Lys Thr Phe Tyr Leu Arg Asn Asn Gln Leu Val Ala Gly Tyr Leu Gln
 50                  55                  60

Gly Pro Asn Val Asn Leu Glu Glu Lys Ile Asp Val Val Pro Ile Glu
 65                  70                  75                  80

Pro His Ala Leu Phe Leu Gly Ile His Gly Gly Lys Met Cys Leu Ser
                 85                  90                  95

Cys Val Lys Ser Gly Asp Glu Thr Arg Leu Gln Leu Glu Ala Val Asn
            100                 105                 110

Ile Thr Asp Leu Ser Glu Asn Arg Lys Gln Asp Lys Arg Phe Ala Phe
            115                 120                 125

Ile Arg Ser Asp Ser Gly Pro Thr Thr Ser Phe Glu Ser Ala Ala Cys
 130                 135                 140

Pro Gly Trp Phe Leu Cys Thr Ala Met Glu Ala Asp Gln Pro Val Ser
 145                 150                 155                 160

Leu Thr Asn Met Pro Asp Glu Gly Val Met Val Thr Lys Phe Tyr Phe
                 165                 170                 175

Gln Glu Asp Glu
            180

<210> SEQ ID NO 20
<211> LENGTH: 143
<212> TYPE: PRT
<213> ORGANISM: Homo sapiens

<400> SEQUENCE: 20

Met Gln Ala Phe Arg Ile Trp Asp Val Asn Gln Lys Thr Phe Tyr Leu
 1               5                  10                  15

```
Arg Asn Asn Gln Leu Val Ala Gly Tyr Leu Gln Gly Pro Asn Val Asn
            20                  25                  30

Leu Glu Glu Lys Ile Asp Val Val Pro Ile Pro His Ala Leu Phe
        35                  40                  45

Leu Gly Ile His Gly Gly Lys Met Cys Leu Ser Cys Val Lys Ser Gly
    50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Phe Gln Glu Asp Glu
        130                 135                 140

<210> SEQ ID NO 21
<211> LENGTH: 1802
<212> TYPE: DNA
<213> ORGANISM: Artificial Sequence
<220> FEATURE:
<223> OTHER INFORMATION: A non-limiting example of a nucleotide sequence
      that encodes human IL1RA (cDNA sequence).

<400> SEQUENCE: 21
gggcagctcc accctgggag ggactgtggc ccaggtactg cccgggtgct actttatggg      60
cagcagctca gttgagttag agtctggaag acctcagaag acctcctgtc ctatgaggcc    120
ctccccatgg ctttagagac gatctgccga ccctctggga gaaaatccag caagatgcaa    180
gccttcagaa tctgggatgt taaccagaag accttctatc tgaggaacaa ccaactagtt    240
gctggatact tgcaaggacc aaatgtcaat ttagaagaaa agatagatgt ggtacccatt    300
gagcctcatg ctctgttctt gggaatccat ggagggaaga tgtgcctgtc ctgtgtcaag    360
tctggtgatg agaccagact ccagctggag gcagttaaca tcactgacct gagcgagaac    420
agaaagcagg acaagcgctt cgccttcatc cgctcagaca gtggccccac caccagtttt    480
gagtctgccg cctgccccgg ttggttcctc tgcacagcga tggaagctga ccagcccgtc    540
agcctcacca atatgcctga cgaaggcgtc atggtcacca aattctactt ccaggaggac    600
gagtagtact gcccaggcct gcctgttccc attcttgcat ggcaaggact gcagggactg    660
ccagtccccc tgcccaggg ctcccggcta tgggggcact gaggaccagc cattgagggg    720
tggaccctca gaaggcgtca caacaacctg gtcacaggac tctgcctcct cttcaactga    780
ccagcctcca tgctgcctcc agaatggtct ttctaatgtg tgaatcagag cacagcagcc    840
cctgcacaaa gcccttccat gtcgcctctg cattcaggat caaaccccga ccacctgccc    900
aacctgctct cctcttgcca ctgcctcttc ctccctcatt ccaccttccc atgccctgga    960
tccatcaggc cacttgatga cccccaacca agtggctccc acaccctgtt ttacaaaaaa   1020
gaaaagacca gtccatgagg gaggttttta agggtttgtg gaaatgaaa attaggattt    1080 catgattttt ttttttcagt ccccgtgaag gagagccctt catttggaga ttatgttctt   1140
tcggggagag gctgaggact taaaatattc ctgcatttgt gaaatgatgg tgaaagtaag   1200
tggtagcttt tcccttcttt ttcttctttt tttgtgatgt cccaacttgt aaaaattaaa   1260
agttatggta ctatgttagc cccataattt ttttttttcct tttaaaacac ttccataatc   1320
```

```
tggactcctc tgtccaggca ctgctgccca gcctccaagc tccatctcca ctccagattt    1380
tttacagctg cctgcagtac tttacctcct atcagaagtt tctcagctcc caaggctctg    1440
agcaaatgtg ctcctgggg gttctttctt cctctgctga aggaataaat tgctccttga     1500
cattgtagag cttctggcac ttggagactt gtatgaaaga tggctgtgcc tctgcctgtc    1560
tcccccaccg ggctgggagc tctgcagagc aggaaacatg actcgtatat gtctcaggtc    1620
cctgcagggc caagcaccta gcctcgctct tggcaggtac tcagcgaatg aatgctgtat    1680
atgttgggtg caaagttccc tacttcctgt gacttcagct ctgttttaca ataaaatctt    1740
gaaaatgcct aaaaaaaaaa aaaaaaaaaa aaaaaaaaaa aaaaaaaaaa aaaaaaaaaa    1800
aa                                                                  1802
```

<210> SEQ ID NO 22
<211> LENGTH: 212
<212> TYPE: PRT
<213> ORGANISM: Homo sapiens

<400> SEQUENCE: 22

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 23
<211> LENGTH: 136
<212> TYPE: PRT
<213> ORGANISM: Homo sapiens

<400> SEQUENCE: 23

Met Cys Glu Ser Ser Lys Glu Ala Leu Ala Glu Asn Asn Leu Asn Leu
1               5                   10                  15

```
Pro Lys Met Ala Glu Lys Asp Gly Cys Phe Gln Ser Gly Phe Asn Glu
            20                  25                  30

Glu Thr Cys Leu Val Lys Ile Ile Thr Gly Leu Leu Glu Phe Glu Val
            35                  40                  45

Tyr Leu Glu Tyr Leu Gln Asn Arg Phe Glu Ser Ser Glu Glu Gln Ala
 50                  55                  60

Arg Ala Val Gln Met Ser Thr Lys Val Leu Ile Gln Phe Leu Gln Lys
 65                  70                  75                  80

Lys Ala Lys Asn Leu Asp Ala Ile Thr Thr Pro Asp Pro Thr Thr Asn
                85                  90                  95

Ala Ser Leu Leu Thr Lys Leu Gln Ala Gln Asn Gln Trp Leu Gln Asp
            100                 105                 110

Met Thr Thr His Leu Ile Leu Arg Ser Phe Lys Glu Phe Leu Gln Ser
            115                 120                 125

Ser Leu Arg Ala Leu Arg Gln Met
            130                 135

<210> SEQ ID NO 24
<211> LENGTH: 212
<212> TYPE: PRT
<213> ORGANISM: Homo sapiens

<400> SEQUENCE: 24

Met Asn Ser Phe Ser Thr Ser Ala Phe Gly Pro Val Ala Phe Ser Leu
 1               5                  10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
 130                 135                 140

Met Ser Thr Lys Val Leu Ile Gln Phe Leu Gln Lys Lys Ala Lys Asn
 145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
            195                 200                 205

Leu Arg Gln Met
 210

<210> SEQ ID NO 25
<211> LENGTH: 1197
<212> TYPE: DNA
<213> ORGANISM: Artificial Sequence
```

<220> FEATURE:
<223> OTHER INFORMATION: A non-limiting example of a nucleotide sequence that encodes human IL-6 (cDNA squence).

<400> SEQUENCE: 25

```
gtctcaatat tagagtctca accccccaata aatataggac tggagatgtc tgaggctcat      60
tctgccctcg agcccaccgg gaacgaaaga gaagctctat ctcccctcca ggagcccagc     120
tatgaactcc ttctccacaa gcgccttcgg tccagttgcc ttctccctgg ggctgctcct     180
ggtgttgcct gctgccttcc ctgccccagt accccccagga gaagattcca agatgtagc     240
cgccccacac agacagccac tcacctcttc agaacgaatt gacaaacaaa ttcggtacat     300
cctcgacggc atctcagccc tgagaaagga gacatgtaac aagagtaaca tgtgtgaaag     360
cagcaaagag gcactggcag aaaacaacct gaaccttcca agatggctg aaaaagatgg     420
atgcttccaa tctggattca atgaggagac ttgcctggtg aaaatcatca ctggtcttt     480
ggagtttgag gtatacctag agtacctcca gaacagattt gagagtagtg aggaacaagc     540
cagagctgtg cagatgagta caaaagtcct gatccagttc ctgcagaaaa aggcaaagaa     600
tctagatgca ataaccaccc ctgacccaac cacaaatgcc agcctgctga cgaagctgca     660
ggcacagaac cagtggctgc aggacatgac aactcatctc attctgcgca gctttaagga     720
gttcctgcag tccagcctga gggctcttcg gcaaatgtag catgggcacc tcagattgtt     780
gttgttaatg ggcattcctt cttctggtca gaaacctgtc cactgggcac agaacttatg     840
ttgttctcta tggagaacta aaagtatgag cgttaggaca ctattttaat tattttaat     900
ttattaatat ttaaatatgt gaagctgagt taatttatgt aagtcatatt tatatttta     960
agaagtacca cttgaaacat tttatgtatt agttttgaaa taataatgga aagtggctat    1020
gcagtttgaa tatcctttgt ttcagagcca gatcatttct tggaaagtgt aggcttacct    1080
caaataaatg gctaacttat acatattttt aaagaaatat ttatattgta tttatataat    1140
gtataaatgg ttttatacc aataaatggc attttaaaaa attcagcaaa aaaaaaa       1197
```

<210> SEQ ID NO 26
<211> LENGTH: 178
<212> TYPE: PRT
<213> ORGANISM: Homo sapiens

<400> SEQUENCE: 26

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
```

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 27
<211> LENGTH: 178
<212> TYPE: PRT
<213> ORGANISM: Homo sapiens

<400> SEQUENCE: 27

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 28
<211> LENGTH: 1629
<212> TYPE: DNA
<213> ORGANISM: Artificial Sequence
<220> FEATURE:
<223> OTHER INFORMATION: A non-limiting example of a nucleotide sequence
      that encodes human IL-10 (cDNA sequence).

<400> SEQUENCE: 28
acacatcagg ggcttgctct tgcaaaacca aaccacaaga cagacttgca aaagaaggca      60
tgcacagctc agcactgctc tgttgcctgg tcctcctgac tggggtgagg gccagcccag     120
gccagggcac ccagtctgag aacagctgca cccacttccc aggcaacctg cctaacatgc     180
ttcgagatct ccgagatgcc ttcagcagag tgaagacttt ctttcaaatg aaggatcagc     240
tggacaactt gttgttaaag gagtccttgc tggaggactt taagggttac ctgggttgcc     300
aagccttgtc tgagatgatc cagttttacc tggaggaggt gatgcccaa gctgagaacc     360 aagacccaga catcaaggcg catgtgaact ccctggggga gaacctgaag accctcaggc     420
tgaggctacg cgctgtcat cgattcttc cctgtgaaaa caagagcaag gccgtggagc      480

-continued

```
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaaccctta ttgtacctct cttatagaat   720
atttattacc tctgatacct caaccccccat ttctatttat ttactgagct tctctgtgaa   780
cgatttagaa agaagcccaa tattataatt tttttcaata tttattattt tcacctgttt    840
ttaagctgtt tccataggt gacacactat ggtatttgag tgttttaaga taaattataa     900
gttacataag ggaggaaaaa aaatgttctt tggggagcca acagaagctt ccattccaag    960
cctgaccacg ctttctagct gttgagctgt tttccctgac ctccctctaa tttatcttgt   1020
ctctgggctt ggggcttcct aactgctaca aatactctta ggaagagaaa ccagggagcc   1080
cctttgatga ttaattcacc ttccagtgtc tcggagggat tcccctaacc tcattcccca   1140
accacttcat tcttgaaagc tgtggccagc ttgttattta taacaaccta aatttggttc   1200
taggccgggc gcggtggctc acgcctgtaa tcccagcact ttgggaggct gaggcgggtg   1260
gatcacttga ggtcaggagt tcctaaccag cctggtcaac atggtgaaac cccgtctcta   1320
ctaaaaatac aaaaattagc cgggcatggt ggcgcgcacc tgtaatccca gctacttggg   1380
aggctgaggc aagagaattg cttgaaccca ggagatggaa gttgcagtga gctgatatca   1440
tgcccctgta ctccagcctg ggtgacagag caagactctg tctcaaaaaa taaaaataaa   1500
aataaatttg gttctaatag aactcagttt taactagaat ttattcaatt cctctgggaa   1560
tgttacattg tttgtctgtc ttcatagcag attttaattt tgaataaata aatgtatctt   1620
attcacatc                                                           1629
```

<210> SEQ ID NO 29
<211> LENGTH: 269
<212> TYPE: PRT
<213> ORGANISM: Homo sapiens

<400> SEQUENCE: 29

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160
```

```
Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265

<210> SEQ ID NO 30
<211> LENGTH: 269
<212> TYPE: PRT
<213> ORGANISM: Homo sapiens

<400> SEQUENCE: 30

Met Ala Glu Val Pro Glu Leu Ala Ser Glu Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265
```

<210> SEQ ID NO 31
<211> LENGTH: 1498
<212> TYPE: DNA
<213> ORGANISM: Artificial Sequence
<220> FEATURE:
<223> OTHER INFORMATION: A non-limiting example of a nucleotide sequence
that encodes human IL-1b (cDNA sequence).

<400> SEQUENCE: 31

| | | | | | |
|---|---|---|---|---|---|
| accaaacctc | ttcgaggcac | aaggcacaac | aggctgctct | gggattctct | tcagccaatc | 60 |
| ttcattgctc | aagtgtctga | agcagccatg | gcagaagtac | ctgagctcgc | cagtgaaatg | 120 |
| atggcttatt | acagtggcaa | tgaggatgac | ttgttctttg | aagctgatgg | ccctaaacag | 180 |
| atgaagtgct | ccttccagga | cctggacctc | tgccctctgg | atggcggcat | ccagctacga | 240 |
| atctccgacc | accactacag | caagggcttc | aggcaggccg | cgtcagttgt | tgtggccatg | 300 |
| gacaagctga | ggaagatgct | ggttccctgc | ccacagacct | tccaggagaa | tgacctgagc | 360 |
| accttctttc | ccttcatctt | tgaagaagaa | cctatcttct | tcgacacatg | ggataacgag | 420 |
| gcttatgtgc | acgatgcacc | tgtacgatca | ctgaactgca | cgctccggga | ctcacagcaa | 480 |
| aaaagcttgg | tgatgtctgg | tccatatgaa | ctgaaagctc | tccacctcca | gggacaggat | 540 |
| atggagcaac | aagtggtgtt | ctccatgtcc | tttgtacaag | agaagaaag | taatgacaaa | 600 |
| atacctgtgg | ccttgggcct | caaggaaaag | aatctgtacc | tgtcctgcgt | gttgaaagat | 660 |
| gataagccca | ctctacagct | ggagagtgta | gatcccaaaa | attacccaaa | gaagaagatg | 720 |
| gaaaagcgat | ttgtcttcaa | caagataaa | atcaataaca | agctggaatt | tgagtctgcc | 780 |
| cagttcccca | actggtacat | cagcacctct | caagcagaaa | acatgcccgt | cttcctggga | 840 |
| gggaccaaag | gcggcagga | tataactgac | ttcaccatgc | aatttgtgtc | ttcctaaaga | 900 |
| gagctgtacc | cagagagtcc | tgtgctgaat | gtggactcaa | tccctagggc | tggcagaaag | 960 |
| ggaacagaaa | ggttttgag | tacggctata | gcctggactt | tcctgttgtc | tacaccaatg | 1020 |
| cccaactgcc | tgccttaggg | tagtgctaag | aggatctcct | gtccatcagc | caggacagtc | 1080 |
| agctctctcc | tttcagggcc | aatccccagc | cctttttgttg | agccaggcct | ctctcacctc | 1140 |
| tcctactcac | ttaaagcccg | cctgacagaa | accacggcca | catttggttc | taagaaaccc | 1200 |
| tctgtcattc | gctcccacat | tctgatgagc | aaccgcttcc | ctatttattt | atttatttgt | 1260 |
| ttgtttgttt | tattcattgg | tctaatttat | tcaaggggg | caagaagtag | cagtgtctgt | 1320 |
| aaaagagcct | agttttttaat | agctatgaa | tcaattcaat | ttggactggt | gtgctctctt | 1380 |
| taaatcaagt | cctttaatta | agactgaaaa | tatataagct | cagattattt | aaatgggaat | 1440 |
| atttataaat | gagcaaatat | catactgttc | aatggttctg | aaataaactt | cactgaag | 1498 |

<210> SEQ ID NO 32
<211> LENGTH: 155
<212> TYPE: PRT
<213> ORGANISM: Homo sapiens

<400> SEQUENCE: 32

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

```
Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 33
<211> LENGTH: 155
<212> TYPE: PRT
<213> ORGANISM: Homo sapiens

<400> SEQUENCE: 33

Met Thr Pro Gly Lys Thr Ser Leu Val Ser Leu Leu Leu Leu Leu Ser
 1               5                  10                  15

Leu Glu Ala Ile Val Lys Ala Gly Ile Thr Ile Pro Arg Asn Pro Gly
             20                  25                  30

Cys Pro Asn Ser Glu Asp Lys Asn Phe Pro Arg Thr Val Met Val Asn
         35                  40                  45

Leu Asn Ile His Asn Arg Asn Thr Asn Thr Asn Pro Lys Arg Ser Ser
 50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 34
<211> LENGTH: 1859
<212> TYPE: DNA
<213> ORGANISM: Artificial Sequence
<220> FEATURE:
<223> OTHER INFORMATION: A non-limiting example of a nucleotide sequence
      that encodes human IL-17A (cDNA sequence).

<400> SEQUENCE: 34
gcaggcacaa actcatccat ccccagttga ttggaagaaa caacgatgac tcctgggaag        60
acctcattgg tgtcactgct actgctgctg agcctggagg ccatagtgaa ggcaggaatc      120
acaatcccac gaaatccagg atgcccaaat tctgaggaca agaacttccc ccggactgtg      180
atggtcaacc tgaacatcca taaccggaat accaatacca tcccaaaag gtcctcagat      240 tactacaacc gatccacctc accttggaat ctccaccgca atgaggaccc tgagagatat      300
```

```
ccctctgtga tctgggaggc aaagtgccgc cacttgggct gcatcaacgc tgatgggaac    360
gtggactacc acatgaactc tgtccccatc cagcaagaga tcctggtcct gcgcagggag    420
cctccacact gccccaactc cttccggctg gagaagatac tggtgtccgt gggctgcacc    480
tgtgtcaccc cgattgtcca ccatgtggcc taagagctct ggggagccca cactccccaa    540
agcagttaga ctatggagag ccgacccagc ccctcaggaa ccctcatcct tcaaagacag    600
cctcatttcg gactaaactc attagagttc ttaaggcagt tgtccaatt aaagcttcag     660 aggtaacact tggccaagat atgagatctg aattaccttt ccctctttcc aagaaggaag    720
gtttgactga gtaccaattt gcttcttgtt tactttttta agggctttaa gttatttatg    780
tatttaatat gccctgagat aactttgggg tataagattc cattttaatg aattacctac    840
tttattttgt ttgtcttttt aaagaagata agattctggg cttggaatt ttattattta     900 aaaggtaaaa cctgtattta tttgagctat ttaaggatct atttatgttt aagtatttag    960
aaaaaggtga aaaagcacta ttatcagttc tgcctaggta aatgtaagat agaattaaat   1020
ggcagtgcaa aatttctgag tctttacaac atacggatat agtatttcct cctctttgtt   1080
tttaaaagtt ataacatggc tgaaaagaaa gattaaaccct actttcatat gtattaattt   1140
aaattttgca atttgttgag gttttacaag agatacagca agtctaactc tctgttccat   1200 taaacccctta taataaaatc cttctgtaat aataaagttt caaagaaaa tgtttatttg    1260 ttctcattaa atgtattta gcaaactcag ctcttccctta ttgggaagag ttatgcaaat   1320
tctcctataa gcaaaacaaa gcatgtcttt gagtaacaat gacctggaaa tacccaaaat   1380
tccaagttct cgatttcaca tgccttcaag actgaacacc gactaaggtt ttcatactat   1440
tagccaatgc tgtagacaga agcattttga taggaataga gcaaataaga taatggccct   1500
gaggaatggc atgtcattat taaagatcat atggggaaaa tgaaaccctc cccaaaatac   1560
aagaagttct gggaggagac attgtcttca gactacaatg tccagtttct cccctagact   1620
caggcttcct ttggagatta aggcccctca gagatcaaca gaccaacatt tttctcttcc   1680
tcaagcaaca ctcctagggc ctggcttctg tctgatcaag gcaccacaca acccagaaag   1740
gagctgatgg ggcagaacga actttaagta tgagaaaagt tcagcccaag taaaataaaa   1800
actcaatcac attcaattcc agagtagttt caagtttcac atcgtaacca ttttcgccc    1859
```

<210> SEQ ID NO 35
<211> LENGTH: 233
<212> TYPE: PRT
<213> ORGANISM: Homo sapiens

<400> SEQUENCE: 35

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95
```

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 36
<211> LENGTH: 233
<212> TYPE: PRT
<213> ORGANISM: Homo sapiens

<400> SEQUENCE: 36

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
210                 215                 220

Gln Val Tyr Phe Gly Ile Ile Ala Leu
225                 230

<210> SEQ ID NO 37
<211> LENGTH: 1686
<212> TYPE: DNA
<213> ORGANISM: Artificial Sequence
<220> FEATURE:
<223> OTHER INFORMATION: A non-limiting example of a nucleotide sequence that encodes human TNF-a (cDNA sequence).

<400> SEQUENCE: 37

```
cagacgctcc ctcagcaagg acagcagagg accagctaag agggagagaa gcaactacag       60
accccccctg aaaacaaccc tcagacgcca catcccctga caagctgcca ggcaggttct      120
cttcctctca catactgacc cacggctcca ccctctctcc cctggaaagg acaccatgag      180
cactgaaagc atgatccggg acgtggagct ggccgaggag gcgctcccca agaagacagg      240
ggggcccag  ggctccaggc ggtgcttgtt cctcagcctc ttctccttcc tgatcgtggc      300
aggcgccacc acgctcttct gcctgctgca ctttggagtg atcggccccc agagggaaga      360
gttcccagg  gacctctctc taatcagccc tctggcccag gcagtcagat catcttctcg      420
aaccccgagt gacaagcctg tagcccatgt tgtagcaaac cctcaagctg agggggcagct     480
ccagtggctg aaccgccggg ccaatgccct cctggccaat ggcgtggagc tgagagataa      540
ccagctggtg gtgccatcag agggcctgta cctcatctac tcccaggtcc tcttcaaggg      600
ccaaggctgc ccctccaccc atgtgctcct cacccacacc atcagccgca tcgccgtctc      660
ctaccagacc aaggtcaacc tcctctctgc catcaagagc ccctgccaga gggagacccc      720
agaggggggct gaggccaagc cctggtatga gcccatctat ctgggagggg tcttccagct    780
ggagaagggt gaccgactca gcgctgagat caatcggccc gactatctcg actttgccga      840
gtctgggcag gtctactttg gatcattgc cctgtgagga ggacgaacat ccaaccttcc      900
caaacgcctc ccctgccca  atccctttat taccccctcc ttcagacacc ctcaacctct      960
tctggctcaa aaagagaatt gggggcttag ggtcggaacc caagcttaga actttaagca    1020
acaagaccac cacttcgaaa cctgggattc aggaatgtgt ggcctgcaca gtgaagtgct    1080
ggcaaccact aagaattcaa actggggcct ccagaactca ctggggccta cagctttgat    1140
ccctgacatc tggaatctgg agaccaggga gcctttggtt ctggccagaa tgctgcagga    1200
cttgagaaga cctcacctag aaattgacac aagtggacct taggccttcc tctctccaga    1260
tgtttccaga cttccttgag acacggagcc cagccctccc catggagcca gctccctcta    1320
tttatgtttg cacttgtgat tatttattat ttatttatta tttatttatt tacagatgaa    1380
tgtatttatt tgggagaccg gggtatcctg ggggacccaa tgtaggagct gccttggctc    1440
agacatgttt tccgtgaaaa cggagctgaa caataggctg ttcccatgta gcccctggc     1500
ctctgtgcct tcttttgatt atgttttta  aaatattat  ctgattaagt tgtctaaaca    1560
atgctgattt ggtgaccaac tgtcactcat tgctgagcct ctgctcccca ggggagttgt    1620
gtctgtaatc gccctactat tcagtggcga gaaataaagt ttgcttagaa aagaaaaaaa    1680
aaaaaa                                                              1686
```

<210> SEQ ID NO 38
<211> LENGTH: 166
<212> TYPE: PRT
<213> ORGANISM: Homo sapiens

<400> SEQUENCE: 38

Met Lys Tyr Thr Ser Tyr Ile Leu Ala Phe Gln Leu Cys Ile Val Leu

```
            1               5                  10                 15
Gly Ser Leu Gly Cys Tyr Cys Gln Asp Pro Tyr Val Lys Glu Ala Glu
            20                 25                 30

Asn Leu Lys Lys Tyr Phe Asn Ala Gly His Ser Asp Val Ala Asp Asn
            35                 40                 45

Gly Thr Leu Phe Leu Gly Ile Leu Lys Asn Trp Lys Glu Glu Ser Asp
            50                 55                 60

Arg Lys Ile Met Gln Ser Gln Ile Val Ser Phe Tyr Phe Lys Leu Phe
 65                 70                 75                 80

Lys Asn Phe Lys Asp Asp Gln Ser Ile Gln Lys Ser Val Glu Thr Ile
                85                 90                 95

Lys Glu Asp Met Asn Val Lys Phe Phe Asn Ser Asn Lys Lys Lys Arg
                100                105                110

Asp Asp Phe Glu Lys Leu Thr Asn Tyr Ser Val Thr Asp Leu Asn Val
                115                120                125

Gln Arg Lys Ala Ile His Glu Leu Ile Gln Val Met Ala Glu Leu Ser
                130                135                140

Pro Ala Ala Lys Thr Gly Lys Arg Lys Arg Ser Gln Met Leu Phe Arg
145                 150                155                160

Gly Arg Arg Ala Ser Gln
                165
```

<210> SEQ ID NO 39
<211> LENGTH: 166
<212> TYPE: PRT
<213> ORGANISM: Homo sapiens

<400> SEQUENCE: 39

```
Met Lys Tyr Thr Ser Tyr Ile Leu Ala Phe Gln Leu Cys Ile Val Leu
 1               5                  10                 15

Gly Ser Leu Gly Cys Tyr Cys Gln Asp Pro Tyr Val Lys Glu Ala Glu
            20                 25                 30

Asn Leu Lys Lys Tyr Phe Asn Ala Gly His Ser Asp Val Ala Asp Asn
            35                 40                 45

Gly Thr Leu Phe Leu Gly Ile Leu Lys Asn Trp Lys Glu Glu Ser Asp
            50                 55                 60

Arg Lys Ile Met Gln Ser Gln Ile Val Ser Phe Tyr Phe Lys Leu Phe
 65                 70                 75                 80

Lys Asn Phe Lys Asp Asp Gln Ser Ile Gln Lys Ser Val Glu Thr Ile
                85                 90                 95

Lys Glu Asp Met Asn Val Lys Phe Phe Asn Ser Asn Lys Lys Lys Arg
                100                105                110

Asp Asp Phe Glu Lys Leu Thr Asn Tyr Ser Val Thr Asp Leu Asn Val
                115                120                125

Gln Arg Lys Ala Ile His Glu Leu Ile Gln Val Met Ala Glu Leu Ser
                130                135                140

Pro Ala Ala Lys Thr Gly Lys Arg Lys Arg Ser Gln Met Leu Phe Arg
145                 150                155                160

Gly Arg Arg Ala Ser Gln
                165
```

<210> SEQ ID NO 40
<211> LENGTH: 1240
<212> TYPE: DNA
<213> ORGANISM: Artificial Sequence
<220> FEATURE:

<223> OTHER INFORMATION: A non-limiting example of a nucleotide sequence
      that encodes human IFN-g (cDNA sequence).

<400> SEQUENCE: 40

```
cacattgttc tgatcatctg aagatcagct attagaagag aaagatcagt taagtccttt      60
ggacctgatc agcttgatac aagaactact gatttcaact tctttggctt aattctctcg     120
gaaacgatga atatacaag ttatatcttg gcttttcagc tctgcatcgt tttgggttct      180
cttggctgtt actgccagga cccatatgta aagaagcag aaaaccttaa gaaatatttt      240
aatgcaggtc attcagatgt agcggataat ggaactcttt tcttaggcat tttgaagaat     300
tggaaagagg agagtgacag aaaaataatg cagagccaaa ttgtctcctt ttacttcaaa     360
ctttttaaaa actttaaaga tgaccagagc atccaaaaga gtgtggagac catcaaggaa     420
gacatgaatg tcaagttttt caatagcaac aaaaagaaac gagatgactt cgaaaagctg     480
actaattatt cggtaactga cttgaatgtc aacgcaaag caatacatga actcatccaa      540
gtgatggctg aactgtcgcc agcagctaaa acagggaagc gaaaaaggag tcagatgctg     600
tttcgaggtc gaagagcatc ccagtaatgg ttgtcctgcc tgcaatattt gaattttaaa     660
tctaaatcta tttattaata tttaacatta tttatatggg gaatatattt ttagactcat     720
caatcaaata agtatttata atagcaactt tgtgtaatg aaaatgaata tctattaata      780
tatgtattat ttataattcc tatatcctgt gactgtctca cttaatcctt tgttttctga     840
ctaattaggc aaggctatgt gattacaagg ctttatctca ggggccaact aggcagccaa     900
cctaagcaag atcccatggg ttgtgtgttt atttcacttg atgatacaat gaacacttat     960
aagtgaagtg atactatcca gttactgccg gtttgaaaat atgcctgcaa tctgagccag    1020
tgctttaatg gcatgtcaga cagaacttga atgtgtcagg tgaccctgat gaaaacatag    1080
catctcagga gatttcatgc ctggtgcttc caaatattgt tgacaactgt gactgtaccc    1140
aaatggaaag taactcattt gttaaaatta tcaatatcta atatatatga ataaagtgta    1200
agttcacaac aaaaaaaaaa aaaaaaaaa aaaaaaaaa                            1240
```

<210> SEQ ID NO 41
<211> LENGTH: 99
<212> TYPE: PRT
<213> ORGANISM: Homo sapiens

<400> SEQUENCE: 41

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

<210> SEQ ID NO 42
<211> LENGTH: 99
<212> TYPE: PRT

<213> ORGANISM: Homo sapiens

<400> SEQUENCE: 42

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 43
<211> LENGTH: 760
<212> TYPE: DNA
<213> ORGANISM: Artificial Sequence
<220> FEATURE:
<223> OTHER INFORMATION: A non-limiting example of a nucleotide sequence
      that encodes human MCP-1 (cDNA sequence).

<400> SEQUENCE: 43
gaggaaccga gaggctgaga ctaacccaga aacatccaat tctcaaactg aagctcgcac      60
tctcgcctcc agcatgaaag tctctgccgc ccttctgtgc ctgctgctca tagcagccac     120
cttcattccc caagggctcg ctcagccaga tgcaatcaat gccccagtca cctgctgtta    180
taacttcacc aataggaaga tctcagtgca gaggctcgcg agctatagaa gaatcaccag    240
cagcaagtgt cccaaagaag ctgtgatctt caagaccatt gtggccaagg agatctgtgc    300
tgaccccaag cagaagtggg ttcaggattc catggaccac ctggacaagc aaacccaaac    360
tccgaagact tgaacactca ctccacaacc caagaatctg cagctaactt attttcccct    420
agctttcccc agacaccctg ttttatttta ttataatgaa ttttgtttgt tgatgtgaaa    480
cattatgcct taagtaatgt taattcttat ttaagttatt gatgttttaa gtttatcttt    540
catggtacta gtgttttta gatacagaga cttggggaaa ttgcttttcc tcttgaacca    600
cagttctacc cctgggatgt tttgagggtc tttgcaagaa tcattaatac aaagaatttt    660
ttttaacatt ccaatgcatt gctaaaatat tattgtggaa atgaatattt tgtaactatt    720
acaccaaata aatatatttt tgtacaaaaa aaaaaaaaaa                          760

<210> SEQ ID NO 44
<211> LENGTH: 92
<212> TYPE: PRT
<213> ORGANISM: Homo sapiens

<400> SEQUENCE: 44

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe

```
            50                  55                  60
Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90

<210> SEQ ID NO 45
<211> LENGTH: 92
<212> TYPE: PRT
<213> ORGANISM: Homo sapiens

<400> SEQUENCE: 45

Met Gln Val Ser Thr Ala Ala Leu Ala Val Leu Leu Cys Thr Met Ala
 1               5                  10                  15

Leu Cys Asn Gln Phe Ser Ala Ser Leu Ala Ala Asp Thr Pro Thr Ala
                 20                  25                  30

Cys Cys Phe Ser Tyr Thr Ser Arg Gln Ile Pro Gln Asn Phe Ile Ala
             35                  40                  45

Asp Tyr Phe Glu Thr Ser Ser Gln Cys Ser Lys Pro Gly Val Ile Phe
         50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90

<210> SEQ ID NO 46
<211> LENGTH: 813
<212> TYPE: DNA
<213> ORGANISM: Artificial Sequence
<220> FEATURE:
<223> OTHER INFORMATION: A non-limiting example of a nucleotide sequence
      that encodes human MIP-1a (cDNA sequence).

<400> SEQUENCE: 46
agctggtttc agacttcaga aggacacggg cagcagacag tggtcagtcc tttcttggct      60
ctgctgacac tcgagcccac attccgtcac ctgctcagaa tcatgcaggt ctccactgct     120
gcccttgctg tcctcctctg caccatggct ctctgcaacc agttctctgc atcacttgct     180
gctgacacgc cgaccgcctg ctgcttcagc tacacctccc ggcagattcc acagaatttc     240
atagctgact acttttgagac gagcagccag tgctccaagc ccggtgtcat cttcctaacc     300
aagcgaagcc ggcaggtctg tgctgacccc agtgaggagt gggtccagaa atatgtcagc     360
gacctggagc tgagtgcctg agggggtccag aagcttcgag gcccagcgac tcggtgggc     420 ccagtgggga ggagcaggag cctgagcctt gggaacatgc gtgtgacctc cacagctacc     480
tcttctatgg actggttgtt gccaaacagc cacactgtgg gactcttctt aacttaaatt     540
ttaatttatt tatactattt agttttttgta atttatttc gatttcacag tgtgtttgtg     600
attgtttgct ctgagagttc ccctgtcccc tccccttcc ctcacaccgc gtctggtgac     660
aaccgagtgg ctgtcatcag cctgtgtagg cagtcatggc accaaagcca ccagactgac     720
aaatgtgtat cggatgcttt tgttcagggc tgtgatcggc ctggggaaat aataaagatg     780
ctcttttaaa aggtaaaaaa aaaaaaaaaa aaa                                   813

<210> SEQ ID NO 47
<211> LENGTH: 92
<212> TYPE: PRT
<213> ORGANISM: Homo sapiens
```

<400> SEQUENCE: 47

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 48
<211> LENGTH: 92
<212> TYPE: PRT
<213> ORGANISM: Homo sapiens

<400> SEQUENCE: 48

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
            20                  25                  30

Ala Cys Cys Phe Ser Tyr Thr Ala Arg Lys Leu Pro Arg Asn Phe Val
        35                  40                  45

Val Asp Tyr Tyr Glu Thr Ser Ser Leu Cys Ser Gln Pro Ala Val Val
    50                  55                  60

Phe Gln Thr Lys Arg Ser Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO 49
<211> LENGTH: 667
<212> TYPE: DNA
<213> ORGANISM: Artificial Sequence
<220> FEATURE:
<223> OTHER INFORMATION: A non-limiting example of a nucleotide sequence
      that encodes human MIP1b (cDNA sequence).

<400> SEQUENCE: 49
agcacaggac acagctgggt tctgaagctt ctgagttctg cagcctcacc tctgagaaaa      60 cctctttttcc accaatacca tgaagctctg cgtgactgtc ctgtctctcc tcatgctagt    120
agctgccttc tgctctccag cgctctcagc accaatgggc tcagaccctc ccaccgcctg    180
ctgcttttct tacaccgcga ggaagcttcc tcgcaacttt gtggtagatt actatgagac    240
cagcagcctc tgctcccagc cagctgtggt attccaaacc aaaagaagca agcaagtctg    300
tgctgatccc agtgaatcct gggtccagga gtacgtgtat gacctggaac tgaactgagc    360
tgctcagaga caggaagtct tcagggaagg tcacctgagc ccggatgctt ctccatgaga    420
cacatctcct ccatactcag gactcctctc cgcagttcct gtcccttctc ttaatttaat    480
cttttttatg tgccgtgtta ttgtattagg tgtcatttcc attatttata ttagtttagc    540

-continued

```
caaaggataa gtgtcccta tggggatggt ccactgtcac tgtttctctg ctgttgcaaa      600
tacatggata acacatttga ttctgtgtgt tttcataata aaactttaaa ataaaatgca      660
gacagtt                                                                667
```

INACTIVATED *BACILLUS COAGULANS* AND USES THEREOF FOR INCREASING PHYSICAL PERFORMANCE

CROSS-REFERENCE TO RELATED APPLICATIONS

This application is a national stage application filed under 35 U.S.C. § 371, of International Patent Application No PCT/US2018/038751, filed on Jun. 21, 2018, which claims the benefit of and priority to U.S. Provisional Application No. 62/522,817, filed on Jun. 21, 2017, the entire contents of which are incorporated herein by reference in their entirety.

INCORPORATION-BY-REFERENCE OF SEQUENCE LISTING

The entire contents of the sequence listing text file named "019374-553001WO_SEQUENCE_LISTING.txt", which was created on Jun. 20, 2018 and is 78,756 bytes in size, are incorporated herein by reference.

BACKGROUND

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. These findings have led to attempts to modify the composition and metabolic activities of the bacterial community through diet, primarily with probiotics, which are live microbial food supplements.

SUMMARY OF THE INVENTION

Provided herein are, inter alia, compositions comprising inactivated, non-viable, and/or dead *Bacillus coagulans* spores, bacteria and/or particles thereof. Preferably, the compositions comprise inactivated, non-viable and/or dead *B. coagulans*, e.g., GBI-30 strain (also referred to as "BC30" "GBI-30, 6086" and "ATCC Designation Number PTA-6086") spores. For example, the inactivated, non-viable, or dead *Bacillus coagulans* bacteria comprise inactivated, non-viable, or dead *Bacillus coagulans* spores, e.g., the bacteria comprises at least 85%, 90%, 95%, 98%, 99% or 100% *Bacillus coagulans* spores. Such inactivated, non-viable, or dead *Bacillus coagulans* spores do not germinate. The inactivated spores do not germinate into vegetative bacterial cells capable of proliferation.

In an aspect, provided herein is a method of increasing a subject's physical performance. In various embodiments, the method comprises administering an effective amount of composition comprising inactivated, non-viable, or dead *Bacillus coagulans* bacteria to the subject. In various embodiments, the inactivated, non-viable, or dead *Bacillus coagulans* bacteria are in the form of inactivated, non-viable, or dead *Bacillus coagulans* spores. In some cases, the inactivated, non-viable, or dead *Bacillus coagulans* bacteria comprise inactivated, non-viable, or dead *Bacillus coagulans* vegetative bacteria.

Subjects that benefit from ingestion of the non-viable spores and/or vegetative *Bacillus coagulans* include those participating in physical activity that results in muscle soreness as well as those identified with or suffering from a disease or disorder associated with muscle pain or muscle wasting, e.g., loss of skeletal muscle mass as a result of sarcopenia, cachexia, and anorexic disorders (protein-energy malnutrition). In certain embodiments, the bacteria are *Bacillus coagulans* GBI-30 (ATCC Designation No. PTA-6086), bacteria. Non-pharmaceutical compositions containing dead, inactivated, non-proliferating, non-germinating *B. coagulans*, e.g., GBI-30 (ATCC Designation Number PTA-6086), described herein are useful as food and/or drink additives, functional foods, or nutritional supplements. A draft denome sequence of GBI-30 is described in Orrú et al., (2014) Genome Announcements, 2(6):1-2, the entire contents of which are incorporated herein by reference. The whole-genome shotgun project associated with Orrú et al., (2014) has been deposited in DDBJ/EMBL/GenBank under the accession number JPSK00000000.1. Non-limiting examples of food and beverage compositions provided herein include tea, coffee, alcoholic beverages, fermented foods and beverages, grain-based compositions, baked compositions, confections, omega-3 fatty acids, dairy compositions, non-dairy milk-like compositions, sports nutrition compositions, and feed for a work animal, a companion animal, livestock, or aquaculture.

In various embodiments, increasing physical performance comprises reducing muscle soreness. In some embodiments, the muscle soreness is post-exercise muscle soreness. In certain embodiments, increasing physical performance comprises increasing physical strength or endurance. In various embodiments, increasing physical performance comprises decreasing post-exercise recovery time. In some embodiments, increasing physical performance comprises increasing muscle mass. In certain embodiments, increasing physical performance comprises increasing lean muscle development, recovery, strength, or repair in the subject.

In various embodiments, the subject desires increased physical performance. In some embodiments, the subject is an athlete, a police officer, or a member of an armed force. In certain embodiments, the subject is a performance animal, a companion animal, or a work animal. In various embodiments, the subject has an injury or arthritis, or has had a stroke. In some embodiments, the subject does not have a respiratory, mucous membrane, skin, or gastrointestinal infection.

In certain embodiments, the effective amount is effective to reduce inflammation in the subject. In various embodiments, the effective amount is effective to increase the level of at least one growth factor in a subject. In some embodiments, the level is the level of the at least one growth factor in a bodily fluid of the subject. In certain embodiments, the bodily fluid is blood, plasma, or serum. In various embodiments, the growth factor increases tissue repair, stem cell differentiation, or stem cell proliferation. In some embodiments, the effective amount is effective to increase the level of granulocyte colony-stimulating factor (G-CSF) or granulocyte macrophage colony-stimulating factor (GM-CSF) in the subject. In certain embodiments, the effective amount is effective to increase the level of interleukin-1 receptor antagonist (IL1RA), interleukin-6 (IL-6), or interleukin-10 (IL-10) in the subject. In various embodiments, the effective amount is effective to increase the level of at least one immune activating cytokine in the subject. In some embodiments, the at least one immune activating cytokine comprises interleukin-1 beta (IL-1β), interleukin-6 (IL-6), interleukin-17A (IL-17A), Tumor Necrosis Factor-α (TNF-α), or interferon gamma (IFNγ). In certain embodiments, the effective amount is effective to increase the level of at least one immune activating chemokine in the subject. In various embodiments, the at least one immune activating chemokine comprises monocyte chemoattractant protein-1 (MCP-1), macrophage inflammatory protein 1-alpha (MIP-1α), or macrophage inflammatory protein-1β (MIP1β).

As used herein, an "inactivated" *Bacillus coagulans* bacterium is a *Bacillus coagulans* bacterium with reduced internal metabolic activity and reproductive ability compared to a counterpart that has not been inactivated. In various embodiments, an inactivated *Bacillus coagulans* bacterium comprises an intact cell wall. In some embodiments, an inactivated *Bacillus coagulans* bacterium comprises an intact cell membrane. In some embodiments, an inactivated *Bacillus coagulans* bacterium comprises a genome that does not have a double strand break. In certain embodiments, an inactivated *Bacillus coagulans* bacterium comprises an inactivated spore. In various embodiments, an inactivated *Bacillus coagulans* bacterium comprises an inactivated vegetative bacterium. In some embodiments, inactivated *Bacillus coagulans* bacteria comprise inactivated spores and inactivated vegetative bacteria.

As used herein, a "non-viable" *Bacillus coagulans* bacterium is a *Bacillus coagulans* bacterium with no reproductive ability. In various embodiments, a non-viable *Bacillus coagulans* bacterium comprises no metabolic activity. In some embodiments, a non-viable *Bacillus coagulans* vegetative bacterium does not consume or metabolize glucose (e.g., is incapable of using glucose for energy or as a carbon source). In certain embodiments, a non-viable *Bacillus coagulans* spore is incapable of germination. In various embodiments, the biomass of non-viable *Bacillus coagulans* bacteria does not change when it is incubated in a *Bacillus coagulans* growth medium. In some embodiments, a non-viable *Bacillus coagulans* bacterium comprises a genome with at least one double strand break. In certain embodiments, a non-viable *Bacillus coagulans* bacterium comprises a non-viable spore. In various embodiments, a non-viable *Bacillus coagulans* bacterium comprises a non-viable vegetative bacterium. In some embodiments, non-viable *Bacillus coagulans* bacteria comprise non-viable spores and non-viable vegetative bacteria.

For example, a "dead" *Bacillus coagulans* bacterium is a *Bacillus coagulans* bacterium that does not have a fully intact cell wall or spore. For example, the cell wall of a dead vegetative *Bacillus coagulans* bacterium may have one or more structural defects (e.g., fractures, holes, voids, perforations, etc.) that permits fluid to flow freely in and out of the cell. In another example, the cell or spore may be a whole dead/non-viable vegetative cell. In this example, the cell is non-viable/non-proliferative, yet remains largely structurally (e.g., in terms of the cell wall or spore structure) intact. In certain embodiments, a dead *Bacillus coagulans* bacterium is a fragment of a *Bacillus coagulans* bacterium that comprises a portion of a *Bacillus coagulans* cell wall that comprises peptidoglycan and/or lipoteichoic acid. In various embodiments, a dead *Bacillus coagulans* bacterium comprises a genome that comprises two or more double strand breaks, and the genome is within a cell wall. In some embodiments, a dead *Bacillus coagulans* bacterium comprises a genome that comprises two or more double strand breaks, and the genome is within a cell wall. In certain embodiments, a dead *Bacillus coagulans* bacterium comprises 1 or more genome fragments that is at least about 100 kilobases in length (e.g., 1, 2, 3, 4, or 5 at least about 200, 300, 400, 500 kilobases in length) within a cell wall. In certain embodiments, a dead *Bacillus coagulans* bacterium comprises a dead spore. In various embodiments, a dead *Bacillus coagulans* bacterium comprises a dead vegetative bacterium. In some embodiments, dead *Bacillus coagulans* bacteria comprise dead spores and dead vegetative bacteria.

In various embodiments, inactivated, non-viable, or dead *Bacillus coagulans* bacteria and/or particles retain the presence of undamaged lipoteichoic acid. For example, the lipoteichoic acid comprises immune-activating activity. In certain embodiments, the lipoteichoic acid has the same chemical structure as in corresponding viable *Bacillus coagulans* bacteria.

Also provided are methods of administering such inactivated, non-viable, or dead *Bacillus coagulans* bacteria, particles (e.g., comprising inactivated, non-viable, and/or dead *Bacillus coagulans* bacteria), and compounds (such as lipoteichoic acid or peptidoglycan), e.g., to treat injuries, reduce inflammation, promote tissue repair, and improve athletic performance. In various embodiments, an inactivated, non-viable, or dead *Bacillus coagulans* bacterium, particle, or compound increases the level of at least one growth factor in a subject (e.g., when administered in an effective amount). In some embodiments, the growth factor is an immune-activating or anti-inflammatory growth factor. In certain embodiments, the growth factor is a compound (e.g., a protein or peptide) that increases tissue repair, stem cell differentiation, or stem cell proliferation. In various embodiments, an inactivated, non-viable, or dead *Bacillus coagulans* bacterium, a particle, or a compound increases the level of at least one immune activating cytokine in the subject. In some embodiments, the at least one immune activating cytokine comprises interleukin-1 beta (IL-1β), interleukin-6 (IL-6), interleukin-17A (IL-17A), Tumor Necrosis Factor-α (TNF-α), or interferon gamma (IFNγ). In certain embodiments, an inactivated, non-viable, or dead *Bacillus coagulans* bacterium, a particle, or a compound increases the level of at least one immune activating chemokine in the subject. In various embodiments, the at least one immune activating chemokine comprises monocyte chemoattractant protein-1 (MCP-1), macrophage inflammatory protein 1-alpha (MIP-1α), or macrophage inflammatory protein-1β (MIP1β). In some embodiments, an inactivated, non-viable, or dead *Bacillus coagulans* bacterium, a particle, or a compound increases at least one anti-inflammatory cytokine in the subject. In certain embodiments, the at least one anti-inflammatory cytokine comprises interleukin-1 receptor antagonist (IL-1RA) or interleukin-10 (IL-10). In various embodiments, an inactivated, non-viable, or dead *Bacillus coagulans* bacterium, a particle, or a compound increases the level of interleukin-4 (IL-4), interleukin-7 (IL-7), interleukin-8 (IL-8), interleukin-9 (IL-9), or interleukin-12 (IL12p70). In some embodiments, the level is in a bodily fluid, such as blood, plasma, serum, urine, sweat, sputum, saliva, or tears.

In an aspect, provided herein is a composition comprising inactivated, non-viable, or dead *Bacillus coagulans* bacteria and/or particles comprising such bacteria. In various embodiments, the inactivated, non-viable, or dead *Bacillus coagulans* bacteria and/or particles are present in an amount that is effective to increase the level of at least one growth factor in a subject. In some embodiments, the at least one growth factor is granulocyte colony-stimulating factor (G-CSF) and/or granulocyte macrophage colony-stimulating factor (GM-CSF). In certain embodiments, composition is formulated for oral administration. In some embodiments, the composition is formulated for nasal, topical (e.g., to a mucus membrane and/or to the skin), intraperitoneal, or intravenous administration. In various embodiments, the effective amount is also effective to increase the level of interleukin-1 receptor antagonist (IL1RA), interleukin-6

(IL-6), or interleukin-10 (IL-10) in the subject. In certain embodiments, the level is the level of the at least one growth factor in a bodily fluid of the subject (such as blood, plasma, serum, sweat, saliva, sputum, mucus, tears, or urine).

In various embodiments, the inactivated, non-viable, or dead *Bacillus coagulans* bacteria (or particles comprising such bacteria) comprise inactivated, non-viable, or dead *Bacillus coagulans* vegetative bacteria. In certain embodiments, the inactivated, non-viable, or dead *Bacillus coagulans* bacteria or particles comprise inactivated, non-viable, or dead *Bacillus coagulans* spores. In some embodiments, the inactivated, non-viable, or dead *Bacillus coagulans* bacteria or particles comprise inactivated, non-viable, or dead *Bacillus coagulans* vegetative bacteria and spores. In certain embodiments, the inactivated, non-viable, and/or dead *Bacillus coagulans* bacteria (or particles comprising such bacteria) are dried, e.g., contain les than about 10%, 5%, 1%, 0.1%, 0.01%, 0.001%, 0.0001%, or 0.00001% water moisture by weight. In various embodiments, the inactivated, non-viable, and/or dead *Bacillus coagulans* bacteria (or particles comprising such bacteria) have a water activity of less than about 5, 3, 4, 2, 1.5, 1, 0.75, 0.5, 0.25, or 0.1. As used herein, the term "water activity" is the vapor pressure of water in a substance (e.g. an a composition such as particles comprising inactivated, non-viable, and/or dead *Bacillus coagulans*), divided by the vapor pressure of distilled water at the same temperature. Water activity is often represented by the mathematical equation $a_w = p/p0$, where p is the vapor pressure of water in the substance, and p0 is the vapor pressure of distilled water at the same temperature. Using this particular definition, distilled water has a water activity of 1. The water activities expressed herein are at a temperature of 25° C.

In certain embodiments, the composition further comprises a β-glucan.

In various embodiments, the composition further comprises an excipient or carrier.

In some embodiments, the composition further comprises maltodextrin, inulin, inositol, trehalose, microcrystalline cellulose (MCC), calcium lactate, magnesium stearate, fructo-oligosaccharide (FOS), or gluco-oligosaccharide (GOS).

In certain embodiments, the inactivated, non-viable, or dead *Bacillus coagulans* bacteria have been dried, e.g., lyophilized. In some embodiments, particles comprising inactivated, non-viable, or dead *Bacillus coagulans* bacteria may be combined with an aqueous solution prior to administration to a human or non-human animal subject. In certain embodiments, the inactivated, non-viable, or dead *Bacillus coagulans* bacteria have been lyophilized and then combined with an aqueous solution.

In various embodiments, the composition further comprises a surfactant or an emulsifier. In some embodiments, the surfactant comprises polysorbate 20 and/or polysorbate 80. Additional non-limiting examples of surfactants include lecithin, monoglycerides, sorbitan esters, ethoxylates of sorbitan esters, sucrose esters, glycolipids, fatty alcohols, fatty acids, benzalkonium chloride, cetylpyridinium chloride, sodium dodecyl benzenesulfonate, polyethoxylated octyl phenol, N-dodecyl piridinium chloride, lauryl monoethanol, sorbitan monoester, dimethyl ether of tetradecyl phosphonic, glycerol diester, dodecyl betaine, anionic surfactants, cationic surfactants, nonionic surfactants, zwitterionic surfactants, and gemini surfactants.

In certain embodiments, the composition comprises a food or beverage composition. In various embodiments, the composition comprises tea, coffee, and/or an alcoholic beverage. In some embodiments, the composition comprises a fermented food or beverage. In certain embodiments, the composition comprises a grain-based composition. In various embodiments, the composition comprises a baked composition. In some embodiments, the composition comprises a confection. In certain embodiments, the composition comprises an omega-3 fatty acid. In various embodiments, the composition comprises a dairy composition. In some embodiments, the composition comprises a non-dairy milk-like composition. In certain embodiments, the composition comprises a sports nutrition composition. In various embodiments, the composition comprises animal feed. In some embodiments, the animal feed comprises feed for a work animal, a companion animal, livestock, or aquaculture.

Compositions containing (e.g., comprising, consisting essentially of, or consisting of) *Bacillus coagulans* peptidoglycan and/or lipoteichoic acid are also provided. In certain embodiments, the peptidoglycan and/or lipoteichoic acid is present in an amount that is effective to increase the level of at least one growth factor in a subject. In various embodiments, the composition comprises both peptidoglycan and lipoteichoic acid. In some embodiments, the peptidoglycan and/or lipoteichoic acid is purified peptidoglycan and/or lipoteichoic acid. In certain embodiments, the composition does not comprise a viable *Bacillus coagulans* bacterium. In various embodiments, the composition further comprises a β-glucan. β-glucans comprise a group of β-D-glucose polysaccharides naturally occurring in the cell walls of cereals, bacteria, and fungi, with significantly differing physicochemical properties dependent on source. Typically, β-glucans form a linear backbone with 1-3 β-glycosidic bonds but vary with respect to molecular mass, solubility, viscosity, branching structure, and gelation properties, causing diverse physiological effects in animals.

In some embodiments, the composition comprises a food or beverage composition. In certain embodiments, the composition comprises tea, coffee, and/or an alcoholic beverage. In various embodiments, the composition comprises a fermented food or beverage. In some embodiments, the composition comprises a grain-based composition. In certain embodiments, the composition comprises a baked composition. In various embodiments, the composition comprises a confection. In some embodiments, the composition comprises an omega-3 fatty acid. Omega-3 fatty acids (also called ω-3 fatty acids or n-3 fatty acids) are polyunsaturated fatty acids with a double bond (C=C) at the third carbon atom from the end of the carbon chain. Non-limiting examples of omega-3 fatty acids include hexadecatrienoic acid (HTA), α-Linolenic acid (ALA), stearidonic acid (SDA), eicosatrienoic acid (ETE), eicosatetraenoic acid (ETA), eicosapentaenoic acid (EPA), heneicosapentaenoic acid (HPA), docosapentaenoic acid (DPA), docosahexaenoic acid (DHA), tetracosapentaenoic acid, and tetracosahexaenoic acid. In certain embodiments, the composition comprises a dairy composition. In various embodiments, the composition comprises a non-dairy milk-like composition. In some embodiments, the composition comprises a sports nutrition composition. In certain embodiments, the composition comprises animal feed.

Also provided herein is a method of increasing tissue repair in a subject. In various embodiments, tissue repair comprises cell (e.g., muscle cell) growth and/or division within the tissue. In certain embodiments, the method comprises administering an effective amount of inactivated, non-viable, or dead *Bacillus coagulans* bacteria or particles (e.g., a composition inactivated, non-viable, or dead *Bacillus coagulans* bacteria or particles comprising such bacteria) to the subject. In some embodiments, the method comprises administering an effective amount of *Bacillus coagulans* peptidoglycan and/or lipoteichoic acid to the subject.

In various embodiments, the subject has an injury. In some embodiments, the injury comprises tendonitis, a sprain, a muscle tear, bruised tissue (such as skin or muscle), a laceration, a wound, a scrape, or bursitis.

In some embodiments, the subject has traumatic brain injury.

In certain embodiments, the subject has had a stroke.

In various embodiments, the subject has arthritis. In some embodiments, the arthritis is osteoarthritis. In certain embodiments, the arthritis is rheumatoid arthritis.

In various embodiments, the subject does not have an infection (such as a respiratory, mucous membrane, skin, or gastrointestinal infection).

In some embodiments, inflammation (e.g., at the site of an injury) is reduced in the subject. In certain embodiments, the amount of a growth factor is increased in the subject. In various embodiments the level of G-CSF and/or GM-CSF increases in the subject. In some embodiments, the level of G-CSF increases and the level of GM-CSF increases in the subject. In certain embodiments the level of GM-CSF decreases in the subject. In some embodiments, the level of an anti-inflammatory or tolerizing cytokine increases in the subject. In certain embodiments, the level of IL1RA, IL-6, and/or IL-10 increases in the subject.

In various embodiments, a method of increasing tissue repair in a subject increases muscle tissue repair.

In an aspect, provided herein is a method of increasing a subject's physical performance. In some embodiments, the method includes administering an effective amount of inactivated, non-viable, or dead *Bacillus coagulans* bacteria or particles (e.g., a composition comprising inactivated, non-viable, or dead *Bacillus coagulans* bacteria or particles comprising such bacteria). In various embodiments, the method comprises administering an effective amount of *Bacillus coagulans* peptidoglycan and/or lipoteichoic acid to the subject.

In some embodiments, increasing physical performance comprises reducing muscle soreness. In certain embodiments, the muscle soreness is post-exercise muscle soreness.

In various embodiments, increasing physical performance comprises increasing physical strength or endurance.

In some embodiments, increasing physical performance comprises decreasing post-exercise recovery time.

In certain embodiments, increasing physical performance comprises increasing muscle mass.

In various embodiments, the subject desires increased physical performance. In some embodiments, the subject is an athlete (e.g., a runner, bicyclist, baseball player, soccer player, football player, hockey player, basketball player, or cricket player). In certain embodiments, the subject is a law enforcement officer. In various embodiments, the subject is a firefighter. In some embodiments, the subject is an astronaut. In certain embodiments, the subject is a construction worker. In various embodiments, the subject is a member of an armed force (such as a soldier, a marine, a sailor, or a pilot).

In some embodiments, the animal is a performance animal (such as a military dog, a police dog, a race dog, a show dog, a military horse, a police horse, a race horse, a polo horse, or a show horse), a companion animal (such as a dog or a cat), or a work animal (such as a yak, camel, horse, ox, or yak). In certain embodiments, the subject is a reptile, amphibian, bird, or mammal. In various embodiments, the subject is a primate (such as an ape, monkey, gorilla, orangutan, chimpanzee, or human). In some embodiments, the subject is a parrot, chicken, goose, duck, dog, cat, rabbit, pig, or horse. In certain embodiments, the subject is a ruminant such as a cow, sheep, goat, buffalo, yak, deer, elk, giraffe, or camel. In various embodiments, the animal is a pseudoruminant, such as a hippopotamus. Ruminants have four-chambered stomachs whereas pseudoruminants have three-chambered stomachs. In some embodiments, the animal is a performance animal such as a military dog, a police dog, a race dog, a show dog, a military horse, a police horse, a race horse, a polo horse, or a show horse.

Included herein is a method of increasing lean muscle development, recovery, strength, or repair in a subject. In various embodiments, the method comprises administering an effective amount of inactivated, non-viable, or dead *Bacillus coagulans* bacteria or particles (e.g., a composition comprising inactivated, non-viable, or dead *Bacillus coagulans* bacteria or particles comprising such bacteria) to the subject. In some embodiments, the method comprises administering an effective amount of *Bacillus coagulans* peptidoglycan and/or lipoteichoic acid to the subject.

In various embodiments, a subject does not have (e.g., has not been diagnosed with) a gastrointestinal disease or an inflammatory bowel condition. In some embodiments, a subject does not have (e.g., has not been diagnosed with) an infection (e.g., a viral or bacterial infection).

In certain embodiments, the subject does not have a viral respiratory infection. In various embodiments, the subject does not have a gastrointestinal infection.

In some embodiments, the inactivated, non-viable, or dead *Bacillus coagulans* bacteria or particles comprise between about 0.000001% to about 10% by weight of the composition. In certain embodiments, a composition provided herein may be about 0.000001%, 0.00001%, 0.0001%, 0.001%, 0.01%, 0.1%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% inactivated, non-viable, or dead *Bacillus coagulans* bacteria or particles by weight. In various embodiments, a composition provided herein may be at least 0.000001%, 0.00001%, 0.0001%, 0.001%, 0.01%, 0.1%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% inactivated, non-viable, or dead *Bacillus coagulans* bacteria or particles by weight. In some embodiments, a composition provided herein may be less than 0.000001%, 0.00001%, 0.0001%, 0.001%, 0.01%, 0.1%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% dead or inactivated *Bacillus coagulans* bacteria by weight. In certain embodiments, a composition comprises at least 0.000001%, 0.00001%, 0.0001%, 0.001%, 0.01%, 0.1% but less than 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% inactivated, non-viable, or dead *Bacillus coagulans* bacteria or particles by weight.

In various embodiments, the number of particles in a composition is about $1\times10^3$-$1\times10^{20}$, $1\times10^3$-$1\times10^9$, $1\times10^3$-$1\times10^6$, $1\times10^6$-$1\times10^9$, $1\times10^6$-$1\times10^{20}$, $1\times10^6$-$1\times10^{15}$, $1\times10^6$-$1\times10^{12}$, $1\times10^8$-$1\times10^{17}$, $1\times10^{10}$-$1\times10^{20}$, $1\times10^3$-$1\times10^{10}$, $1\times10^5$-$1\times10^{10}$, $1\times10^5$-$1\times10^{15}$, $1\times10^1$-$1\times10^{15}$, $1\times10^{14}$-$1\times10^{16}$, or about, at least, or less than 5, 10, 50, 100, 500, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$ $1\times10^{15}$, $1\times10^{16}$, $1\times10^{17}$, $1\times10^{18}$, $1\times10^{19}$, or $1\times10^{20}$ particles. In some embodiments, the number of particles in a composition is about $1\times10^3$-$1\times10^{20}$, $1\times10^3$-$1\times10^9$, $1\times10^3$-$1\times10^6$, $1\times10^6$-$1\times10^9$, $1\times10^6$-$1\times10^{20}$, $1\times10^6$-$1\times10^{15}$, $1\times10^6$-$1\times10^{12}$, $1\times10^8$-$1\times10^{17}$, $1\times10^{10}$-$1\times10^{20}$, $1\times10^3$-$1\times10^{10}$, $1\times10^5$-$1\times10^{10}$, $1\times10^5$-$1\times10^{15}$, $1 \times 10^{10}$-$1 \times 10^{15}$, $1 \times 10^{14}$-$1 \times 10^{16}$ per gram or about, at least, or less than 5, 10, 50, 100, 500, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, or $1 \times 10^{20}$ particles per gram. In certain embodiments, the number of particles in a composition is about $1 \times 10^9$-$1 \times 10^{11}$ per gram or about $1 \times 10^9$, $1.5 \times 10^9$, $2 \times 10^9$, $2.5 \times 10^9$, $3 \times 10^9$, $3.5 \times 10^9$, $4 \times 10^9$, $4.5 \times 10^9$, $5 \times 10^9$, $5.5 \times 10^9$, $6 \times 10^9$, $6.5 \times 10^9$, $7 \times 10^9$, $7.5 \times 10^9$, $8 \times 10^9$, $8.5 \times 10^9$, $9 \times 10^9$, $9.5 \times 10^9$, $1 \times 10^{10}$, $1.5 \times 10^{10}$, $2 \times 10^{10}$, $2.5 \times 10^{10}$, $3 \times 10^{10}$, $3.5 \times 10^{10}$, $4 \times 10^{10}$, $4.5 \times 10^{10}$, $5 \times 10^{10}$, $5.5 \times 10^{10}$, $6 \times 10^{10}$, $6.5 \times 10^{10}$, $7 \times 10^{10}$, $7.5 \times 10^{10}$, $8 \times 10^{10}$, $8.5 \times 10^{10}$, $9 \times 10^{10}$, $9.5 \times 10^{10}$, or $1 \times 10^{11}$, particles per gram.

In various embodiments, *Bacillus coagulans* bacteria are isolated or purified (e.g., from media or supernatant in a growth culture) before being deactivated (e.g., killed). In certain embodiments, *Bacillus coagul 10-500 µm, 50-100 µm, 50-200 µm, 50-300 µm, 50-400 µm, 50-500 µm, 100-250 µm, 100-500 µm, 150-450 µm, 150-300 µm, 250-500 µm, 500-750 µm, or 500-1000 µm); comprising an average diameter of about 1-5 µm, 1-10 µm, 5-50 µm, 5-100 µm, 5-25 µm, 10-100 µm, or 1-1000 µm (e.g., about 1 µm, about 2.5 µm, about 5 µm, about 7.5 µm, about 10 µm, about 15 µm, about 20 µm, about 25 µm, about 30 µm, about 35 µm, about 40 µm, about 45 µm, about 50 µm, about 75 µm, about 100 µm, about 150 µm, about 200 µm, about 250 µm, about 300 µm, about 350 µm, about 400 µm, about 450 µm, about 500 µm, about 600 µm, about 700 µm, about 800 µm, about 900 µm, about 1000 µm, 10-1000 µm, 10-100 µm, 10-500 µm, 50-100 µm, 50-200 µm, 50-300 µm, 50-400 µm, 50-500 µm, 100-250 µm, 100-500 µm, 150-450 µm, 150-300 µm, 250-500 µm, 500-750 µm, or 500-1000 µm; and/or having a total volume of about 10-10000 mm$^3$ (e.g., about 10 mm$^3$, about 25 mm$^3$, about 50 mm$^3$, about 75 mm$^3$, about 100 mm$^3$, about 150 mm$^3$, about 200 mm$^3$, about 250 mm$^3$, about 300 mm$^3$, about 350 mm$^3$, about 400 mm$^3$, about 450 mm$^3$, about 500 mm$^3$, about 600 mm$^3$, about 700 mm$^3$, about 800 mm$^3$, about 900 mm$^3$, about 1000 mm$^3$, about 2500 mm$^3$, about 7000 mm$^3$, about 7500 mm$^3$, about 10000 mm$^3$, 100-10000 mm$^3$, 100-1000 mm$^3$, 100-5000 mm$^3$, 500-1000 mm$^3$, 500-2000 mm$^3$, 500-3000 mm$^3$, 500-4000 mm$^3$, 500-5000 mm$^3$, 100-250 mm$^3$, 100-500 mm$^3$, 150-450 mm$^3$, 150-300 mm$^3$, 250-500 mm$^3$, 500-750 mm$^3$, 500-1000 mm$^3$, 1000-2500 mm$^3$, 1000-5000 mm$^3$, 1500-4500 mm$^3$, 1500-3000 mm$^3$, 2500-5000 mm$^3$, 5000-7500 mm$^3$, or 5000-10000 mm$^3$.

In various embodiments, a composition or method provided herein comprises a component of a dead *Bacillus coagulans* cell wall (e.g., lipoteichoic acid and/or peptidoglycan). In certain embodiments, the component is purified.

In some embodiments, killing a *Bacillus coagulans* bacterium comprises exposing the *Bacillus coagulans* bacterium to heat, e.g., under wet (e.g., in an aqueous solution or in the presence of steam) or dry conditions. In certain embodiments, killing the *Bacillus coagulans* bacterium comprises exposing the *Bacillus coagulans* bacterium to pressure. In various embodiments, killing the *Bacillus coagulans* bacterium comprises exposing the *Bacillus coagulans* bacterium to both heat and pressure. In certain embodiments, killing the *Bacillus coagulans* bacterium comprises applying pressure to the *Bacillus coagulans* bacterium with a French press.

In some embodiments, vegetative *Bacillus coagulans* bacterial cells are killed by repeated freeze-thaw cycles (e.g., freezing than thawing at least about 2, 3, 4, 5, 6, 7, 8, 9, or 10 times). In certain embodiments, *Bacillus coagulans* bacteria (e.g., vegetative bacteria and/or spores) are killed by bead milling. In various embodiments, bead milling comprises vortexing the bacteria in the presence of beads. In some embodiments, the beads have a diameter of about 50 µm, 100 µm, 150 µm, 200 µm, 250 µm, 300 µm, 350 µm, 400 µm, 450 µm, 500 µm, 20-250 µm, 100-300 µm, 50-500 µm, 50-750 µm, 500-1000 µm, or 750-1000 µm. In certain embodiments, the beads are low-protein-binding beads. In various embodiments, the beads comprise zirconium. In some embodiments, the beads are zirconium beads. In certain embodiments, killing the *Bacillus coagulans* bacteria comprises freeze-thaw cycles and bead milling. In various embodiments, killing the *Bacillus coagulans* does not comprise bead milling. In some embodiments, killing the *Bacillus coagulans* bacteria comprises drying, e.g. lyophilizing, vegetative bacteria. In certain embodiments, killing the *Bacillus coagulans* bacteria comprises lyophilizing vegetative bacteria and then milling the lyophilized bacteria (e.g., with beads). In some embodiments, killing the *Bacillus coagulans* bacteria comprises sonication.

In certain embodiments, *Bacillus coagulans* bacteria are cultured in a fermentor prior to being inactivated (e.g., killed). In various embodiments, *Bacillus coagulans* bacteria are centrifuged (e.g., to form a pellet of *Bacillus coagulans* bacteria) from culture media (e.g., from a fermentor or flask).

In various embodiments, the *Bacillus coagulans* bacteria are killed as part of the normal manufacturing process of an edible composition. For example, a pasteurization technique that kills all or substantially all (such as about or at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%) *Bacillus coagulans* bacteria (e.g., vegetative cells and/or spores) in a composition may be used. In some embodiments, foods that are pre-cooked during the manufacturing process (such as baked compositions, meat products such as hamburger patties, pre-cooked frozen products, etc.) are cooked at a temperature and/or pressure that kills all or substantially all (such as about or at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%) *Bacillus coagulans* vegetative cells and/or spores in a composition. A non-limiting example with respect to beverage compositions includes beverage compositions that are heated (e.g., boiled and/or steeped) for an amount of time that is sufficient to kill all or substantially all (such as about or at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%) *Bacillus coagulans* vegetative cells and/or spores in the composition. Non-limiting examples of beverage compositions include hot beverage compositions such as aleberry, anijsmelk, apple cider, asiático, atoly, bajigur, bandrek, blackberry demitasse, blue blazers, bouillon, butter tea, caudle, coffee, hot egg drinks, espresso, hot ginger cordials, greyana rakiya, grog, tea, hot buttered rum, hot chocolate, hot toddies, Irish coffee, hot lemonade, malted milk, mate cocido, mulled wine, posset, postum, sake, salep, sassafras tea, smoking bishop, hot sodas, spiced punch, and wedang jahe.

In some embodiments, the genomes of the inactivated, non-viable, or dead *Bacillus coagulans* bacteria are intact. In certain embodiments, the inactivated, non-viable, or dead *Bacillus coagulans* bacteria can be identified as containing *Bacillus coagulans* genomic DNA, e.g., by sequencing, polymerase chain reaction, microarray analysis, and/or probes. In various embodiments, at least 1 or more 10, 20, 30, 40, 50, 60, 70, 80, 90, 100, 150, 200, 250, 300, 350, 400, 450, 500, 750, 1000, 1500, 2000, 2500, or 3000 kilobase fragment or portion of the *Bacillus coagulans* genome is present within inactivated, non-viable, or dead *Bacillus coagulans* vegetative bacteria and/or spores.

In certain embodiments, a composition provided herein is present on the exterior surface of an edible composition. For example the composition may be present as a coating on the exterior surface of the edible composition. In some embodiments, the composition completely surrounds the edible composition. In various embodiments, the edible composition comprises a food composition or a supplement composition. In some embodiments, the edible composition comprises a food composition. In certain embodiments, an edible composition may be edible for and/or fed to a human or a non-human animal (e.g., a reptile, amphibian, bird, or mammal) such as a primate (e.g., an ape, monkey, gorilla, orangutan, chimpanzee, or human) or other animal (e.g., a parrot, chicken, goose, duck, dog, cat, rabbit, pig, or horse, or a ruminant such as a cow, sheep, goat, buffalo, yak, deer, elk, giraffe, or camel). In some embodiments, the animal is a pseudoruminant, such as a hippopotamus. Ruminants have four-chambered stomachs whereas pseudoruminants have three-chambered stomachs. In some embodiments, the animal is a performance animal such as a military dog, a police dog, a race dog, a show dog, a military horse, a police horse, a race horse, a polo horse, or a show horse.

In some embodiments, the inactivated, non-viable, or dead *Bacillus coagulans* bacteria are in the form of particles of inactivated, non-viable, or dead *Bacillus coagulans* bacteria. In certain embodiments, a composition provided herein is in the form of or comprises a particle or particles (e.g., at least about 1, 5, 10, 50, 100, 500, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, or $1 \times 10^{20}$ particles, e.g., total or per gram). In various embodiments, at least 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles are 25 mesh (i.e., small enough to pass through a sieve with a nominal opening of 707 μm), 30 mesh (i.e., small enough to pass through a sieve with a nominal opening of 595 μm), 35 mesh (i.e., small enough to pass through a sieve with a nominal opening of 500 μm), 40 mesh (i.e., small enough to pass through a sieve with a nominal opening of 420 μm), 45 mesh (i.e., small enough to pass through a sieve with a nominal opening of 354 μm), or 50 mesh (i.e., small enough to pass through a sieve with a nominal opening of 297 μm) and at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% % of the particles are 70 mesh (i.e., small enough to pass through a sieve with a nominal opening of 210 μm), 80 mesh (i.e., small enough to pass through a sieve with a nominal opening of 177 μm), or 100 mesh (i.e., small enough to pass through a sieve with a nominal opening of 149 μm). In some embodiments, at least 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles are have at least one dimension that is less than about 707 μm, 595 μm, 500 μm, 420 μm, 354 μm, or 297 μm and at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles have at least one dimension that is less than about 210 μm, 177 μm, or 149 μm. In certain embodiments, at least 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles are have at least two dimensions that are less than about 707 μm, 595 μm, 500 μm, 420 μm, 354 μm, or 297 μm and at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles have at least two dimensions that are less than about 210 μm, 177 μm, or 149 μm. In various embodiments, at least 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles have no dimension that is greater than about 707 μm, 595 μm, 500 μm, 420 μm, 354 μm, or 297 μm and at least 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or 100% of the particles have no dimension that is greater than about 210 μm, 177 μm, or 149 μm.

In certain embodiments, the particles are present within a composition (such as an edible composition). In various embodiments, the particle are present on the exterior surface of composition (such as an edible composition). In some embodiments, particles are present within and on the exterior surface of composition (such as an edible composition).

The term "particle," as used herein, refers to a discrete body. Particles may be amorphous, or may take a variety of shapes, including round, oblong, square, etc. Non-limiting examples of particles include crystals, grains, beads, amorphous bodies, and spheres. Certain embodiments of the present subject matter include particles of various sizes, e.g., comprising an approximate maximum width or diameter of about 1-5 μm, 1-10 μm, 5-50 μm, 5-100 μm, 5-25 μm, 10-100 μm, or 1-1000 μm (e.g., about 1 μm, about 2.5 μm, about 5 μm, about 7.5 μm, about 10 μm, about 15 μm, about 20 μm, about 25 μm, about 30 μm, about 35 μm, about 40 μm, about 45 μm, about 50 μm, about 75 μm, about 100 μm, about 150 μm, about 200 μm, about 250 μm, about 300 μm, about 350 μm, about 400 μm, about 450 μm, about 500 μm, about 600 μm, about 700 μm, about 800 μm, about 900 μm, about 1000 μm, 10-1000 μm, 10-100 μm, 10-500 μm, 50-100 μm, 50-200 μm, 50-300 μm, 50-400 μm, 50-500 μm, 100-250 μm, 100-500 μm, 150-450 μm, 150-300 μm, 250-500 μm, 500-750 μm, or 500-1000 μm); comprising an average diameter of about 1-5 μm, 1-10 μm, 5-50 μm, 5-100 μm, 5-25 μm, 10-100 μm, or 1-1000 μm (e.g., about 1 μm, about 2.5 μm, about 5 μm, about 7.5 μm, about 10 μm, about 15 μm, about 20 m, about 25 μm, about 30 μm, about 35 μm, about 40 μm, about 45 μm, about 50 μm, about 75 μm, about 100 μm, about 150 μm, about 200 μm, about 250 μm, about 300 μm, about 350 μm, about 400 lam, about 450 μm, about 500 μm, about 600 μm, about 700 μm, about 800 μm, about 900 μm, about 1000 μm, 10-1000 μm, 10-100 μm, 10-500 μm, 50-100 μm, 50-200 μm, 50-300 μm, 50-400 μm, 50-500 μm, 100-250 μm, 100-500 μm, 150-450 μm, 150-300 μm, 250-500 μm, 500-750 μm, or 500-1000 μm; and/or having a total volume of about 10-10000 mm³ (e.g., about 10 mm³, about 25 mm³, about 50 mm³, about 75 mm³, about 100 mm³, about 150 mm³, about 200 mm³, about 250 mm³, about 300 mm³, about 350 mm³, about 400 mm³, about 450 mm³, about 500 mm³, about 600 mm³, about 700 mm³, about 800 mm³, about 900 mm³, about 1000 mm³, about 2500 mm³, about 7000 mm³, about 7500 mm³, about 10000 mm³, 100-10000 mm³, 100-1000 mm³, 100-5000 mm³, 500-1000 mm³, 500-2000 mm³, 500-3000 mm³, 500-4000 mm³, 500-5000 mm³, 100-250 mm³, 100-500 mm³, 150-450 mm³, 150-300 mm³, 250-500 mm³, 500-750 mm³, 500-1000 mm³, 1000-2500 mm³, 1000-5000 mm³, 1500-4500 mm³, 1500-3000 mm³, 2500-5000 mm³, 5000-7500 mm³, or 5000-10000 mm³. In some embodiments, a particle comprises at least about 1, 5, 10, 50, 100, 500, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, $1 \times 10^{19}$, or $1 \times 10^{20}$ inactivated, non-viable, or dead *Bacillus coagulans* vegetative bacteria and/or spores, or about $1 \times 10^3$ to about $1 \times 10^5$, about $1 \times 10^3$ to about $1 \times 10^6$, about $1 \times 10^3$ to about $1 \times 10^7$, about $1 \times 10^3$ to about $1 \times 10^8$, about $1 \times 10^3$ to about $1 \times 10^9$, about $1 \times 10^3$ to about $1 \times 10^{10}$, about $1 \times 10^3$ to about $1 \times 10^{11}$, about $1 \times 10^3$ to about $1 \times 10^{12}$, about $1 \times 10^3$ to about $1 \times 10^{13}$, about $1 \times 10^3$ to about $1 \times 10^{14}$, $1 \times 10^6$ to about $1 \times 10^5$, about $1 \times 10^6$ to about $1 \times 10^6$, or about $1 \times 10^6$ to about $1 \times 10^7$, about $1 \times 10^6$ to about $1 \times 10^8$, about $1 \times 10^6$ to about $1 \times 10^9$, about $1 \times 10^6$ to about $1 \times 10^{10}$, about $1 \times 10^6$ to about $1 \times 10^{11}$, about $1 \times 10^6$ to about $1 \times 10^{12}$, about $1 \times 10^6$ to about $1 \times 10^{13}$, about $1 \times 10^6$ to about $1 \times 10^{14}$, $1 \times 10^3$-$1 \times 10^{20}$, $1 \times 10^3$-$1 \times 10^9$, $1 \times 10^3$-$1 \times 10^6$, $1 \times 10^6$-$1 \times 10^9$, $1 \times 10^6$-$1 \times 10^{20}$, $1 \times 10^6$-$1 \times 10^{15}$, $1 \times 10^6$-$1 \times 10^{12}$, $1 \times 10^8$-$1 \times 10^{17}$, $1 \times 10^{10}$-$1 \times 10^{20}$, $1 \times 10^3$-$1 \times 10^{10}$, $1 \times 10^5$-$1 \times 10^{10}$, $1 \times 10^5$-$1 \times 10^{15}$, $1 \times 10^{10}$-$1 \times 10^{15}$, $1 \times 10^{14}$-$1 \times 10^{16}$, or about, at least, or less than 5, 10, 50, 100, 500, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$ $1\times10^{15}$, $1\times10^{16}$, $1\times10^{17}$, $1\times10^{18}$, $1\times10^{19}$, or $1\times10^{20}$ inactivated, non-viable, or dead *Bacillus coagulans* vegetative bacteria and/or spores.

In certain embodiments, a composition comprises at least about 1, 5, 10, 50, 100, 500, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, or $1\times10^{20}$ inactivated, non-viable, or dead *Bacillus coagulans* vegetative bacteria and/or spores, or about $1\times10^3$ to about $1\times10^5$, about $1\times10^3$ to about $1\times10^6$, about $1\times10^3$ to about $1\times10^7$, about $1\times10^3$ to about $1\times10^8$, about $1\times10^3$ to about $1\times10^9$, about $1\times10^3$ to about $1\times10^{10}$, about $1\times10^3$ to about $1\times10^{11}$, about $1\times10^3$ to about $1\times10^{12}$, about $1\times10^3$ to about $1\times10^{13}$, about $1\times10^3$ to about $1\times10^{14}$, $1\times10^6$ to about $1\times10^5$, about $1\times10^6$ to about $1\times10^6$, or about $1\times10^6$ to about $1\times10^7$, about $1\times10^6$ to about $1\times10^8$, about $1\times10^6$ to about $1\times10^9$, about $1\times10^6$ to about $1\times10^{10}$, about $1\times10^6$ to about $1\times10^{11}$, about $1\times10^6$ to about $1\times10^{12}$, about $1\times10^6$ to about $1\times10^{13}$, about $1\times10^6$ to about $1\times10^{14}$-$1\times10^3$-$1\times10^{20}$, $1\times10^3$-$1\times10^9$, $1\times10^3$-$1\times10^6$, $1\times10^6$-$1\times10^9$, $1\times10^6$-$1\times10^{20}$, $1\times10^6$-$1\times10^{15}$, $1\times10^6$-$1\times10^{12}$, $1\times10$-$1\times10^{17}$, $1\times10^{10}$- $1\times10^{20}$, $1\times10^3$-$1\times10^{10}$, $1\times10^5$-$1\times10^{10}$, $1\times10^5$-$1\times10^{15}$, $1\times10^{10}$-$1\times10^5$, $1\times10^{14}$-$1\times10^{16}$, or about, at least, or less than 5, 10, 50, 100, 500, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$ $1\times10^{15}$, $1\times10^{16}$, $1\times10^{17}$, $1\times10^{18}$, $1\times10^{19}$, or $1\times10^{20}$ inactivated, non-viable, or dead *Bacillus coagulans* vegetative bacteria and/or spores. In various embodiments, the number of inactivated, non-viable, or dead *Bacillus coagulans* vegetative bacteria and/or spores in a composition is about $1\times10^5$-$1\times10^7$ per gram or about $1\times10^5$, $1.5\times10^5$, $2\times10^5$, $2.5\times10^5$, $3\times10^5$, $3.5\times10^5$, $4\times10^5$, $4.5\times10^5$, $5\times10^5$, $5.5\times10^5$, $6\times10^5$, $6.5\times10^5$, $7\times10^5$, $7.5\times10^5$, $8\times10^5$, $8.5\times10^5$, $9\times10^5$, $9.5\times10^5$, $1\times10^6$, $1.5\times10^6$, $2\times10^6$, $2.5\times10^6$, $3\times10^6$, $3.5\times10^6$, $4\times10^6$, $4.5\times10^6$, $5\times10^6$, $5.5\times10^6$, $6\times10^6$, $6.5\times10^6$, $7\times10^6$, $7.5\times10^6$, $8\times10^6$, $8.5\times10^6$, $9\times10^6$, $9.5\times10^6$, or $1\times10^7$, particles per gram.

In some embodiments, the inactivated, non-viable, or dead *Bacillus coagulans* bacteria (e.g., particles of inactivated, non-viable, or dead *Bacillus coagulans* bacteria) are treated to reduce the clumping thereof. In certain embodiments, treating the inactivated, non-viable, or dead bacteria comprises passing the inactivated, non-viable, or dead *Bacillus coagulans* bacteria through a sieve or filter. In various embodiments, treating the inactivated, non-viable, or dead *Bacillus coagulans* bacteria comprises combining the inactivated, non-viable, or dead *Bacillus coagulans* bacteria with a surfactant or emulsifier. In some embodiments, treating the inactivated, non-viable, or dead *Bacillus coagulans* bacteria comprises combining the inactivated, non-viable, or dead *Bacillus coagulans* bacteria with polysorbate 20 and/or polysorbate 80. In certain embodiments, treating the inactivated, non-viable, or dead *Bacillus coagulans* bacteria comprises combining the inactivated, non-viable, or dead *Bacillus coagulans* bacteria with maltodextrin, inulin, inositol, trehalose, micro-crystalline cellulose (MCC), calcium lactate, magnesium stearate, fructo-oligosaccharide (FOS), or gluco-oligosaccharide (GOS).

In various embodiments, inactivated, non-viable, or dead *Bacillus coagulans* bacteria (e.g., alone or as part of a coating composition) are or have been applied to an external surface (e.g., as a coating on one or more surfaces, e.g. the top surface or the entire surface) by a physical process. Non-limiting examples of physical processes include atomization coating, spray dry coating, spinning disk coating, extrusion coating, fluidized bed coating, pan coating, dripping, emulsion coating, suspension coating, and centrifugal extrusion coating.

The form of administration of the inactivated probiotic in the method of the invention is not critical, as long as an effective amount is administered. As used herein, "effective" when referring to an amount of an inactivated, non-viable, or dead *Bacillus coagulans* bacterium (or a particle comprising inactivated, non-viable, or dead *Bacillus coagulans* bacteria) refers to the quantity of the inactivated, non-viable, or dead *Bacillus coagulans* bacteria (or particle) that is sufficient to yield a desired response without undue adverse side effects (such as toxicity, irritation, or allergic response) commensurate with a reasonable benefit/risk ratio when used in the manner of this disclosure.

In some embodiments, the inactivated, non-viable, or dead *Bacillus coagulans* bacteria (or particles comprising inactivated, non-viable, or dead *Bacillus coagulans* bacteria) are administered to a subject via tablets, pills, encapsulations, caplets, gel caps, capsules, oil drops, or sachets. In certain embodiments, the inactivated, non-viable, or dead *Bacillus coagulans* bacteria or particles, are encapsulated in a sugar, fat, or polysaccharide. In various embodiments, inactivated, non-viable, or dead *Bacillus coagulans* bacteria or particles, are added to a food or drink product and consumed. In some embodiments, the food or drink product is a nutritional product for children such as a follow-on formula, growing up milk, beverage, milk, yogurt, fruit juice, fruit-based drink, chewable tablet, cookie, cracker, or a milk powder. In certain embodiments, the product is an infant nutritional product, such as an infant formula or a human milk fortifier.

In some embodiments, the edible composition comprises a hard sweet, fudge, toffee, liquorice, chocolate, jelly candy, marshmallow, and marzipan. In various embodiments, the edible composition comprises chocolate. For example, the edible composition may include a candy bar comprising chocolate and at least one other ingredient.

Various implementations provide edible compositions with inactivated, non-viable, or dead *Bacillus coagulans* bacteria or particles the exterior surface thereof. Alternatively or in addition, inactivated, non-viable, or dead *Bacillus coagulans* bacteria may be present within the edible composition. For example, inactivated, non-viable, or dead *Bacillus coagulans* bacteria or particles may be on the exterior surface of and/or inside the edible composition.

Also provided are sports nutrition compositions. In some embodiments, the sports nutrition composition comprises at least about 10%, 20%, 30%, 40%, 50% or 60% protein by dry weight. A non-limiting example of sports nutrition compositions contain at least about 5, 10, 15, 20, 25, 30, 36, 40, 45, 50, 55, 60, 65, 70, 75, 80, 85, 90, 95, or 100 grams of carbohydrates and/or at least about 5, 10, 15, 20, 25, 30, 36, 40, 45, 50, 55, 60, 65, 70, 75, 80, 85, 90, 95, or 100 grams of protein. A non-limiting example of a sports nutrition composition includes protein powder for use in, e.g., a shake, pre-workout, or post-workout beverage. In some embodiments, the sports nutrition composition includes a vitamin or a mineral. Non-limiting examples of sports nutrition compositions include sports nutrition bars such as an energy bars, protein bars, endurance bars, meal replacement bars, pre-workout bars, and post-workout bars. Such sports nutrition bars may comprise, e.g., dried or dry grains (e.g., barley, oats, rice, rye, spelt, teff, triticale, wheat, sorghum, millet, maize, and/or fonio), nuts (e.g., almonds, brazil nuts, candlenuts, cashews, hazelnuts, macadamia nuts, chestnuts, pecans, peanuts, mongongo, pine nuts, pistachios, walnuts, and/or yeheb nuts), dried fruit, honey, animal protein, whey protein, vegetable protein, vitamins, minerals, sugars, fiber, and/or starches.

In some embodiments, the edible composition is a beverage. Non-limiting examples of beverages include tea, green tea, black tea, oolong tea, yellow tea, white tea, herbal tea, rosehip tea, chamomile tea, jiaogulan tea, ginger tea, peppermint tea, fruit tea, jasmine tea, hibiscus tea, lemongrass tea, ginseng tea, rooibos tea, coffee, juice, apple juice, coconut water, cranberry juice, grape juice, grapefruit juice, kiwifruit juice, lemonade, lemon juice, limeade, lime juice, limonana, melon juice, mora must, orange juice, papaya juice, pineapple juice, pomegranate juice, prune juice, strawberry juice, tomato juice, beet juice, carrot juice, celery juice, cucumber juice, dandelion-green juice, spinach juice, turnip juice, soda, orange soda, cola soda, root beer soda, cream soda, water, mineral water, seltzer water, or tonic water.

In certain embodiments, the edible composition is an alcoholic beverage. In various embodiments, the alcoholic beverage is beer, wine, or a spirit. In some embodiments, the alcoholic beverage is at least about 1, 2, 3, 4, 5, 10, 15, 20, 25, 30, 35, 40, 45, 50, 55, 60, 65, 70, 75, 80, 85, 90, or 95% ethanol by volume. In certain embodiments, the level of ethanol is effective to kill all vegetative *Bacillus coagulans* vegetative bacteria and/or spores that are added to it. Non-limiting examples of alcoholic beverages include beer, ale, barley wine, whiskey, shōchū, vodka, brem, tongba, boza, brem, huangjiu, choujiu, ruou gao, sake, sonti, makgeolli, chungju, tuak, thwon, kvass, burukutu, pito, merisa, bilibili, maotai, gaoliang, weizenkorn, sojum, horilka, cider, applejack, calvados, jabukovača, kajsijevača, kaisieva rakia, pálinka, feni, majmunovača, chuoi hot, cauim, urgwagwa, mbege, kasikisi, arrack, kirsch, ginger ale, ginger beer, ginger wine, gouqi jiu, red wine, white rine, rosé, lozovača, vinjak, brandy, cognac, vermouth, armagnac, branntwein, pisco, rakia, singani, arak, törkölypálinka, gin, genever, borovička, oghi, poiré, pear cider, plum wine, viljamovka, pear brandy, eau-de-vie, pálinka, krushova rakia, šljivovica, slivovitz, ţuică, umeshu, pálinka, slivova rakia, dunjevača, pomace wine, grappa, marc, orujo, tequila, mezcal, raicilla, pulque, cauim, chicha, kasiri, nihamanchi, mead, sambuca, and absinthe.

In various embodiments, the edible composition is a fermented food or beverage. Non-limiting examples of fermented foods and beverages include amasi, amazake, appam, atchara, ayran, bagoong, bagoong monamon, bagoong terong, bánh cuốn, beer, bland, boza, leavened bread, brem, burong mangga, buttermilk, calpis, chass, cheeses such as shanklish, cheonggukjang, chakuli pitha, fermented cod liver oil, crème fraiche, curtido, dhokla, doenjang, doogh, dosa, doubanjiang, douchi, enduri pitha, fermended bean curd, fermented bean paste, fermented fish, fermented milk products, filmjölk, ganjang, garri, gejang, gochujang, gundruk, hákarl, hongeohoe, idli, igunaq, ingera, iru, jeotgal, jogijeot, kapusta kiszona duszona, katsuobushi, kaymak, kefir, kenkey, khanom chin, kimchi, kiviak, kombucha, kumis, kusaya, kuzhi paniyaram, kvass, lassi, leben, lufu, mageu, massa de pimentão, meigan cai, miso, mixian, mohnyin tjin, murri, mursik, myeolchijeot, nata de coco, nattō, nem chua, ngapi, ogi, ogiri, oncom, palappam, pesaha appam, peuyeum, pickles, podpiwek, poi, pon ye gyi, pulque, puto, rakfisk, rượu nếp, ryazhenka, saeujeot, salami, sauerkraut, symbiotic cultures of bacteria and yeast, Şalgam, shiokara, fermented shimp paste, sinki, skyr, smântână, smetana, som moo, sour cabbage, sour cream, soured milk, sowans, soy sauce, ssamjang, stinky tofu, strained yogurt, suan cai, sumbala, surströmming, tapai, tarhana, tempeh, tesgüino, tianmianjiang, tianmianjiang, tibicos, tsukemono, tương, tung tsai, villi, vinegar, wine, white sugar sponge cake, Worcestershire sauce, yakult, fermented yellow soybean paste, yogurt, zha cai, and inčica.

In some embodiments, the edible composition comprises a soup. In certain embodiments, the edible composition comprises a grain. In various embodiments, the edible composition comprises a grain-based composition. In some embodiments, the grain-based composition comprises pasta, oatmeal, grits, or cereal. Non-limiting examples of pasta include tubular pasta, straight round rod pasta, ribbon pasta, micro pasta, stuffed pasta, irregular-shaped pasta, spaghetti (solid, thin cylinders), macaroni (tubes or hollow cylinders), fusilli (spiral-shaped), lasagna (sheets), tagliatelle (flat ribbons), vermicelli (thin spaghetti), and ravioli (filled pasta), penne (cylinder-shaped pasta), rotini (corkscrew-shaped pasta), rigatoni (tube-shaped pasta), noodles, and spätzle. In certain embodiments, the pasta is dried. In various embodiments, the pasta is fresh. In some embodiments, the pasta comprises egg pasta. In some embodiments, the pasta does not include egg.

In certain embodiments, the edible composition comprises a baked composition. In various embodiments, the baked composition comprises a bread, a cake, a muffin, a pie, a tart, a pastry, a food bar, a granola bar, a quiche, a cookie, a pizza, a baked corn chip, a baked tortilla chip, a baked potato chip, a baked cracker, and baked treats for companion animals.

In some embodiments, the composition comprises a dairy composition. In certain embodiments, the composition comprises a milk-like composition.

In various embodiments, the inactivated, non-viable, or dead *Bacillus coagulans* bacteria or particles are administered orally. In some embodiments, the inactivated, non-viable, or dead *Bacillus coagulans* bacteria or particles are administered nasally, topically (e.g., to a mucus membrane and/or to the skin), intraperitoneally, or intravenously.

In certain embodiments, a composition is formulated as a tablet, capsule, lozenge, aqueous solution, syrup, suspension, emulsion, powder, gel, lotion, or cream.

In some embodiments, the composition is a supplement composition. A supplement composition is a composition comprising an added dietary supplement. As used herein, the term "dietary supplement" is defined as in the United States Dietary Supplement Health and Education Act of 1994 (DSHEA). In various embodiments, a dietary supplement is a product (other than tobacco) intended to supplement the diet that bears or contains one or more of the following dietary ingredients: (A) a vitamin; (B) a mineral; (C) an herb or other botanical; (D) an amino acid; (E) a dietary supplement used by man to supplement the diet by increasing the total dietary intake; or (F) a concentrate, metabolite, constituent, extract, or combination of any ingredient described in (A), (B), (C), (D), or (E).

Various strains of *Bacillus coagulans* may be used to create inactivated, non-viable, or dead *Bacillus coagulans* bacteria in compositions, coatings, particles, and edible compositions of the present subject matter. For example, the *Bacillus coagulans* may include one or more of *Bacillus coagulans* Hammer strain Accession No. ATCC 31284, a strain derived from *Bacillus coagulans* Hammer strain Accession No. ATCC 31284, GBI-30 strain (ATCC Designation Number PTA-6086), GBI-20 strain (ATCC Designation Number PTA-6085), or GBI-40 strain (ATCC Designation Number PTA-6087).

The present subject matter provides compositions comprising inactivated, non-viable, or dead *Bacillus coagulans* bacteria (e.g., particles comprising inactivated, non-viable, or dead *Bacillus coagulans* bacteria and compositions comprising such particles). In some embodiments, the inactivated, non-viable, or dead *Bacillus coagulans* bacteria or particles comprising such bacteria may be in the form of a dry mix that is suitable for addition to, e.g., food compositions. In certain embodiments, the dry mix may be between 1% and 50% inactivated, non-viable, or dead *Bacillus coagulans* bacteria, e.g., about 5%, about 10%, about 15%, about 20%, about 25%, about 35%, about 45%, or about 50% inactivated, non-viable, or dead *Bacillus coagulans* bacteria by weight (e.g., dry weight). In various embodiments, the dry mix is about 15% inactivated, non-viable, or dead *Bacillus coagulans* bacteria by weight. For example, about 100 pounds of dry mix may contain about 15 pounds of inactivated, non-viable, or dead *Bacillus coagulans* bacteria.

The *Bacillus coagulans* Hammer strains are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains described herein germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Unless specifically defined otherwise, all technical and scientific terms used herein shall be taken to have the same meaning as commonly understood by one of ordinary skill in the art (e.g., in cell culture, molecular genetics, and biochemistry).

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," herein and in the claims is intended to mean, "based at least in part on," such that an unrecited feature or element is also permissible.

As used herein, the term "about" in the context of a numerical value or range means ±10% of the numerical value or range recited or claimed, unless the context requires a more limited range.

Where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

The transitional term "comprising," which is synonymous with "including," "containing," or "characterized by," is inclusive or open-ended and does not exclude additional, unrecited elements, method steps, or ingredients. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Where methods and compositions are disclosed using the transitional term "comprising" it will be understood that corresponding methods and compositions with the transitional term "consisting of" and "consisting essentially of" are also disclosed.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. In certain embodiments relating to two sequences of different lengths, the comparison window includes the entire length of the shorter of the two sequences. In some embodiments relating to two sequences of different lengths, the comparison window includes the entire length of the longer of the two sequences.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as is known in the art. An exemplary BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In certain embodiments, the NCBI BLASTN or BLASTP program is used to align sequences. In certain embodiments, the BLASTN or BLASTP program uses the defaults used by the NCBI. In certain embodiments, the BLASTN program (for nucleotide sequences) uses as defaults: a word size (W) of 28; an expectation threshold (E) of 10; max matches in a query range set to 0; match/mismatch scores of 1,-2; linear gap costs; the filter for low complexity regions used; and mask for lookup table only used. In certain embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

Each embodiment disclosed herein is contemplated as being applicable to each of the other disclosed embodiments. Thus, all combinations of the various elements described herein are within the scope of the invention.

DETAILED DESCRIPTION

Figure 1A:
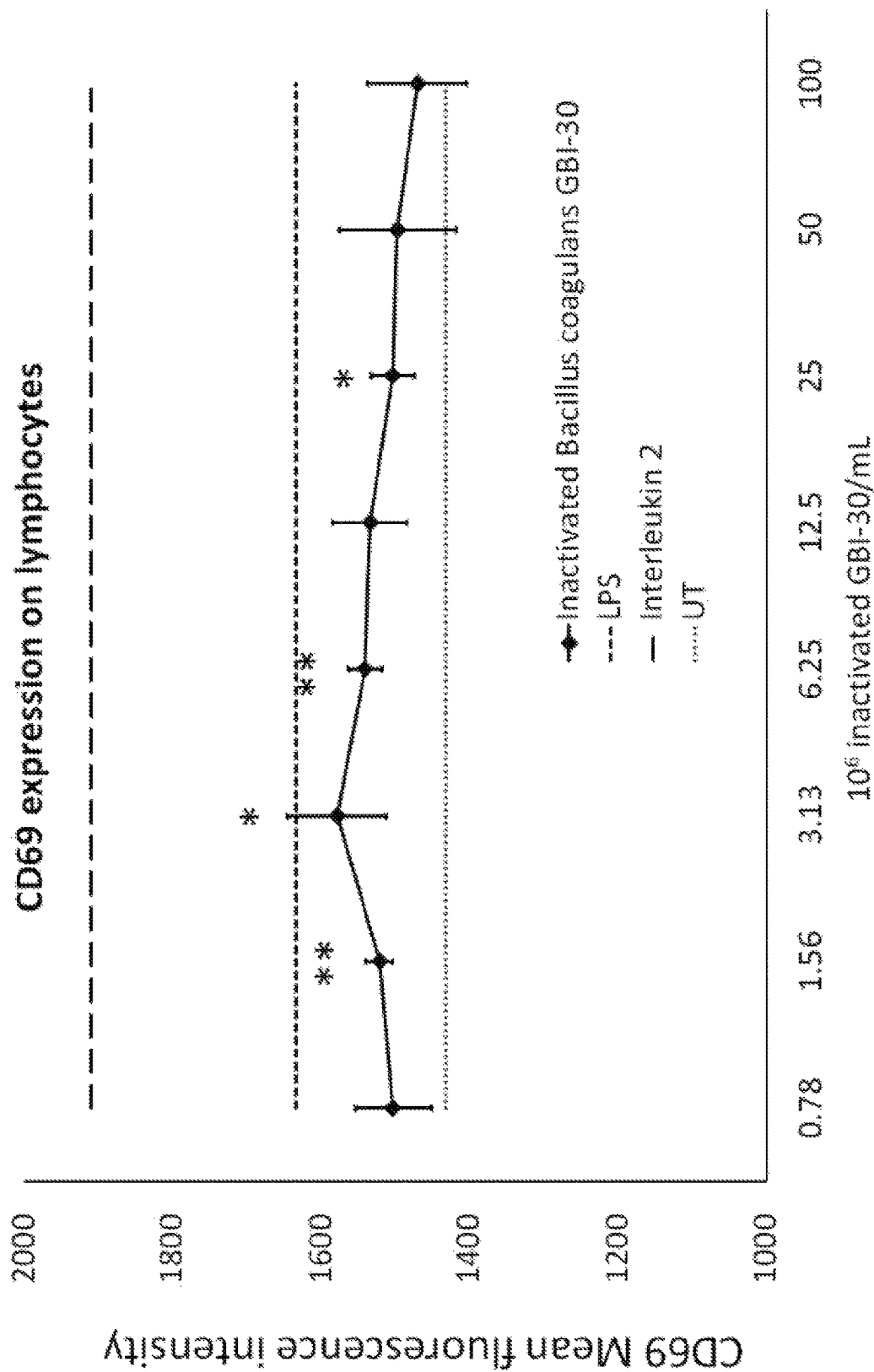
FIGS. 1A and B are graphs showing expression of the CD69 cellular activation marker on lymphocytes and monocytes. CD69 expression on lymphocytes (FIG. 1A) and monocytes (FIG. 1B) in human PBMC cultures treated for 24 hours with serial dilutions of inactivated *Bacillus coagulans* GBI-30. Mean fluorescence intensity for CD69 expression is shown. Data presented as mean±standard deviation from triplicate cultures and represents one of three separate experiments using PBMC cells from three different healthy human donors. Abbreviations: LPS, Lipopolysaccharide; UT, untreated. Notes: *P<0.05; **P<0.01.

The present subject matter provides, inter alia, compositions comprising inactivated, non-viable, and/or dead *Bacillus coagulans* bacteria. In various embodiments, the inactivated, non-viable, and/or dead *Bacillus coagulans* bacteria comprise inactivated, non-viable, and/or dead *Bacillus coagulans* spores. A non-limiting example of a suitable *Bacillus coagulans* strain is GBI-30. Whole dead bacteria (e.g., spores and/or vegetative bacteria) or particles comprising whole dead bacteria stimulate the production of beneficial growth factors in subjects, e.g., humans, that have ingested the dead cells or particles containing such dead cells. Surprisingly, dead *Bacillus coagulans* bacteria have similar effects to live bacteria with respect to immune activation and anti-inflammatory effects. The administration of dead *Bacillus coagulans* bacteria increases the secretion of growth factors by human cells, including growth factors that are important for tissue repair after exercise, trauma, and injury.

Various implementations of the present subject matter relate to increasing a subject's physical performance, e.g., by reducing muscle soreness (such as post-exercise muscle soreness), increasing physical strength or endurance (such as by decreasing post-exercise recovery time), increasing muscle mass, and/or increasing lean muscle development, recovery, strength, or repair.

*Bacillus coagulans*

*Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., Bergey's Manual of Systemic Bacteriology, Vol. 2, Sneath, P. H. A. et al., eds., Williams & Wilkins, Baltimore, Md., 1986). Isolated *Bacillus coagulans* strains have served as a source of enzymes including endonucleases (e.g., U.S. Pat. No. 5,200,336); amylase (U.S. Pat. No. 4,980,180); lactase (U.S. Pat. No. 4,323,651) and cyclo-malto-dextrin glucano-transferase (U.S. Pat. No. 5,102,800).

Various *Bacillus coagulans* bacterial strains that are currently commercially available from the American Type Culture Collection (ATCC, Manassas, Va.) include the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); and *Bacillus coagulans* Hammer NCA 4259 (ATCC No. 15949). Purified *Bacillus coagulans* bacteria are also available from the Deutsche Sammlung von Mikroorganismen und Zellkulturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as Nebraska Cultures (Walnut Creek, Calif.). Compositions include strains or variants derived from *Bacillus coagulans* Hammer strain ATCC No. 31284 such as ATCC PTA-6085, PTA-6086, or PTA-6087.

In some embodiments, the *Bacillus coagulans* is *Bacillus coagulans* Hammer strain Accession No. ATCC 31284, or one or more strains derived from *Bacillus coagulans* Hammer strain Accession No. ATCC 31284 (e.g., ATCC Numbers: GBI-20, ATCC Designation Number PTA-6085; GBI-30 (ATCC Designation Number PTA-6086, also known as "BC30"); and GBI-40, ATCC Designation Number PTA-6087; see U.S. Pat. No. 6,849,256 to Farmer, the entire contents of which are incorporated herein by reference).

*Bacillus coagulans* was previously mischaracterized as a *Lactobacillus* and labeled as *Lactobacillus sporogenes* (Nakamura et al. 1988. Int. J. Syst. Bacteria 38: 63-73). However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic *Lactobacillus* species are unsuitable for colonization of the gut due to their instability in the harsh (i.e., acidic) pH environment of the bile, particularly human bile. By contrast, *Bacillus coagulans* is able to survive and colonize the gastrointestinal tract in the bile environment and even grown in this low pH range.

Non-Limiting Examples of Growth Factors

Provided herein are methods and compositions that are effective to increase the expression of 1 or more growth factors in a subject. Non-limiting examples of such growth factors include G-CSF (granulocyte colony-stimulating factor) and GM-CSF (granulocyte macrophage colony-stimulating factor).

For specific growth factor proteins described herein (e.g., G-CSF and GM-CSF), the named protein includes any of the protein's naturally occurring forms (such as isoforms and naturally occurring mutants and variants thereof). Non-human homologues of the human protein are also included with respect to non-human subjects. In certain embodiments, a non-human homologue is a mammalian protein having an amino acid sequence that it at least about 50%, 55%, 60%, 65%, 70%, 75%, 80%, 85%, 90%, 91%, 92%, 93%, 94%, 95%, 96%, 97%, 98%, 99% identical to the amino acid sequence of a human protein described herein. In various embodiments, a growth factor protein is the protein as identified by a United States National Center for Biotechnology Information (NCBI) sequence reference. In some embodiments, a growth factor protein is the protein as identified by a UniProt sequence reference.

In certain embodiments, human G-CSF is the protein as identified by the NCBI sequence reference NP_000750.1 or an isoform or naturally occurring mutant or variant thereof. In various embodiments, human G-CSF is the protein as identified by the NCBI sequence reference NP_001171618.1 or an isoform or naturally occurring mutant or variant thereof. In certain embodiments, human G-CSF is the protein as identified by the NCBI sequence reference NP_757373.1 or an isoform or naturally occurring mutant or variant thereof. In various embodiments, human G-CSF is the protein as identified by the NCBI sequence reference NP_757374.2 or an isoform or naturally occurring mutant or variant thereof. Non-limiting examples of human G-CSF amino acid sequences available under NCBI sequence references are as follows:

NP_000750.1
(SEQ ID NO: 1)
MAGPATQSPMKLMALQLLLWHSALWTVQEATPLGPASSLPQSFLLKCLEQ

VRKIQGDGAALQEKLVSECATYKLCHPEELVLLGHSLGIPWAPLSSCPSQ

ALQLAGCLSQLHSGLFLYQGLLQALEGISPELGPTLDTLQLDVADFATTI

WQQMEELGMAPALQPTQGAMPAFASAFQRRAGGVLVASHLQSFLEVSYRV

LRHLAQP

NP_001171618.1
(SEQ ID NO: 2)
MAGPATQSPMKLMALQLLLWHSALWTVQEATPLGPASSLPQSFLLKCLEQ

VRKIQGDGAALQEKLAGCLSQLHSGLFLYQGLLQALEGISPELGPTLDTL

QLDVADFATTIWQQMEELGMAPALQPTQGAMPAFASAFQRRAGGVLVASH

LQSFLEVSYRVLRHLAQP

NP_757373.1
(SEQ ID NO: 3)
MAGPATQSPMKLMALQLLLWHSALWTVQEATPLGPASSLPQSFLLKCLEQ

VRKIQGDGAALQEKLCATYKLCHPEELVLLGHSLGIPWAPLSSCPSQALQ

LAGCLSQLHSGLFLYQGLLQALEGISPELGPTLDTLQLDVADFATTIWQQ

MEELGMAPALQPTQGAMPAFASAFQRRAGGVLVASHLQSFLEVSYRVLRH

LAQP

NP_757374.2
(SEQ ID NO: 4)
MAGPATQSPMKLMALQLLLWHSALWTVQEATPLGPASSLPQSFLLKCLEQ

VRKIQGDGAALQEKLVSEAGCLSQLHSGLFLYQGLLQALEGISPELGPTL

DTLQLDVADFATTIWQQMEELGMAPALQPTQGAMPAFASAFQRRAGGVLV

ASHLQSFLEVSYRVLRHLAQP

In some embodiments, human G-CSF is the protein as identified by the UniProt reference P09919 or an isoform or naturally occurring mutant or variant thereof. Non-limiting examples of human G-CSF amino acid sequences available under UniProt reference P09919 are as follows:

Isoform Long (identifier: P09919-1)
(SEQ ID NO: 5)
MAGPATQSPMKLMALQLLLWHSALWTVQEATPLGPASSLPQSFLLKCLEQ

VRKIQGDGAALQEKLVSECATYKLCHPEELVLLGHSLGIPWAPLSSCPSQ

ALQLAGCLSQLHSGLFLYQGLLQALEGISPELGPTLDTLQLDVADFATTI

WQQMEELGMAPALQPTQGAMPAFASAFQRRAGGVLVASHLQSFLEVSYRV

LRHLAQP

Isoform Short (identifier: P09919-2)
(SEQ ID NO: 6)
MAGPATQSPMKLMALQLLLWHSALWTVQEATPLGPASSLPQSFLLKCLEQ

VRKIQGDGAALQEKLCATYKLCHPEELVLLGHSLGIPWAPLSSCPSQALQ

LAGCLSQLHSGLFLYQGLLQALEGISPELGPTLDTLQLDVADFATTIWQQ

MEELGMAPALQPTQGAMPAFASAFQRRAGGVLVASHLQSFLEVSYRVLRH

LAQP

Isoform 3 (identifier: P09919-3)
(SEQ ID NO: 7)
MAGPATQSPMKLMALQLLLWHSALWTVQEATPLGPASSLPQSFLLKCLEQ

VRKIQGDGAALQEKLVSEAGCLSQLHSGLFLYQGLLQALEGISPELGPTL

DTLQLDVADFATTIWQQMEELGMAPALQPTQGAMPAFASAFQRRAGGVLV

ASHLQSFLEVSYRVLRHLAQP

A non-limiting example of a nucleotide sequence that encodes human G-CSF is as follows (the start and stop codons are underlined and bolded):

(SEQ ID NO: 8)
AGTCGTGGCCCCAGGTAATTTCCTCCCAGGCCTCCATGGGGTTATGTATA

AAGGCCCCCCTAGAGCTGGGCCCCAAAACAGCCCGGAGCCTGCAGCCCAG

CCCCACCCAGACCCATGGCTGGACCTGCCACCCAGAGCCCCATGAAGCTG

ATGGCCCTGCAGCTGCTGCTGTGGCACAGTGCACTCTGGACAGTGCAGGA

AGCCACCCCCTGGGCCCTGCCAGCTCCCTGCCCCAGAGCTTCCTGCTCA

AGTGCTTAGAGCAAGTGAGGAAGATCCAGGGCGATGGCGCAGCGCTCCAG

GAGAAGCTGGTGAGTGAGTGTGCCACCTACAAGCTGTGCCACCCCGAGGA

GCTGGTGCTGCTCGGACACTCTCTGGGCATCCCCTGGGCTCCCCTGAGCA

GCTGCCCCAGCCAGGCCCTGCAGCTGGCAGGCTGCTTGAGCCAACTCCAT

AGCGGCCTTTTCCTCTACCAGGGGCTCCTGCAGGCCCTGGAAGGGATCTC

CCCCGAGTTGGGTCCCACCTTGGACACACTGCAGCTGGACGTCGCCGACT

TTGCCACCACCATCTGGCAGCAGATGGAAGAACTGGGAATGGCCCCTGCC

CTGCAGCCCACCCAGGGTGCCATGCCGGCCTTCGCCTCTGCTTTCCAGCG

CCGGGCAGGAGGGGTCCTGGTTGCCTCCCATCTGCAGAGCTTCCTGGAGG

TGTCGTACCGCGTTCTACGCCACCTTGCCCAGCCCTGAGCCAAGCCCTCC

CCATCCCATGTATTTATCTCTATTTAATATTTATGTCTATTTAAGCCTCA

TATTTAAAGACAGGGAAGAGCAGAACGGAGCCCCAGGCCTCTGTGTCCTT

CCCTGCATTTCTGAGTTTCATTCTCCTGCCTGTAGCAGTGAGAAAAAGCT

CCTGTCCTCCCATCCCTGGACTGGGAGGTAGATAGGTAAATACCAAGTA

TTTATTACTATGACTGCTCCCCAGCCCTGGCTCTGCAATGGGCACTGGGA

TGAGCCGCTGTGAGCCCCTGGTCCTGAGGGTCCCCACCTGGGACCCTTGA

GAGTATCAGGTCTCCCACGTGGGAGACAAGAAATCCCTGTTTAATATTTA

AACAGCAGTGTTCCCCATCTGGGTCCTTGCACCCCTCACTCTGGCCTCAG

CCGACTGCACAGCGGCCCCTGCATCCCCTTGGCTGTGAGGCCCCTGGACA

AGCAGAGGTGGCCAGAGCTGGGAGGCATGGCCCTGGGGTCCCACGAATTT

GCTGGGGAATCTCGTTTTTCTTCTTAAGACTTTTGGGACATGGTTTGACT

```
CCCGAACATCACCGACGCGTCTCCTGTTTTTCTGGGTGGCCTCGGGACAC

CTGCCCTGCCCCCACGAGGGTCAGGACTGTGACTCTTTTTAGGGCCAGGC

AGGTGCCTGGACATTTGCCTTGCTGGACGGGGACTGGGGATGTGGGAGGG

AGCAGACAGGAGGAATCATGTCAGGCCTGTGTGTGAAAGGAAGCTCCACT

GTCACCCTCCACCTCTTCACCCCCCACTCACCAGTGTCCCCTCCACTGTC

ACATTGTAACTGAACTTCAGGATAATAAAGTGTTTGCCTCCAAAAAAAA

AA
```

In certain embodiments, human GM-CSF is the protein as identified by the NCBI sequence reference NP_000749.2 or an isoform or naturally occurring mutant or variant thereof. A human GM-CSF amino acid sequence that is available under NCBI sequence reference NP_000749.2 is as follows:

```
                                           (SEQ ID NO: 9)
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE
```

In some embodiments, human GM-CSF is the protein as identified by the UniProt reference P04141 or an isoform or naturally occurring mutant or variant thereof. A human GM-CSF amino acid sequence that is available under UniProt reference P04141 is as follows:

```
                                          (SEQ ID NO: 10)
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE
```

A non-limiting example of a nucleotide sequence that encodes human GM-CSF is as follows (the start and stop codons are underlined and bolded):

```
                                          (SEQ ID NO: 11)
ACACAGAGAGAAAGGCTAAAGTTCTCTGGAGGATGTGGCTGCAGAGCCTG

CTGCTCTTGGGCACTGTGGCCTGCAGCATCTCTGCACCCGCCCGCTCGCC

CAGCCCCAGCACGCAGCCCTGGGAGCATGTGAATGCCATCCAGGAGGCCC

GGCGTCTCCTGAACCTGAGTAGAGACACTGCTGCTGAGATGAATGAAACA

GTAGAAGTCATCTCAGAAATGTTTGACCTCCAGGAGCCGACCTGCCTACA

GACCCGCCTGGAGCTGTACAAGCAGGGCCTGCGGGGCAGCCTCACCAAGC

TCAAGGGCCCCTTGACCATGATGGCCAGCCACTACAAGCAGCACTGCCCT

CCAACCCCGGAAACTTCCTGTGCAACCCAGATTATCACCTTTGAAAGTTT

CAAAGAGAACCTGAAGGACTTTCTGCTTGTCATCCCCTTTGACTGCTGGG

AGCCAGTCCAGGAGTGAGACCGGCCAGATGAGGCTGGCCAAGCCGGGGAG

CTGCTCTCTCATGAAACAAGAGCTAGAAACTCAGGATGGTCATCTTGGAG

GGACCAAGGGGTGGGCCACAGCCATGGTGGGAGTGGCCTGGACCTGCCCT

GGGCCACACTGACCCTGATACAGGCATGGCAGAAGAATGGGAATATTTTA

TACTGACAGAAATCAGTAATATTTATATATTTATATTTTTAAAATATTTA

TTTATTTATTTTAAGTTCATATTCCATATTTATTCAAGATGTTTTAC

CGTAATAATTATTATTAAAAATATGCTTCTACTTGAAAAAAAAAAAAAAA
```

Non-Limiting Examples of Cytokines and Chemokines

Provided herein are methods and compositions that are effective to increase the expression of 1 or more cytokines or chemokines in a subject. Non-limiting examples of such cytokines include IL1RA, IL-6, IL-10, IL-1β, IL-17A, TNF-α, IFN-γ. Non-limiting examples of such chemokines include MCP-1, MIP-1α, or MIP1β.

For specific proteins described herein (e.g., IL1RA, IL-6, IL-10, IL-1β, IL-17A, TNF-α, IFN-γ, MCP-1, MIP-1α, and MIP1β), the named protein includes any of the protein's naturally occurring forms (such as isoforms and naturally occurring mutants and variants thereof). Non-human homologues of the human protein are also included with respect to non-human subjects. In certain embodiments, a non-human homologue is a mammalian protein having an amino acid sequence that it at least about 50%, 55%, 60%, 65%, 70%, 75%, 80%, 85%, 90%, 91%, 92%, 93%, 94%, 95%, 96%, 97%, 98%, 99% identical to the amino acid sequence of a human protein described herein. In various embodiments, a cytokine or chemokine protein is the protein as identified by a United States National Center for Biotechnology Information (NCBI) sequence reference. In some embodiments, a protein is the protein as identified by a UniProt sequence reference.

In certain embodiments, human IL1RA is the protein as identified by the NCBI sequence reference NP_001305843.1 or an isoform or naturally occurring mutant or variant thereof. In various embodiments, human IL1RA is the protein as identified by the NCBI sequence reference NP_776215.1 or an isoform or naturally occurring mutant or variant thereof. In various embodiments, human IL1RA is the protein as identified by the NCBI sequence reference NP_776214.1 or an isoform or naturally occurring mutant or variant thereof. In certain embodiments, human IL1RA is the protein as identified by the NCBI sequence reference NP_776213.1 or an isoform or naturally occurring mutant or variant thereof. In certain embodiments, human IL1RA is the protein as identified by the NCBI sequence reference NP_000568.1 or an isoform or naturally occurring mutant or variant thereof. Non-limiting examples of human IL1RA amino acid sequences available under NCBI sequence references are as follows:

```
NP_001305843.1
                                          (SEQ ID NO: 12)
MQAFRIWDVNQKTFYLRNNQLVAGYLQGPNVNLEEKIDVVPIEPHALFLG

IHGGKMCLSCVKSGDETRLQLEAVNITDLSENRKQDKRFAFIRSDSGPTT

SFESAACPGWFLCTAMEADQPVSLTNMPDEGVMVTKFYFQEDE

NP_776215.1
                                          (SEQ ID NO: 13)
MQAFRIWDVNQKTFYLRNNQLVAGYLQGPNVNLEEKIDVVPIEPHALFLG

IHGGKMCLSCVKSGDETRLQLEAVNITDLSENRKQDKRFAFIRSDSGPTT

SFESAACPGWFLCTAMEADQPVSLTNMPDEGVMVTKFYFQEDE

NP_776214.1
                                          (SEQ ID NO: 14)
MEICRGLRSHLITLLLFLFHSETICRPSGRKSSKMQAFRIWDVNQKTFYL

RNNQLVAGYLQGPNVNLEEKIDVVPIEPHALFLGIHGGKMCLSCVKSGDE
```

-continued
TRLQLEAVNITDLSENRKQDKRFAFIRSDSGPTTSFESAACPGWFLCTAM

EADQPVSLTNMPDEGVMVTKFYFQEDE

NP_776213.1
(SEQ ID NO: 15)
MALADLYEEGGGGGGEGEDNADSKETICRPSGRKSSKMQAFRIWDVNQKT

FYLRNNQLVAGYLQGPNVNLEEKIDVVPIEPHALFLGIHGGKMCLSCVKS

GDETRLQLEAVNITDLSENRKQDKRFAFIRSDSGPTTSFESAACPGWFLC

TAMEADQPVSLTNMPDEGVMVTKFYFQEDE

NP_000568.1
(SEQ ID NO: 16)
MALETICRPSGRKSSKMQAFRIWDVNQKTFYLRNNQLVAGYLQGPNVNLE

EKIDVVPIEPHALFLGIHGGKMCLSCVKSGDETRLQLEAVNITDLSENRK

QDKRFAFIRSDSGPTTSFESAACPGWFLCTAMEADQPVSLTNMPDEGVMV

TKFYFQEDE

In some embodiments, human IL1RA is the protein as identified by the UniProt reference P18510 or an isoform or naturally occurring mutant or variant thereof. Non-limiting examples of human IL1RA amino acid sequences available under UniProt reference P18510 are as follows:

P18510-1
(SEQ ID NO: 17)
MEICRGLRSHLITLLLFLFHSETICRPSGRKSSKMQAFRIWDVNQKTFY

LRNNQLVAGYLQGPNVNLEEKIDVVPIEPHALFLGIHGGKMCLSCVKSG

DETRLQLEAVNITDLSENRKQDKRFAFIRSDSGPTTSFESAACPGWFLC

TAMEADQPVSLTNMPDEGVMVTKFYFQEDE

P18510-2
(SEQ ID NO: 18)
MALETICRPSGRKSSKMQAFRIWDVNQKTFYLRNNQLVAGYLQGPNVNL

EEKIDVVPIEPHALFLGIHGGKMCLSCVKSGDETRLQLEAVNITDLSEN

RKQDKRFAFIRSDSGPTTSFESAACPGWFLCTAMEADQPVSLTNMPDEG

VMVTKFYFQEDE

P18510-3
(SEQ ID NO: 19)
MALADLYEEGGGGGGEGEDNADSKETICRPSGRKSSKMQAFRIWDVNQK

TFYLRNNQLVAGYLQGPNVNLEEKIDVVPIEPHALFLGIHGGKMCLSCV

KSGDETRLQLEAVNITDLSENRKQDKRFAFIRSDSGPTTSFESAACPGW

FLCTAMEADQPVSLTNMPDEGVMVTKFYFQEDE

P18510-4
(SEQ ID NO: 20)
MQAFRIWDVNQKTFYLRNNQLVAGYLQGPNVNLEEKIDVVPIEPHALFL

GIHGGKMCLSCVKSGDETRLQLEAVNITDLSENRKQDKRFAFIRSDSGP

TTSFESAACPGWFLCTAMEADQPVSLTNMPDEGVMVTKFYFQEDE

A non-limiting example of a nucleotide sequence that encodes human IL1RA is as follows (the start and stop codons are underlined and bolded):
(SEQ ID NO: 21)
GGGCAGCTCCACCCTGGGAGGGACTGTGGCCCAGGTACTGCCCGGGTGCT

ACTTTATGGGCAGCAGCTCAGTTGAGTTAGAGTCTGGAAGACCTCAGAAG

ACCTCCTGTCCTATGAGGCCCTCCCCATGGCTTTAGAGACGATCTGCCGA

CCCTCTGGGAGAAAATCCAGCAAGATGCAAGCCTTCAGAATCTGGGATGT

TAACCAGAAGACCTTCTATCTGAGGAACAACCAACTAGTTGCTGGATACT

TGCAAGGACCAAATGTCAATTTAGAAGAAAAGATAGATGTGGTACCCATT

GAGCCTCATGCTCTGTTCTTGGGAATCCATGGAGGGAAGATGTGCCTGTC

CTGTGTCAAGTCTGGTGATGAGACCAGACTCCAGCTGGAGGCAGTTAACA

TCACTGACCTGAGCGAGAACAGAAAGCAGGACAAGCGCTTCGCCTTCATC

CGCTCAGACAGTGGCCCCACCACCAGTTTTGAGTCTGCCGCCTGCCCCGG

TTGGTTCCTCTGCACAGCGATGGAAGCTGACCAGCCCGTCAGCCTCACCA

ATATGCCTGACGAAGGCGTCATGGTCACCAAATTCTACTTCCAGGAGGAC

GAGTAGTACTGCCCAGGCCTGCCTGTTCCCATTCTTGCATGGCAAGGACT

GCAGGGACTGCCAGTCCCCCTGCCCCAGGGCTCCCGGCTATGGGGGCACT

GAGGACCAGCCATTGAGGGGTGGACCCTCAGAAGGCGTCACAACAACCTG

GTCACAGGACTCTGCCTCCTCTTCAACTGACCAGCCTCCATGCTGCCTCC

AGAATGGTCTTTCTAATGTGTGAATCAGAGCACAGCAGCCCTGCACAAA

GCCCTTCCATGTCGCCTCTGCATTCAGGATCAAACCCCGACCACCTGCCC

AACCTGCTCTCCTCTTGCCACTGCCTCTTCCTCCCTCATTCCACCTTCCC

ATGCCCTGGATCCATCAGGCCACTTGATGACCCCCAACCAAGTGGCTCCC

ACACCCTGTTTTACAAAAAAGAAAAGACCAGTCCATGAGGGAGGTTTTTA

AGGGTTTGTGGAAAATGAAAATTAGGATTTCATGATTTTTTTTTTCAGT

CCCCGTGAAGGAGAGCCCTTCATTTGGAGATTATGTTCTTTCGGGGAGAG

GCTGAGGACTTAAAATATTCCTGCATTTGTGAAATGATGGTGAAAGTAAG

TGGTAGCTTTTCCCTTCTTTTTCTTCTTTTTTTGTGATGTCCCAACTTGT

AAAAATTAAAAGTTATGGTACTATGTTAGCCCCATAATTTTTTTTTCCT

TTTAAAACACTTCCATAATCTGGACTCCTCTGTCCAGGCACTGCTGCCCA

GCCTCCAAGCTCCATCTCCACTCCAGATTTTTTACAGCTGCCTGCAGTAC

TTTACCTCCTATCAGAAGTTTCTCAGCTCCCAAGGCTCTGAGCAAATGTG

GCTCCTGGGGGTTCTTTCTTCCTCTGCTGAAGGAATAAATTGCTCCTTGA

CATTGTAGAGCTTCTGGCACTTGGAGACTTGTATGAAAGATGGCTGTGCC

TCTGCCTGTCTCCCCCACCGGGCTGGGAGCTCTGCAGAGCAGGAAACATG

ACTCGTATATGTCTCAGGTCCCTGCAGGGCCAAGCACCTAGCCTCGCTCT

TGGCAGGTACTCAGCGAATGAATGCTGTATATGTTGGGTGCAAAGTTCCC

TACTTCCTGTGACTTCAGCTCTGTTTTACAATAAAATCTTGAAAATGCCT

AAAAAAAAAAAAAAAAAAAAAAAAAAAAAAAAAAAAAAAAAAAAAA

AA

In certain embodiments, human IL-6 is the protein as identified by the NCBI sequence reference NP_000591.1 or an isoform or naturally occurring mutant or variant thereof. In various embodiments, human IL-6 is the protein as identified by the NCBI sequence reference NP_001305024.1 or an isoform or naturally occurring mutant or variant thereof. Non-limiting examples of human IL-6 amino acid sequences available under NCBI sequence references are as follows:

NP_000591.1
(SEQ ID NO: 22)
MNSFSTSAFGPVAFSLGLLLVLPAAFPAPVPPGEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMTTHLILRSFKE

FLQSSLRALRQM

NP_001305024.1
(SEQ ID NO: 23)
MCESSKEALAENNLNLPKMAEKDGCFQSGFNEETCLVKIITGLLEFEVYL

EYLQNRFESSEEQARAVQMSTKVLIQFLQKKAKNLDAITTPDPTTNASLL

TKLQAQNQWLQDMTTHLILRSFKEFLQSSLRALRQM

In some embodiments, human IL-6 is the protein as identified by the UniProt reference P05231 or an isoform or naturally occurring mutant or variant thereof. A non-limiting example of a human IL-6 amino acid sequence available under UniProt reference P05231 is as follows:

(SEQ ID NO: 24)
MNSFSTSAFGPVAFSLGLLLVLPAAFPAPVPPGEDSKDVAAPHRQPLTSS

ERIDKQIRYILDGISALRKETCNKSNMCESSKEALAENNLNLPKMAEKDG

CFQSGFNEETCLVKIITGLLEFEVYLEYLQNRFESSEEQARAVQMSTKVL

IQFLQKKAKNLDAITTPDPTTNASLLTKLQAQNQWLQDMTTHLILRSFKE

FLQSSLRALRQM

A non-limiting example of a nucleotide sequence that encodes human IL-6 is as follows (the start and stop codons are underlined and bolded):

(SEQ ID NO: 25)
GTCTCAATATTAGAGTCTCAACCCCCAATAAATATAGGACTGGAGATGTC

TGAGGCTCATTCTGCCCTCGAGCCCACCGGGAACGAAAGAGAAGCTCTAT

CTCCCCTCCAGGAGCCCAGCTATGAACTCCTTCTCCACAAGCGCCTTCGG

TCCAGTTGCCTTCTCCCTGGGGCTGCTCCTGGTGTTGCCTGCTGCCTTCC

CTGCCCCAGTACCCCCAGGAGAAGATTCCAAAGATGTAGCCGCCCCACAC

AGACAGCCACTCACCTCTTCAGAACGAATTGACAAACAAATTCGGTACAT

CCTCGACGGCATCTCAGCCCTGAGAAAGGAGACATGTAACAAGAGTAACA

TGTGTGAAAGCAGCAAAGAGGCACTGGCAGAAAACAACCTGAACCTTCCA

AAGATGGCTGAAAAAGATGGATGCTTCCAATCTGGATTCAATGAGGAGAC

TTGCCTGGTGAAAATCATCACTGGTCTTTTGGAGTTTGAGGTATACCTAG

AGTACCTCCAGAACAGATTTGAGAGTAGTGAGGAACAAGCCAGAGCTGTG

CAGATGAGTACAAAAGTCCTGATCCAGTTCCTGCAGAAAAAGGCAAAGAA

TCTAGATGCAATAACCACCCCTGACCCAACCACAAATGCCAGCCTGCTGA

CGAAGCTGCAGGCACAGAACCAGTGGCTGCAGGACATGACAACTCATCTC

ATTCTGCGCAGCTTTAAGGAGTTCCTGCAGTCCAGCCTGAGGGCTCTTCG

GCAAATGTAGCATGGGCACCTCAGATTGTTGTTGTTAATGGGCATTCCTT

CTTCTGGTCAGAAACCTGTCCACTGGGCACAGAACTTATGTTGTTCTCTA

TGGAGAACTAAAAGTATGAGCGTTAGGACACTATTTTAATTATTTTTAAT

TTATTAATATTTAAATATGTGAAGCTGAGTTAATTTATGTAAGTCATATT

TATATTTTTAAGAAGTACCACTTGAAACATTTTATGTATTAGTTTTGAAA

TAATAATGGAAAGTGGCTATGCAGTTTGAATATCCTTTGTTTCAGAGCCA

GATCATTTCTTGGAAAGTGTAGGCTTACCTCAAATAAATGGCTAACTTAT

ACATATTTTTAAAGAAATATTTATATTGTATTTATATAATGTATAAATGG

TTTTTATACCAATAAATGGCATTTTAAAAAATTCAGCAAAAAAAAAA

In certain embodiments, human IL-10 is the protein as identified by the NCBI sequence reference NP_000563.1 or an isoform or naturally occurring mutant or variant thereof. A non-limiting example of human IL-10 amino acid sequence that is available under NCBI sequence reference NP_000563.1 is as follows:

(SEQ ID NO: 26)
MHSSALLCCLVLLTGVRASPGQGTQSENSCTHFPGNLPNMLRDLRDAFSR

VKTFFQMKDQLDNLLLKESLLEDFKGYLGCQALSEMIQFYLEEVMPQAEN

QDPDIKAHVNSLGENLKTLRLRLRRCHRFLPCENKSKAVEQVKNAFNKLQ

EKGIYKAMSEFDIFINYIEAYMTMKIRN

In some embodiments, human IL-10 is the protein as identified by the UniProt reference P22301 or an isoform or naturally occurring mutant or variant thereof. A non-limiting example of a human IL-10 amino acid sequence that is available under UniProt reference P22301 is as follows:

(SEQ ID NO: 27)
MHSSALLCCLVLLTGVRASPGQGTQSENSCTHFPGNLPNMLRDLRDAFSR

VKTFFQMKDQLDNLLLKESLLEDFKGYLGCQALSEMIQFYLEEVMPQAEN

QDPDIKAHVNSLGENLKTLRLRLRRCHRFLPCENKSKAVEQVKNAFNKLQ

EKGIYKAMSEFDIFINYIEAYMTMKIRN

A non-limiting example of a nucleotide sequence that encodes human IL-10 is as follows (the start and stop codons are underlined and bolded):

(SEQ ID NO: 28)
ACACATCAGGGGCTTGCTCTTGCAAAACCAAACCACAAGACAGACTTGCA

AAAGAAGGCATGCACAGCTCAGCACTGCTCTGTTGCCTGGTCCTCCTGAC

TGGGGTGAGGGCCAGCCCAGGCCAGGGCACCCAGTCTGAGAACAGCTGCA

CCCACTTCCCAGGCAACCTGCCTAACATGCTTCGAGATCTCCGAGATGCC

TTCAGCAGAGTGAAGACTTTCTTTCAAATGAAGGATCAGCTGGACAACTT

GTTGTTAAAGGAGTCCTTGCTGGAGGACTTTAAGGGTTACCTGGGTTGCC

AAGCCTTGTCTGAGATGATCCAGTTTTACCTGGAGGAGGTGATGCCCCAA

GCTGAGAACCAAGACCCAGACATCAAGGCGCATGTGAACTCCCTGGGGGA

GAACCTGAAGACCCTCAGGCTGAGGCTACGGCGCTGTCATCGATTTCTTC

CCTGTGAAAACAAGAGCAAGGCCGTGGAGCAGGTGAAGAATGCCTTTAAT

AAGCTCCAAGAGAAAGGCATCTACAAAGCCATGAGTGAGTTTGACATCTT

CATCAACTACATAGAAGCCTACATGACAATGAAGATACGAAACTGAGACA

TCAGGGTGGCGACTCTATAGACTCTAGGACATAAATTAGAGGTCTCCAAA

ATCGGATCTGGGGCTCTGGGATAGCTGACCCAGCCCCTTGAGAAACCTTA

TTGTACCTCTCTTATAGAATATTTATTACCTCTGATACCTCAACCCCCAT

TTCTATTTATTTACTGAGCTTCTCTGTGAACGATTTAGAAAGAAGCCCAA

TATTATAATTTTTTTCAATATTTATTATTTTCACCTGTTTTTAAGCTGTT

TCCATAGGGTGACACACTATGGTATTTGAGTGTTTTAAGATAAATTATAA

GTTACATAAGGGAGGAAAAAAAATGTTCTTTGGGGAGCCAACAGAAGCTT

CCATTCCAAGCCTGACCACGCTTTCTAGCTGTTGAGCTGTTTTCCCTGAC

CTCCCTCTAATTTATCTTGTCTCTGGGCTTGGGGCTTCCTAACTGCTACA

AATACTCTTAGGAAGAGAAACCAGGGAGCCCCTTTGATGATTAATTCACC

TTCCAGTGTCTCGGAGGGATTCCCTAACCTCATTCCCCAACCACTTCAT

TCTTGAAAGCTGTGGCCAGCTTGTTATTTATAACAACCTAAATTTGGTTC

TAGGCCGGGCGCGGTGGCTCACGCCTGTAATCCCAGCACTTTGGGAGGCT

GAGGCGGGTGGATCACTTGAGGTCAGGAGTTCCTAACCAGCCTGGTCAAC

ATGGTGAAACCCCGTCTCTACTAAAAATACAAAAATTAGCCGGGCATGGT

GGCGCGCACCTGTAATCCCAGCTACTTGGGAGGCTGAGGCAAGAGAATTG

CTTGAACCCAGGAGATGGAAGTTGCAGTGAGCTGATATCATGCCCCTGTA

CTCCAGCCTGGGTGACAGAGCAAGACTCTGTCTCAAAAAATAAAAATAAA

AATAAATTTGGTTCTAATAGAACTCAGTTTTAACTAGAATTTATTCAATT

CCTCTGGGAATGTTACATTGTTTGTCTGTCTTCATAGCAGATTTTAATTT

TGAATAAATAAATGTATCTTATTCACATC

In various embodiments, human IL-1β is the protein as identified by the NCBI sequence reference NP_000567.1 or an isoform or naturally occurring mutant or variant thereof. A non-limiting example of a human IL-1β amino acid sequence that available under NCBI sequence reference NP_000567.1 is as follows:

(SEQ ID NO: 29)
MAEVPELASEMMAYYSGNEDDLFFEADGPKQMKCSFQDLDLCPLDGGIQL

RISDHHYSKGFRQAASVVVAMDKLRKMLVPCPQTFQENDLSTFFPFIFEE

EPIFFDTWDNEAYVHDAPVRSLNCTLRDSQQKSLVMSGPYELKALHLQGQ

DMEQQVVFSMSFVQGEESNDKIPVALGLKEKNLYLSCVLKDDKPTLQLES

VDPKNYPKKKMEKRFVFNKIEINNKLEFESAQFPNWYISTSQAENMPVFL

GGTKGGQDITDFTMQFVSS

In some embodiments, human IL-1β is the protein as identified by the UniProt reference P01584 or an isoform or naturally occurring mutant or variant thereof. A non-limiting example of a human IL-1β amino acid sequence that is available under UniProt reference P01584 is as follows:

(SEQ ID NO: 30)
MAEVPELASEMMAYYSGNEDDLFFEADGPKQMKCSFQDLDLCPLDGGIQL

RISDHHYSKGFRQAASVVVAMDKLRKMLVPCPQTFQENDLSTFFPFIFEE

EPIFFDTWDNEAYVHDAPVRSLNCTLRDSQQKSLVMSGPYELKALHLQGQ

DMEQQVVFSMSFVQGEESNDKIPVALGLKEKNLYLSCVLKDDKPTLQLES

VDPKNYPKKKMEKRFVFNKIEINNKLEFESAQFPNWYISTSQAENMPVFL

GGTKGGQDITDFTMQFVSS

A non-limiting example of a nucleotide sequence that encodes human IL-1β is as follows (the start and stop codons are underlined and bolded):

(SEQ ID NO: 31)
ACCAAACCTCTTCGAGGCACAAGGCACAACAGGCTGCTCTGGGATTCTCT

TCAGCCAATCTTCATTGCTCAAGTGTCTGAAGCAGCCATGGCAGAAGTAC

CTGAGCTCGCCAGTGAAATGATGGCTTATTACAGTGGCAATGAGGATGAC

TTGTTCTTTGAAGCTGATGGCCCTAAACAGATGAAGTGCTCCTTCCAGGA

CCTGGACCTCTGCCCTCTGGATGGCGGCATCCAGCTACGAATCTCCGACC

ACCACTACAGCAAGGGCTTCAGGCAGGCCGCGTCAGTTGTTGTGGCCATG

GACAAGCTGAGGAAGATGCTGGTTCCCTGCCCACAGACCTTCCAGGAGAA

TGACCTGAGCACCTTCTTTCCCTTCATCTTTGAAGAAGAACCTATCTTCT

TCGACACATGGGATAACGAGGCTTATGTGCACGATGCACCTGTACGATCA

CTGAACTGCACGCTCCGGGACTCACAGCAAAAAAGCTTGGTGATGTCTGG

TCCATATGAACTGAAAGCTCTCCACCTCCAGGGACAGGATATGGAGCAAC

AAGTGGTGTTCTCCATGTCCTTTGTACAAGGAGAAGAAAGTAATGACAAA

ATACCTGTGGCCTTGGGCCTCAAGGAAAAGAATCTGTACCTGTCCTGCGT

GTTGAAAGATGATAAGCCCACTCTACAGCTGGAGAGTGTAGATCCCAAAA

ATTACCCAAAGAAGAAGATGGAAAAGCGATTTGTCTTCAACAAGATAGAA

ATCAATAACAAGCTGGAATTTGAGTCTGCCCAGTTCCCCAACTGGTACAT

CAGCACCTCTCAAGCAGAAAACATGCCCGTCTTCCTGGGAGGGACCAAAG

GCGGCCAGGATATAACTGACTTCACCATGCAATTTGTGTCTTCCTAAAGA

GAGCTGTACCCAGAGAGTCCTGTGCTGAATGTGGACTCAATCCCTAGGGC

TGGCAGAAAGGGAACAGAAAGGTTTTTGAGTACGGCTATAGCCTGGACTT

TCCTGTTGTCTACACCAATGCCCAACTGCCTGCCTTAGGGTAGTGCTAAG

AGGATCCTGTCCATCAGCCAGGACAGTCAGCTCTCTCCTTTCAGGGCC

AATCCCCAGCCCTTTTGTTGAGCCAGGCCTCTCTCACCTCTCCTACTCAC

TTAAAGCCCGCCTGACAGAAACCACGGCCACATTTGGTTCTAAGAAACCC

TCTGTCATTCGCTCCCACATTCTGATGAGCAACCGCTTCCCTATTTATTT

ATTTATTTGTTTGTTTGTTTTATTCATTGGTCTAATTTATTCAAAGGGGG

CAAGAAGTAGCAGTGTCTGTAAAAGAGCCTAGTTTTTAATAGCTATGGAA

TCAATTCAATTTGGACTGGTGTGCTCTCTTTAAATCAAGTCCTTTAATTA

AGACTGAAAATATATAAGCTCAGATTATTTAAATGGGAATATTTATAAAT

GAGCAAATATCATACTGTTCAATGGTTCTGAAATAAACTTCACTGAAG

In certain embodiments, human IL-17A is the protein as identified by the NCBI sequence reference NP_002181.1 or an isoform or naturally occurring mutant or variant thereof. A non-limiting example of a human IL-17A amino acid sequence that is available under NCBI sequence reference NP_002181.1 is as follows:

(SEQ ID NO: 32)
MTPGKTSLVSLLLLLSLEAIVKAGITIPRNPGCPNSEDKNFPRTVMVNLN

IHNRNTNTNPKRSSDYYNRSTSPWNLHRNEDPERYPSVIVVEAKCRHLGC

INADGNVDYHMNSVPIQQEILVLRREPPHCPNSFRLEKILVSVGCTCVTP

IVHHVA

In some embodiments, human IL-17A is the protein as identified by the UniProt reference Q16552 or an isoform or naturally occurring mutant or variant thereof. Non-limiting examples of human IL-17A amino acid sequences available under UniProt reference Q16552 are as follows:

(SEQ ID NO: 33)
MTPGKTSLVSLLLLLSLEAIVKAGITIPRNPGCPNSEDKNFPRTVMVNLN

IHNRNTNTNPKRSSDYYNRSTSPWNLHRNEDPERYPSVIVVEAKCRHLGC

INADGNVDYHMNSVPIQQEILVLRREPPHCPNSFRLEKILVSVGCTCVTP

IVHHVA

A non-limiting example of a nucleotide sequence that encodes human IL-17A is as follows (the start and stop codons are underlined and bolded):

(SEQ ID NO: 34)
GCAGGCACAAACTCATCCATCCCCAGTTGATTGGAAGAAACAACGATGAC

TCCTGGGAAGACCTCATTGGTGTCACTGCTACTGCTGCTGAGCCTGGAGG

CCATAGTGAAGGCAGGAATCACAATCCCACGAAATCCAGGATGCCCAAAT

TCTGAGGACAAGAACTTCCCCCGGACTGTGATGGTCAACCTGAACATCCA

TAACCGGAATACCAATACCAATCCCAAAAGGTCCTCAGATTACTACAACC

GATCCACCTCACCTTGGAATCTCCACCGCAATGAGGACCCTGAGAGATAT

CCCTCTGTGATCTGGGAGGCAAAGTGCCGCCACTTGGGCTGCATCAACGC

TGATGGGAACGTGGACTACCACATGAACTCTGTCCCCATCCAGCAAGAGA

TCCTGGTCCTGCGCAGGGAGCCTCCACACTGCCCCAACTCCTTCCGGCTG

GAGAAGATACTGGTGTCCGTGGGCTGCACCTGTGTCACCCCGATTGTCCA

CCATGTGGCCTAAGAGCTCTGGGGAGCCCACACTCCCCAAAGCAGTTAGA

CTATGGAGAGCCGACCCAGCCCCTCAGGAACCCTCATCCTTCAAAGACAG

CCTCATTTCGGACTAAACTCATTAGAGTTCTTAAGGCAGTTTGTCCAATT

AAAGCTTCAGAGGTAACACTTGGCCAAGATATGAGATCTGAATTACCTTT

CCCTCTTTCCAAGAAGGAAGGTTTGACTGAGTACCAATTTGCTTCTTGTT

TACTTTTTTAAGGGCTTTAAGTTATTTATGTATTTAATATGCCCTGAGAT

AACTTTGGGGTATAAGATTCCATTTTAATGAATTACCTACTTTATTTTGT

TTGTCTTTTTAAAGAAGATAAGATTCTGGGCTTGGGAATTTTATTATTTA

AAAGGTAAAACCTGTATTTATTTGAGCTATTTAAGGATCTATTTATGTTT

AAGTATTTAGAAAAAGGTGAAAAAGCACTATTATCAGTTCTGCCTAGGTA

AATGTAAGATAGAATTAAATGGCAGTGCAAAATTTCTGAGTCTTTACAAC

ATACGGATATAGTATTTCCTCCTCTTTGTTTTTAAAAGTTATAACATGGC

TGAAAAGAAAGATTAAACCTACTTTCATATGTATTAATTTAAATTTTGCA

ATTTGTTGAGGTTTTACAAGAGATACAGCAAGTCTAACTCTCTGTTCCAT

TAAACCCTTATAATAAAATCCTTCTGTAATAATAAAGTTTCAAAAGAAAA

TGTTTATTTGTTCTCATTAAATGTATTTTAGCAAACTCAGCTCTTCCCTA

TTGGGAAGAGTTATGCAAATTCTCCTATAAGCAAAACAAAGCATGTCTTT

GAGTAACAATGACCTGGAAATACCCAAAATTCCAAGTTCTCGATTTCACA

TGCCTTCAAGACTGAACACCGACTAAGGTTTTCATACTATTAGCCAATGC

TGTAGACAGAAGCATTTTGATAGGAATAGAGCAAATAAGATAATGGCCCT

GAGGAATGGCATGTCATTATTAAAGATCATATGGGGAAAATGAAACCCTC

CCCAAAATACAAGAAGTTCTGGGAGGAGACATTGTCTTCAGACTACAATG

TCCAGTTTCTCCCCTAGACTCAGGCTTCCTTTGGAGATTAAGGCCCCTCA

GAGATCAACAGACCAACATTTTTCTCTTCCTCAAGCAACACTCCTAGGGC

CTGGCTTCTGTCTGATCAAGGCACCACACAACCCAGAAAGGAGCTGATGG

GGCAGAACGAACTTTAAGTATGAGAAAAGTTCAGCCCAAGTAAAATAAAA

ACTCAATCACATTCAATTCCAGAGTAGTTTCAAGTTTCACATCGTAACCA

TTTTCGCCC

In certain embodiments, human TNF-α is the protein as identified by the NCBI sequence reference NP_000585.2 or an isoform or naturally occurring mutant or variant thereof. A non-limiting example of a human TNF-α amino acid sequence that is available under NCBI sequence reference NP_000585.2 is as follows:

(SEQ ID NO: 35)
MSTESMIRDVELAEEALPKKTGGPQGSRRCLFLSLFSFLIVAGATTLFCLL

HFGVIGPQREEFPRDLSLISPLAQAVRSSSRTPSDKPVAHVVANPQAEGQL

QWLNRRANALLANGVELRDNQLVVPSEGLYLIYSQVLFKGQGCPSTHVLLT

HTISRIAVSYQTKVNLLSAIKSPCQRETPEGAEAKPWYEPIYLGGVFQLEK

GDRLSAEINRPDYLDFAESGQVYFGIIAL

In some embodiments, human TNF-α is the protein as identified by the UniProt reference P01375 or an isoform or naturally occurring mutant or variant thereof. A non-limiting example of a human TNF-α amino acid sequence that is available under UniProt reference P01375 is as follows:

(SEQ ID NO: 36)
MSTESMIRDVELAEEALPKKTGGPQGSRRCLFLSLFSFLIVAGATTLFCLL

HFGVIGPQREEFPRDLSLISPLAQAVRSSSRTPSDKPVAHVVANPQAEGQL

QWLNRRANALLANGVELRDNQLVVPSEGLYLIYSQVLFKGQGCPSTHVLLT

HTISRIAVSYQTKVNLLSAIKSPCQRETPEGAEAKPWYEPIYLGGVFQLEK

GDRLSAEINRPDYLDFAESGQVYFGIIAL

A non-limiting example of a nucleotide sequence that encodes human TNF-α is as follows (the start and stop codons are underlined and bolded):

(SEQ ID NO: 37)
CAGACGCTCCCTCAGCAAGGACAGCAGAGGACCAGCTAAGAGGGAGAGAAG

CAACTACAGACCCCCCCTGAAAACAACCCTCAGACGCCACATCCCCTGACA

AGCTGCCAGGCAGGTTCTCTTCCTCTCACATACTGACCCACGGCTCCACCC

TCTCTCCCCTGGAAAGGACACCATGAGCACTGAAAGCATGATCCGGGACGT

GGAGCTGGCCGAGGAGGCGCTCCCCAAGAAGACAGGGGGGCCCCAGGGCTC

CAGGCGGTGCTTGTTCCTCAGCCTCTTCTCCTTCCTGATCGTGGCAGGCGC

CACCACGCTCTTCTGCCTGCTGCACTTTGGAGTGATCGGCCCCCAGAGGGA

AGAGTTCCCCAGGGACCTCTCTCTAATCAGCCCTCTGGCCCAGGCAGTCAG

ATCATCTTCTCGAACCCCGAGTGACAAGCCTGTAGCCCATGTTGTAGCAAA

CCCTCAAGCTGAGGGGCAGCTCCAGTGGCTGAACCGCCGGGCCAATGCCCT

CCTGGCCAATGGCGTGGAGCTGAGAGATAACCAGCTGGTGGTGCCATCAGA

GGGCCTGTACCTCATCTACTCCCAGGTCCTCTTCAAGGGCCAAGGCTGCCC

CTCCACCCATGTGCTCCTCACCCACACCATCAGCCGCATCGCCGTCTCCTA

CCAGACCAAGGTCAACCTCCTCTCTGCCATCAAGAGCCCCTGCCAGAGGGA

GACCCCAGAGGGGGCTGAGGCCAAGCCCTGGTATGAGCCCATCTATCTGGG

AGGGGTCTTCCAGCTGGAGAAGGGTGACCGACTCAGCGCTGAGATCAATCG

GCCCGACTATCTCGACTTTGCCGAGTCTGGGCAGGTCTACTTTGGGATCAT

TGCCCTGTGAGGAGGACGAACATCCAACCTTCCCAAACGCCTCCCCTGCCC

CAATCCCTTTATTACCCCCTCCTTCAGACACCCTCAACCTCTTCTGGCTCA

AAAAGAGAATTGGGGGCTTAGGGTCGGAACCCAAGCTTAGAACTTTAAGCA

ACAAGACCACCACTTCGAAACCTGGGATTCAGGAATGTGTGGCCTGCACAG

TGAAGTGCTGGCAACCACTAAGAATTCAAACTGGGGCCTCCAGAACTCACT

GGGGCCTACAGCTTTGATCCCTGACATCTGGAATCTGGAGACCAGGGAGCC

TTTGGTTCTGGCCAGAATGCTGCAGGACTTGAGAAGACCTCACCTAGAAAT

TGACACAAGTGGACCTTAGGCCTTCCTCTCTCCAGATGTTTCCAGACTTCC

TTGAGACACGGAGCCCAGCCCTCCCCATGGAGCCAGCTCCCTCTATTTATG

TTTGCACTTGTGATTATTTATTATTTATTATTTATTTATTTACAGAT

GAATGTATTTATTTGGGAGACCGGGGTATCCTGGGGGACCCAATGTAGGAG

CTGCCTTGGCTCAGACATGTTTTCCGTGAAAACGGAGCTGAACAATAGGCT

GTTCCCATGTAGCCCCCTGGCCTCTGTGCCTTCTTTTGATTATGTTTTTA

AAATATTTATCTGATTAAGTTGTCTAAACAATGCTGATTTGGTGACCAACT

GTCACTCATTGCTGAGCCTCTGCTCCCCAGGGGAGTTGTGTCTGTAATCGC

CCTACTATTCAGTGGCGAGAAATAAAGTTTGCTTAGAAAAGAAAAAAAAAA

AAA

In various embodiments, human IFN-γ is the protein as identified by the NCBI sequence reference NP_000610.2 or an isoform or naturally occurring mutant or variant thereof. A non-limiting example of a human IFN-γ amino acid sequence that is available under NCBI sequence reference NP_000610.2 is as follows:

(SEQ ID NO: 38)
MKYTSYILAFQLCIVLGSLGCYCQDPYVKEAENLKKYFNAGHSDVADNGTL

FLGILKNWKEESDRKIMQSQIVSFYFKLFKNFKDDQSIQKSVETIKEDMNV

KFFNSNKKKRDDFEKLTNYSVTDLNVQRKAIHELIQVMAELSPAAKTGKRK

RSQMLFRGRRASQ

In some embodiments, human IFN-γ is the protein as identified by the UniProt reference P01579 or an isoform or naturally occurring mutant or variant thereof. A non-limiting example of a human IFN-γ amino acid sequence that is available under UniProt reference P01579 is as follows:

(SEQ ID NO: 39)
MKYTSYILAFQLCIVLGSLGCYCQDPYVKEAENLKKYFNAGHSDVADNGTL

FLGILKNWKEESDRKIMQSQIVSFYFKLFKNFKDDQSIQKSVETIKEDMNV

KFFNSNKKKRDDFEKLTNYSVTDLNVQRKAIHELIQVMAELSPAAKTGKRK

RSQMLFRGRRASQ

A non-limiting example of a nucleotide sequence that encodes human IFN-γ is as follows (the start and stop codons are underlined and bolded):

(SEQ ID NO: 40)
CACATTGTTCTGATCATCTGAAGATCAGCTATTAGAAGAGAAAGATCAGTT

AAGTCCTTTGGACCTGATCAGCTTGATACAAGAACTACTGATTTCAACTTC

TTTGGCTTAATTCTCTCGGAAACGATGAAATATACAAGTTATATCTTGGCT

TTTCAGCTCTGCATCGTTTTGGGTTCTCTTGGCTGTTACTGCCAGGACCCA

TATGTAAAAGAAGCAGAAAACCTTAAGAAATATTTTAATGCAGGTCATTCA

GATGTAGCGGATAATGGAACTCTTTTCTTAGGCATTTTGAAGAATTGGAAA

GAGGAGAGTGACAGAAAAATAATGCAGAGCCAAATTGTCTCCTTTTACTTC

AAACTTTTTAAAAACTTTAAAGATGACCAGAGCATCCAAAAGAGTGTGGAG

ACCATCAAGGAAGACATGAATGTCAAGTTTTTCAATAGCAACAAAAAGAAA

CGAGATGACTTCGAAAAGCTGACTAATTATTCGGTAACTGACTTGAATGTC

CAACGCAAAGCAATACATGAACTCATCCAAGTGATGGCTGAACTGTCGCCA

GCAGCTAAAACAGGGAAGCGAAAAAGGAGTCAGATGCTGTTTCGAGGTCGA

AGAGCATCCCAGTAATGGTTGTCCTGCCTGCAATATTTGAATTTTAAATCT

AAATCTATTTATTAATATTTAACATTATTTATATGGGGAATATATTTTTAG

ACTCATCAATCAAATAAGTATTTATAATAGCAACTTTTGTGTAATGAAAAT

GAATATCTATTAATATATGTATTATTTATAATTCCTATATCCTGTGACTGT

CTCACTTAATCCTTTGTTTTCTGACTAATTAGGCAAGGCTATGTGATTACA

AGGCTTTATCTCAGGGGCCAACTAGGCAGCCAACCTAAGCAAGATCCCATG

GGTTGTGTGTTTATTTCACTTGATGATACAATGAACACTTATAAGTGAAGT

GATACTATCCAGTTACTGCCGGTTTGAAAATATGCCTGCAATCTGAGCCAG

TGCTTTAATGGCATGTCAGACAGAACTTGAATGTGTCAGGTGACCCTGATG

AAAACATAGCATCTCAGGAGATTTCATGCCTGGTGCTTCCAAATATTGTTG

-continued

ACAACTGTGACTGTACCCAAATGGAAAGTAACTCATTTGTTAAAATTATCA

ATATCTAATATATATGAATAAAGTGTAAGTTCACAACAAAAAAAAAAAAAA

AAAAAAAAAAAAAAAA

In certain embodiments, human MCP-1 is the protein as identified by the NCBI sequence reference NP_002973.1 or an isoform or naturally occurring mutant or variant thereof. A non-limiting example of a human MCP-1 amino acid sequence that is available under NCBI sequence reference NP_002973.1 is as follows:

(SEQ ID NO: 41)
MKVSAALLCLLLIAATFIPQGLAQPDAINAPVTCCYNFTNRKISVQRLASY

RRITSSKCPKEAVIFKTIVAKEICADPKQKWVQDSMDHLDKQTQTPKT

In some embodiments, human MCP-1 is the protein as identified by the UniProt reference P13500 or an isoform or naturally occurring mutant or variant thereof. A non-limiting example of a human MCP-1 amino acid sequence that is available under UniProt reference P13500 is as follows:

(SEQ ID NO: 42)
MKVSAALLCLLLIAATFIPQGLAQPDAINAPVTCCYNFTNRKISVQRLASY

RRITSSKCPKEAVIFKTIVAKEICADPKQKWVQDSMDHLDKQTQTPKT

A non-limiting example of a nucleotide sequence that encodes human MCP-1 is as follows (the start and stop codons are underlined and bolded):

(SEQ ID NO: 43)
GAGGAACCGAGAGGCTGAGACTAACCCAGAAACATCCAATTCTCAAACTGA

AGCTCGCACTCTCGCCTCCAGCATGAAAGTCTCTGCCGCCCTTCTGTGCCT

GCTGCTCATAGCAGCCACCTTCATTCCCCAAGGGCTCGCTCAGCCAGATGC

AATCAATGCCCCAGTCACCTGCTGTTATAACTTCACCAATAGGAAGATCTC

AGTGCAGAGGCTCGCGAGCTATAGAAGAATCACCAGCAGCAAGTGTCCCAA

AGAAGCTGTGATCTTCAAGACCATTGTGGCCAAGGAGATCTGTGCTGACCC

CAAGCAGAAGTGGGTTCAGGATTCCATGGACCACCTGGACAAGCAAACCCA

AACTCCGAAGACTTGAACACTCACTCCACAACCCAAGAATCTGCAGCTAAC

TTATTTTCCCCTAGCTTTCCCCAGACACCCTGTTTTATTTTATTATAATGA

ATTTTGTTTGTTGATGTGAAACATTATGCCTTAAGTAATGTTAATTCTTAT

TTAAGTTATTGATGTTTTAAGTTTATCTTTCATGGTACTAGTGTTTTTAG

ATACAGAGACTTGGGGAAATTGCTTTTCCTCTTGAACCACAGTTCTACCCC

TGGGATGTTTTGAGGGTCTTTGCAAGAATCATTAATACAAAGAATTTTTTT

TAACATTCCAATGCATTGCTAAAATATTATTGTGGAAATGAATATTTTGTA

ACTATTACACCAAATAAATATATTTTTGTACAAAAAAAAAAAAAAA

In various embodiments, human MIP-1α is the protein as identified by the NCBI sequence reference NP_002974.1 or an isoform or naturally occurring mutant or variant thereof. A non-limiting example of a human MIP-1α amino acid sequence that is available under NCBI sequence reference NP_002974.1 is as follows:

(SEQ ID NO: 44)
MQVSTAALAVLLCTMALCNQFSASLAADTPTACCFSYTSRQIPQNFIADYF

ETSSQCSKPGVIFLTKRSRQVCADPSEEWVQKYVSDLELSA

In some embodiments, human MIP-1α is the protein as identified by the UniProt reference P10147 or an isoform or naturally occurring mutant or variant thereof. A non-limiting example of a human MIP-1α amino acid sequence that is available under UniProt reference P10147 is as follows:

(SEQ ID NO: 45)
MQVSTAALAVLLCTMALCNQFSASLAADTPTACCFSYTSRQIPQNFIADYF

ETSSQCSKPGVIFLTKRSRQVCADPSEEWVQKYVSDLELSA

A non-limiting example of a nucleotide sequence that encodes human MIP-1α is as follows (the start and stop codons are underlined and bolded):

(SEQ ID NO: 46)
AGCTGGTTTCAGACTTCAGAAGGACACGGGCAGCAGACAGTGGTCAGTCCT

TTCTTGGCTCTGCTGACACTCGAGCCCACATTCCGTCACCTGCTCAGAATC

ATGCAGGTCTCCACTGCTGCCCTTGCTGTCCTCCTCTGCACCATGGCTCTC

TGCAACCAGTTCTCTGCATCACTTGCTGCTGACACGCCGACCGCCTGCTGC

TTCAGCTACACCTCCCGGCAGATTCCACAGAATTTCATAGCTGACTACTTT

GAGACGAGCAGCCAGTGCTCCAAGCCCGGTGTCATCTTCCTAACCAAGCGA

AGCCGGCAGGTCTGTGCTGACCCCAGTGAGGAGTGGGTCCAGAAATATGTC

AGCGACCTGGAGCTGAGTGCCTGAGGGGTCCAGAAGCTTCGAGGCCCAGCG

ACCTCGGTGGGCCCAGTGGGGAGGAGCAGGAGCCTGAGCCTTGGGAACATG

CGTGTGACCTCCACAGCTACCTCTTCTATGGACTGGTTGTTGCCAAACAGC

CACACTGTGGGACTCTTCTTAACTTAAATTTTAATTTATTTATACTATTTA

GTTTTTGTAATTTATTTTCGATTTCACAGTGTGTTTGTGATTGTTTGCTCT

GAGAGTTCCCCTGTCCCCTCCCCCTTCCCTCACACCGCGTCTGGTGACAAC

CGAGTGGCTGTCATCAGCCTGTGTAGGCAGTCATGGCACCAAAGCCACCAG

ACTGACAAATGTGTATCGGATGCTTTTGTTCAGGGCTGTGATCGGCCTGGG

GAAATAATAAAGATGCTCTTTTAAAAGGTAAAAAAAAAAAAAAAAAAAA

In certain embodiments, human MIP1β is the protein as identified by the NCBI sequence reference NP_002975.1 or an isoform or naturally occurring mutant or variant thereof. A non-limiting example of a human MIP1β amino acid sequence that is available under NCBI sequence reference NP_002975.1 is as follows:

(SEQ ID NO: 47)
MKLCVTVLSLLMLVAAFCSPALSAPMGSDPPTACCFSYTARKLPRNFVVDY

YETSSLCSQPAVVFQTKRSKQVCADPSESWVQEYVYDLELN

In some embodiments, human MIP1β is the protein as identified by the UniProt reference P13236 or an isoform or naturally occurring mutant or variant thereof. A non-limiting example of a human MIP1β amino acid sequence that is available under UniProt reference P13236 is as follows:

(SEQ ID NO: 48)
MKLCVTVLSLLMLVAAFCSPALSAPMGSDPPTACCFSYTARKLPRNFVVDY

YETSSLCSQPAVVFQTKRSKQVCADPSESWVQEYVYDLELN

A non-limiting example of a nucleotide sequence that encodes human MIP1β is as follows (the start and stop codons are underlined and bolded):

(SEQ ID NO: 49)
AGCACAGGACACAGCTGGGTTCTGAAGCTTCTGAGTTCTGCAGCCTCACCT

CTGAGAAAACCTCTTTTCCACCAATACCATGAAGCTCTGCGTGACTGTCCT

GTCTCTCCTCATGCTAGTAGCTGCCTTCTGCTCTCCAGCGCTCTCAGCACC

AATGGGCTCAGACCCTCCCACCGCCTGCTGCTTTTCTTACACCGCGAGGAA

GCTTCCTCGCAACTTTGTGGTAGATTACTATGAGACCAGCAGCCTCTGCTC

CCAGCCAGCTGTGGTATTCCAAACCAAAAGAAGCAAGCAAGTCTGTGCTGA

TCCCAGTGAATCCTGGGTCCAGGAGTACGTGTATGACCTGGAACTGAACTG

AGCTGCTCAGAGACAGGAAGTCTTCAGGGAAGGTCACCTGAGCCCGGATGC

TTCTCCATGAGACACATCTCCTCCATACTCAGGACTCCTCTCCGCAGTTCC

TGTCCCTTCTCTTAATTTAATCTTTTTTATGTGCCGTGTTATTGTATTAGG

TGTCATTTCCATTATTTATATTAGTTTAGCCAAAGGATAAGTGTCCCCTAT

GGGGATGGTCCACTGTCACTGTTTCTCTGCTGTTGCAAATACATGGATAAC

ACATTTGATTCTGTGTGTTTTCATAATAAAACTTTAAAATAAAATGCAGAC

AGTT

Non-Limiting Examples of Confection-Based Compositions

Aspects of the present subject matter relate to confection compositions comprising inactivated, non-viable, or dead *Bacillus coagulans* bacteria or particles comprising such bacteria. The confection compositions are suitable for human or animal consumption. As used herein, a "confection" or "confection composition" includes food items that are rich in sugar or artificial sweeteners. Depending on context, the words "candy" or "sweet" may be used synonymously the term "confectionery." In various embodiments, candy may be made by dissolving sugar in a liquid (such as water or milk) to form a syrup, which is boiled until it reaches the desired concentration or starts to caramelize. In some embodiments, the type of candy depends on the ingredients and how long the mixture is boiled, while the final texture of candy depends on the sugar concentration. In certain embodiments, as the syrup is heated, it boils, water evaporates, the sugar concentration increases, and the boiling point rises. Thus, in various embodiments, boiling temperature corresponds to a particular sugar concentration. In some embodiments, higher temperatures and greater sugar concentrations result in hard, brittle candies, while lower temperatures result in softer candies. In certain embodiments, the name of a candy may come from the process used to test the syrup before thermometers became affordable: a small spoonful of syrup was dropped into cold water, and the characteristics of the resulting lump were evaluated to determine the concentration of the syrup. Long strings of hardened sugar indicate "thread" stage, while a smooth lump indicates "ball" stages, with the corresponding hardness described. The "crack" stages are indicated by a ball of candy so brittle that the rapid cooling from the water literally causes it to crack. Candy comes in an endless variety of textures from soft and chewy to hard and brittle.

There are a variety of categories and types of confections. Non-limiting examples are described herein. In various embodiments, hard sweets are based on sugars cooked to the hard-crack stage, including suckers, lollipops, jawbreakers (or gobstoppers), lemon drops, peppermint drops and disks, candy canes, rock candy, etc. Hard sweets also include candies often mixed with nuts, such as brittle. Others contain flavorings including coffee, such as Kopiko. In certain embodiments, fudge is a confection of milk and sugar boiled to the soft-ball stage. In some embodiments, toffee (or Taffy or Tuffy) is based on sugars cooked to the soft-ball stage and then pulled to create an elastic texture. In various embodiments, tablet is a crumbly milk-based soft and hard candy, based on sugars cooked to the soft-ball stage, and comes in several forms, such as wafers and heart shapes. Liquorice, which contains extract of the liquorice root, is chewier and more resilient than gum/gelatin candies, but still designed for swallowing. Other types of confection include chocolates, marshmallow, marzipan, and divinity. Jelly candies include those based on sugar and starch, pectin, gum, or gelatin, e.g., jelly beans, gumdrops, jujubes, cola bottles, and gummies. In some embodiments, a jelly candy comprises a gummi candy/confection. In certain embodiments, the gummi candy may comprise a gelatin-based gummi candy. In various embodiments, the gummi candy comprises a hydrocolloid such as one or more or any combination of the following: gelatin, gellan gum, xanthan gum, pectin, carrageenan, cellulose gum, gum arabic, and modified starch. In certain embodiments, a gelatin-based gummi candy comprises at least about 5%, 10%, 15%, 20%, or 25% gelatin by weight, at least about 5%, 10%, 15%, 20%, 25%, 30%, 35%, 40%, 45%, 50%, 55%, 60%, 65%, 70%, or 75% monosaccharide or disaccharide sugar by weight, at least about 5%, 10%, 15%, 20%, 25%, 30%, 35%, 40%, 45%, or 50% starch (e.g., modified starch) or corn syrup by weight, at least about 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% pectin by weight, at least about 0.1%, 0.2%, 0.3%, 0.4%, 0.5%, 0.6%, 0.7%, 0.8%, 0.9%, 1.0%, 1.1%, 1.2%, 1.3%, 1.4%, or 1.5% gellan gum by weight, and/or at least about 5%, 10%, 15%, 20%, or 25% water by weight.

Suitable gummi confections include those in the shapes of bears, rings, worms, frogs, snakes, hamburgers, cherries, sharks, penguins, hippos, lobsters, octopuses, apples, peaches, oranges, and spiders. Suitable gummi bear sizes range from the standard candy size (or smaller), to gummi bears that weigh several kilograms. Gummi confections come in a variety of flavors, including raspberry, orange, strawberry, pineapple, and lemon.

A non-limiting example of a traditional gummi confection (e.g., gummi bears) is made from sugar, glucose syrup, starch, flavoring, food coloring, citric acid, and gelatin. Suitable gelling agents and hydrocolloids can be selected by one of ordinary skill in the art. Examples include gums, carrageenan, gelatin, pectin, high methoxy pectin, alginates, and agar. One of ordinary skill in the art can select a suitable gelling agent or hydrocolloid depending on the desired final texture of the starch molded piece. There are some gummi confections made with pectin or starch instead of gelatin, making them suitable for vegetarians. An exemplary organic gummi confection is made with most all natural ingredients, such as organic tapioca syrup, organic evaporated cane juice, gelatin, organic grape juice concentrate, citric acid, lactic acid, ascorbic acid, colors added (black, carrot juice concentrate, turmeric, annatto), natural flavors, organic sunflower oil, and carnauba wax.

In various embodiments, large sour gummi bears are larger and flatter than traditional gummi bears, have a softer texture, and include fumaric acid or other acid ingredients to produce a sour flavor. In some embodiments, sour "gummies" are produced by forming a sweet, flavored, and chewy core and subsequently dusting the exterior with a food acid, such as citric acid. In certain embodiments, the gelling ingredient in the core of these products is gelatin or pectin. In various embodiments, the acidic exterior is applied by use of a wetting agent or food adhesive. Some manufacturers produce sour bears with a different texture, based on starch instead of gelatin. Typically, starch produces a shorter (cleaner bite, less chewy) texture than gelatin.

Confection-based compositions, such as those described herein, may be made from a variety of ingredients known to those skilled in the art. In some embodiments, the confection-based compositions are prepared by combining confection ingredients and a liquid, e.g., water or milk. In certain embodiments, the composition is prepared by combining confection ingredients and a liquid, and heating the resulting combination. Optionally, the combination is heated (heat-processed) using applied heat, a flame, or a microwave. In various embodiments, the confection-based composition is boiled in hot water, e.g., stovetop boiling, addition of boiling water to a container, or microwaving the confection-based composition along with water. In some embodiments, boiling water (about 100° C.) is added to a combination of confection ingredients and inactivated, non-viable, or dead *Bacillus coagulans* bacteria or particles comprising such bacteria. In embodiments, viable *Bacillus coagulans* bacteria (e.g., spores and/or vegetative bacteria) are combined with one or more confection ingredients, and the process of producing the confection inactivates or kills the *Bacillus coagulans* bacteria (e.g., in an amount disclosed herein).

In certain embodiments, mass production of gummi confection (e.g., gummi bears) includes mixing the gummi confection ingredients and pouring the resulting mixture into many starched-lined (e.g., corn starch-lined) trays/molds. In various embodiments, the corn starch prevents the gummy bears from sticking to the mold and lets them release easily once they are set. In some embodiments, first, the desired character molds are created and, if necessary, duplicated with a machine. Optionally, starch powder is applied to the character molds. In certain embodiments, gummi confection ingredients, such as sugar, glucose syrup, gelatin, and water are mixed together and heated. In various embodiments, the ingredients are mixed with colors and flavors that give the bears their signature look and taste. In some embodiments, the molten gelatin mixture is poured into the molds and allowed to cool and set prior to packaging or consumption. In certain embodiments, the gummi confection is subsequently heated and placed in a large drum tumbler to apply a composition of isolated inactivated, non-viable, or dead *Bacillus coagulans* bacteria, or particles comprising such bacteria, and a sweetener (e.g., a sugar).

In a non-limiting example, as described in WO/2009/102575, production of a gummi confection includes the following:

A colloid batch and a puree batch are formed and combined with corn syrup and sugar to form a base slurry. The colloid batch comprises a solution of the gelling agent in water at a level of from 5 to 15% by weight of the gelling agent, more preferably from 7 to 12% of the gelling agent based on the total weight of the colloid batch. The colloid batch is held at a temperature of 170 to 190° F. The puree batch preferably comprises water, fruit puree and/or high fructose corn syrup or other sweeteners, thin boiling starch, and sodium citrate. It is held at a temperature of from 65 to 75° F. Preferably, the fruit puree has a Brix of from 10 to 45, more preferably from 25 to 40. Optionally, the puree batch includes a plurality of fruit purees. The fruit puree comprises a typical fruit puree, a fruit juice, or a fruit powder. The puree batch comprises from 30 to 40% by weight water, from 0 to 40% by weight fruit puree, from 0 to 40% by weight high fructose corn syrup, from 25 to 35% by weight thin boiling starch, and from 0.0 to 2.0% by weight sodium citrate. In a mixing kettle from 25 to 40% by weight of additional corn syrup is combined with from 15 to 40% by weight of fine granulated sugar, from 10 to 15% by weight of the colloid batch and from 20 to 30% by weight of the puree batch to form the base slurry. Preferably, the corn syrup is approximately 42 DE corn syrup, however, as would be understood by one of ordinary skill in the art other DE corn syrups could be used. The base slurry components are completely mixed and held at 130 to 150° F. in a holding tank. The base slurry is then cooked to bring the Brix to from 70 to 85 Brix, more preferably to a Brix of from 75 to 80. In one embodiment the base slurry is passed through a coil cooker and heated to a temperature of from 250 to 325° F. to cook it.

Other cooking methods will be known to those of ordinary skill in the art. In some embodiments, the cooked base slurry is preferably subjected to vacuum to further increase the Brix into the desired range. The cooked base slurry is held at approximately 200° F. until used.

In various embodiments, an acidulant solution is added along with color and flavor to the cooked base slurry just prior to deposition in the starch molds. In certain embodiments, the acidulant solution comprises ascorbic acid present in an amount of from 15 to 20% by weight, citric acid present in an amount of from 10 to 20% by weight, and malic acid present in an amount of from 5 to 10% by weight with the remainder comprising water. As would be understood by one of ordinary skill in the art, other edible acids could be used in place of or in addition to those listed. In some embodiments, 95 to 97% by weight of cooked base slurry is combined with from 2 to 3% by weight of the acidulant solution and the remainder comprises flavors and colors. Optionally, the acidulant solution is used to bring the pH of the base slurry to from 2.6 to 3.2. One of ordinary skill in the art would have no difficulty selecting suitable colors and flavors. In certain embodiments, the combined mixture is then deposited into starch molds, e.g., using a Mogul starch molding machine. Such starch molding machines are well known by those of ordinary skill in the art. In some embodiments, from 0.3 to 3 grams of the base slurry is deposited into each mold cavity. In various embodiments, the starch trays with deposited base slurry are transferred to a drying room where there are held for 12 to 48 hours. Optionally, the trays are first held at a temperature of from 130 to 150° F. for from 10 to 15 hours, and then cooled to 70 to 80° F. and held at that temperature for from 6 to 12 hours. In certain embodiments, the gelled starch molded food pieces are then removed from the trays, and the starch is recycled.

Compositions comprising chocolate and inactivated, non-viable, or dead *Bacillus coagulans* bacteria or particles comprising such bacteria are included herein. Chocolate has become one of the most popular food types and flavors in the world, and a vast number of foodstuffs involving chocolate have been created. Gifts of chocolate molded into different shapes have become traditional on certain holidays. Chocolate is also used in cold and hot beverages such as chocolate milk and hot chocolate.

The chocolate may be, e.g., white, plain, dark, or milk chocolate. The classification depends upon the amount of cocoa solids present in the formulation. For example, plain chocolate may have a high percentage of cocoa solids (minimum 30%, and not less than 12% dry, non-fat cocoa solids), milk chocolate may have a lower cocoa solids content (minimum 25%, and not less than 2.5% dry, non-fat cocoa solids), and white chocolate may be prepared from cocoa butter (minimum 20%) and not less than 14% milk solids. As used herein, "chocolate" includes any preparation of (e.g., composition comprising) dry cocoa solids, non-fat cocoa solids and/or cocoa butter. Non-limiting examples of chocolate compositions include products obtained from cocoa nib, cocoa mass, cocoa, fat-reduced cocoa or any combination of two or more thereof and a sugar such as sucrose, with or without the addition of extracted cocoa butter. In some embodiments the chocolate composition contains not less than 35% total dry cocoa solids, including not less than 14% dry non-fat cocoa solids and not less than 18% permitted cocoa butter.

Non-limiting examples of chocolate compositions include coatings made from sugars, cocoa powder and/or milk solids, and/or cocoa liquor combined with vegetable fats other than cocoa butter. In various embodiments, the final chocolate formulation may be used for, e.g., coatings, molded products or panned products, and may or may not be tempered before use.

In some embodiments, a formulation may be an edible confectionery end-product in itself or may be further processed to produce such an end-product. In certain embodiments, the resulting product may be prepared for sale under ambient or low temperature conditions. Non-limiting examples of products for sale at low temperature conditions include frozen and chilled desserts, as well as confectioneries at a low temperature, such as for example of from −25° C. to +15° C., suitably from −20° C. to +5° C., to be consumed at an ambient temperature. Such low temperature products may include but are not limited to ice cream (e.g., milk- or vegetable-fat based ice cream).

In various embodiments, a chocolate formulation may also simply comprise a chocolate fat phase containing a total fat content, e.g., of at least 25% w/w prior to admixing with the concentrated sugar syrup. Suitable ranges of total fat content include, e.g., from 25% to 60% w/w, or 25% to 45% w/w, or 28% to 35% w/w. In some embodiments, such chocolate formulations are further processed into a final confectionery product. In certain embodiments, the final fat content range in the finished formulation may be at least 10% w/w or in the range of from 15% to 45% w/w or from 25% to 35% w/w. These examples should not be construed as being limiting.

Exemplary methods for formulating chocolate are provided in, e.g., European Patent No. EP 0958747B1, granted Nov. 3, 2004; U.S. Pat. No. 4,446,166, issued May 1, 1984; and U.S. Pat. No. 5,527,556, issued Jun. 18, 1996, the entire contents of each of which are incorporated herein by reference.

Confections provided herein also include "ganache" which is conventionally used as a short shelf-life filling for truffles or as a topping for confections. Ganache is the confectioner's term for a phase-inverted (i.e. oil-in-water) chocolate preparation. Ganache has a smooth, glossy texture and appearance, and a rich chocolate or milk chocolate taste.

A ganache may also be produced from white chocolate in a similar way. An exemplary moisture content for ganache from 10-40% w/w. In some embodiments, a ganache cannot be utilized in processing in the same way as conventional chocolate and its soft texture characteristics render it unsuitable for the majority of enrobing, molding or pan-coating operations.

In certain embodiments, a confection provided herein further comprises a sweetener (e.g., a granulated or powder sugar) coating on the exterior surface thereof. The sweeteners can comprise, e.g., one or more monosaccharides or disaccharides. Non-limiting examples include sugar, sucrose, invert sugar, dextrose, lactose, honey, malt syrup, malt syrup solids, maltose, fructose, granular fructose, maple syrup, rice syrup, rice syrup solids, sorghum syrup, refiners syrup, corn syrup, corn syrup solids, high fructose corn syrup, molasses, and any combination thereof. In some embodiments, the sugar comprises cane sugar, beet sugar, date sugar, sucanat, granulated fructose or an artificial sweetener (e.g., a saccharin-containing sweetener such as Sweet-n-Low®, an aspartame- and/or neotame-containing sweetener such as NutraSweet®, or a sweetener containing aspartame, acesulfame potassium, dextrose, and maltodextrin such as Equal®). Additional artificial sweeteners include acesulfame K, aspartame, sucralose, d-tagatose, and combinations thereof.

Dry Mixes and Addition of Inactivated, Non-Viable or Dead *Bacillus coagulans* to Food Compositions Compositions provided herein include a dry mix comprising inactivated, non-viable, or dead *Bacillus coagulans* bacteria, or particles comprising such bacteria, for inclusion within or addition to the surface of compositions. In certain embodiments, the dry mix may be between 1% and 50% inactivated, non-viable, or dead *Bacillus coagulans* bacteria, e.g., about 5%, about 10%, about 15%, about 20%, about 25%, about 35%, about 45%, or about 50% inactivated, non-viable, or dead *Bacillus coagulans* bacteria. In some embodiments, the dry mix may be about 15% inactivated, non-viable, or dead *Bacillus coagulans* bacteria and 85% sugar. For example, about 100 pounds of dry mix may contain about 15 pounds of inactivated, non-viable, or dead *Bacillus coagulans* bacteria and about 85 pounds of other edible matter such as starch or sugar.

In various embodiments, when included in a composition, the dry mix may be between about 1% and about 50% by weight of the composition, e.g., about 1% to about 20%, about 5% to about 15%; about 6%, about 7%, about 8%, about 9%, or about 10% by weight of the composition. For example, a 3 gram composition may contain about 7% dry mix by weight of the composition.

In some embodiments, inactivated, non-viable, or dead *Bacillus coagulans* bacteria are added directly to the composition ingredients prior to heating, molding, and subsequent cooling of the confection.

Non-Limiting Examples of Tea Compositions

In an aspect, a tea beverage composition comprising inactivated, non-viable, or dead *Bacillus coagulans* bacteria, or particles comprising such bacteria, is provided. In various embodiments, tea is a beverage made by steeping dehydrated plant matter such as leaves, buds, roots or twigs of a plant in water. In some embodiments, tea is the combination of an instant tea mix (e.g., a powder) with water. In certain embodiments, plant matter is steeped in hot water for a few (e.g. about or at least about 1, 2, 3, 4, 5, 6, 7, 8, 9, or 10 minutes, or about 1-5, 2-5, 3-5, 4-5, or 1-10 minutes). In various embodiments, a tea composition provided herein comprises dried plant matter used for making tea. In some embodiments, a tea composition provided herein comprises an instant tea mix (e.g., a dry powder). In certain embodiments, the tea is instant tea or brewable tea.

In various embodiments, the plant mater is from a *Camellia sinensis* plant. Non-limiting examples of tea include black tea, oolong tea, green tea, yellow tea, and white tea. In certain embodiments, the tea is decaffeinated tea.

In some embodiments, instant tea includes a concentrate or dehydrate of brewed tea. In certain embodiments, an instant tea formulation does not contain vegetative matter.

In various embodiments, the tea is a blend of tea. In some embodiments, a blend of tea is prepared by adding tea from different plants, e.g., a tea from a plant such as *Camellia sinensis* and a plant other than *Camellia sinensis*. For example, the popular Earl Grey tea is black tea with bergamot, while Jasmine tea is Chinese tea with Jasmine.

In certain embodiments, a tea composition comprises herbal tea. In various embodiments, a herb is characterized as a small, seed bearing plant with fleshy, rather than woody, parts. In addition to herbaceous perennials, herbs may include trees, shrubs, annuals, vines, and more primitive plants, such as ferns, algae, and/or mosses. Herbs are often valued for their flavor, fragrance, medicinal and healthful qualities, economic and industrial uses, pesticidal properties, and coloring materials (e.g., as dyes). In some embodiments, a herbal tea is an infusion of vegetative matter other than from a *Camellia sinensis* plant. In certain embodiments, herbal tea is made with fresh or dried flowers, fruit, leaves, seeds or roots, e.g., by pouring hot (such as boiling) water over the plant parts and letting them steep for a few (e.g. about or at least about 1, 2, 3, 4, 5, 6, 7, 8, 9, or 10 minutes, or about 1-5, 2-5, 3-5, 4-5, or 1-10 minutes) minutes. In various embodiments, herbal tea is made with dried leaves, flowers, fruit, or seeds of a medicinal plant. In some embodiments, seeds and/or roots are boiled on a stove or microwaved. In certain embodiments, the herbal tea is then strained and sweetened if so desired. Non-limiting examples of herbal teas include Anise tea, roasted barley tea, Bissap tea, Cannabis tea, Catnip tea, Cerasse tea, Chamomile tea, Chrysanthemum tea (made from dried flowers), Citrus peel tea (including bergamot, lemon and orange peel), roasted corn tea, Echinacea tea, Essiac tea (a blended herbal tea), Fennel tea, Gentian tea, Ginger root tea, Ginseng tea, Greek Mountain Tea (made from a variety of the *Sideritis syriaca* plant), Hibiscus tea (often blended with rose hip), Honeybush tea, Horehound tea, Jiaogulan tea, Kava root tea, Labrador tea, Lapacho tea, Lemon grass tea, Licorice root tea, Lime blossom tea, Lotus flower tea, Mate tea, Mate de coca tea, Mint tea, European mistletoe tea, Neem leaf tea, Nettle leaf tea, Red raspberry leaf tea, Toasted rice tea, Rooibos (Red Bush or red) tea, Rose hip tea (often blended with hibiscus), Rosemary tea, Sage tea, Sassafras tea, Skullcap tea, Staghorn Sumac tea, Stevia tea, Thyme tea, Tulsi tea, *Uncaria tomentosa* tea (Cats Claw), Valerian tea, Vervain tea, Vetiver tea, Roasted wheat tea, Wong Logat tea, Woodruff tea, Yarrow tea, Yuen Kut Lam Kam Wo Tea, and Tan Ngan Lo herbal tea.

In some embodiments, tea comprises lichen or a fungus.

In various embodiments, the tea comprises loose plant matter (e.g., the tea is not in a tea bag). In some embodiments, the tea may be placed in an infuser or strainer. In certain embodiments, the tea composition is within a tea bag. A tea bag consists of two parts, the tea and the bag. Non-limiting examples of tea bags include those of a porous silk, paper, cotton, or nylon bag with tea inside that is used for brewing tea. Inactivated, non-viable, or dead *Bacillus coagulans* bacteria (or particles comprising non-viable, or dead *Bacillus coagulans* bacteria) may be added to the tea in any way, e.g., loosely within, on or in a tea bag, and/or on plant matter (e.g., adhered to or loosely in combination with plant matter). In some embodiments, a tea bag comprises dehydrated plant matter obtained from *Camellia sinensis*. In some embodiments, a tea bag comprises dehydrated plant matter obtained from a plant other than *Camellia sinensis*. In some embodiments, the dehydrated plant matter comprises dried leaves, buds, roots, and/or twigs.

Additional non-limiting examples of non-bacterial ingredients that may be combined with inactivated, non-viable, or dead *Bacillus coagulans* bacteria (or particles comprising non-viable, or dead *Bacillus coagulans* bacteria) include coffee beans or fragments thereof, coffee powder, chocolate powder, and cocoa powder. Non-limiting examples of beverage compositions include coffee, hot chocolate, and hot cocoa. In some embodiments, the coffee is instant coffee or brewable coffee. In certain embodiments, the coffee is decaffeinated coffee. In various embodiments, a beverage composition includes a dairy product, a non-dairy creamer, a flavored creamer, a flavor extract, a natural sweetener (e.g., stevia), or an artificial sweetener such as sucralose or granulated saccharin. In some embodiments, inactivated, non-viable, or dead *Bacillus coagulans* bacteria (or particles comprising non-viable, or dead *Bacillus coagulans* bacteria) are in the form of spray-dried powder is added directly to the coffee (e.g. ground coffee beans or freeze-dried brewed coffee crystals or powder) itself. In certain embodiments, inactivated, non-viable, or dead *Bacillus coagulans* bacteria (or particles comprising non-viable, or dead *Bacillus coagulans* bacteria) are in the form of powder is mixed with the coffee.

Non-Limiting Examples of Soups and Grain-Containing Compositions

Included herein are cooked and uncooked compositions comprising a grain or a portion or processed product thereof and inactivated, non-viable, or dead *Bacillus coagulans* bacteria or particles comprising such bacteria. In some embodiments, the grain is an intact grain or portion thereof, e.g., a grain of a grain of wheat, a grain of rice, a grain of quinoa, a grain of fonio, a grain of barley, a grain of corn, a grain of buckwheat, a grain of rye, a grain of sorghum, a grain of millet, a grain of triticale, or a grain of teff. In certain embodiments, the grain is, e.g., husked but grain not crushed, cracked, or ground. In various embodiments, the grain is processed, e.g., altered from its naturally-occurring state. In some embodiments, the grain is husked, crushed, cracked, or ground. In certain embodiments, the grain is in the form of flour or a composition made from further manipulation of a grain-based flour. As used herein, the term "grain" includes grain-like seeds such as buckwheat. In various embodiments, a grain is a small, hard seed, especially the seed of a food plant such as wheat, corn, rye, oats, rice, or millet. Non-limiting examples of grains include wheat, rice, quinoa, fonio, barley, corn, buckwheat, rye, sorghum, millet, triticale, and teff. Non-limiting examples of wheat include hard red winter wheat, hard red spring wheat, soft red winter wheat, soft white wheat, hart white wheat, and durum wheat. Non-limiting examples of cooked compositions include pasta, oatmeal, and grits. Non-limiting examples of pastas include egg pasta, spaghetti (solid, thin cylinders), macaroni (tubes or hollow cylinders), fusilli (spiral-shaped), lasagna (sheets), tagliatelle (flat ribbons), vermicelli (thin spaghetti), ravioli (filled pasta), spatzle, gnocchi, penne rigate (furrowed cylinder-shaped pasta), penne lisce (smooth cylinder-shaped pasta), rotini (corkscrew-shaped pasta), and rigatoni (tube-shaped pasta).

In some embodiments, the composition comprises a dry mix grain-based composition comprising a grain and inactivated, non-viable, or dead *Bacillus coagulans* bacteria or particles comprising such bacteria. Also provided are compositions comprising a dry mix for soup comprising a dehydrated matter and inactivated, non-viable, or dead *Bacillus coagulans* bacteria or particles comprising such bacteria.

Also provided are methods of making a grain-based composition comprising providing a grain-containing base mix and a liquid portion; mixing the grain-containing base mix and the liquid portion to form a batter or dough; combining viable *Bacillus coagulans* with the batter or dough; and heat processing the batter or dough at a temperature that kills all or substantially all of the viable *Bacillus coagulans* to cook the grain-based composition. In various embodiments, the liquid portion include water or milk. In some embodiments, the viable *Bacillus coagulans* is in the form of a spore. In some embodiments, the viable *Bacillus coagulans* is in the form of a vegetative cell.

Non-limiting examples of grain-based compositions include pasta, oatmeal, grits, and cereal. Common (non-limiting) varieties of pasta include tubular pasta, straight round rod pasta, ribbon pasta, micro pasta, stuffed pasta, irregular-shaped pasta, spaghetti (solid, thin cylinders), macaroni (tubes or hollow cylinders), fusilli (spiral-shaped), lasagna (sheets), tagliatelle (flat ribbons), vermicelli (thin spaghetti), and ravioli (filled pasta), penne (cylinder-shaped pasta), rotini (corkscrew-shaped pasta), rigatoni (tube-shaped pasta), noodles, and spatzle. In some embodiments, the pasta is dried. In certain embodiments, the pasta is fresh. In various embodiments, the pasta includes egg (egg pasta). In some embodiments, the pasta does not include egg.

Many ingredients may be used to make pasta dough, ranging from a simple flour and water mixture, to those that call for the addition of eggs, spices and cheeses, or even squid ink to the dough. In certain embodiments, the pasta contains a filling, e.g., cheese, vegetables, fruit, and/or meat. In various embodiments, dry pasta is made from durum wheat flour, farina flour, or semolina flour. Some pasta varieties, such as pizzoccheri, are made from buckwheat flour.

In some embodiments, a composition provided herein comprises gnocchi (often considered to be pasta, although it can have quite different ingredients such as milled potatoes).

Also provided are grain-based compositions in the form of oatmeal with inactivated, non-viable, or dead *Bacillus coagulans* bacteria or particles comprising such bacteria. Oatmeal includes products of ground oat groats (e.g., oatmeal, cornmeal, peasemeal, etc.) and porridge made from such products (also called oatmeal cereal). In some embodiments, oatmeal includes other products made from oat groats, such as cut oats, crushed oats, and rolled oats. In certain embodiments, the groats are coarsely ground to make oatmeal, or cut into small pieces to make steel-cut oats, or steamed and rolled to make rolled oats. In various embodiments relating to rolled oats, oat groats are steamed, pressed with a roller, and dried. In some embodiments, the oatmeal is instant oatmeal. In certain embodiments, instant oatmeal is pre-cooked and dried. In various embodiments, the oatmeal includes a sweetener and/or a another ingredient (such as an ingredient that adds flavor). Non-limiting examples of sweeteners and flavor additives include salt, white sugar, brown sugar, stevia, cinnamon, honey, jam, molasses, maple syrup, butter, chocolate, soy sauce, soy milk, milk, vinegar, condensed or evaporated milk, and cream. In some embodiments, one or more fruits and/or nuts are added, such as strawberries, blueberries, apples, peaches, mangos, bananas, raisins, dried cherries, dried cranberries, pecans, walnuts, and peanut butter. In certain embodiments, oatmeal is used to make porridge, as an ingredient (as in oatmeal cookies and oat cakes), or as an accent as in the topping on an oat bran bread or as the coating on caboc cheese. In various embodiments, oatmeal is used as a thickener in a food, such as chili con carne (e.g., canned chili con carne). In some embodiments, oatmeal is used in an animal feed product.

In certain embodiments, the composition comprises grits and inactivated, non-viable, or dead *Bacillus coagulans* bacteria, or particles comprising such bacteria.

Also provided are soups, such as those that are cold and those that are hot. In various embodiments, soup is a food that is made by combining ingredients such as meat and vegetables in stock or hot/boiling water, until the flavor is extracted, forming a broth. Optionally, soups may be classified into two broad groups: clear soups and thick soups. Thick soups are classified depending upon the type of thickening agent used: purees are vegetable soups thickened with starch; bisques are made from pureed shellfish thickened with cream; cream soups are thickened with bechamel sauce; and veloutes are thickened with eggs, butter and cream. Other ingredients commonly used to thicken soups and broths include rice, flour, and grain. In some embodiments, mixes containing ramen noodles are marketed as an inexpensive instant lunch, requiring only hot water for preparation. Non-limiting types of soups include tomato soup, cream of mushroom soup, chicken noodle soup, vegetable beef soup, minestrone soup, leek and potato soup, lentil soup, fish soup, miso soup, pea soup, fruit soup, clam chowder, gumbo, and bisque. In certain embodiments, a soup, such as vegetable, chicken base, potato, pasta and cheese soups, are available in dry mix form, ready to be served by adding hot water. In various embodiments, a dry mix soup includes dehydrated matter, e.g., dehydrated meat, such as poultry and beef, dehydrated vegetables, dehydrated herbs, dehydrated spices, and/or dehydrated noodles. In some embodiments, a packet of dry soup stock (e.g., ramen) does not contain water. In certain embodiments, an instant soup is preserved into a dry powder which can be stored in, e.g., a packet or a cup. In some embodiments, the inactivated, non-viable, or dead *Bacillus coagulans* bacteria, or particles comprising such bacteria, are in the form of a powder that is added prior to or subsequent to addition of the dry soup mix to hot water. In certain embodiments, inactivated, non-viable, or dead *Bacillus coagulans* bacteria, or particles comprising such bacteria, are within the dry soup mix.

In various embodiments, a composition is a baked composition that comprises inactivated, non-viable, or dead *Bacillus coagulans* bacteria or particles comprising such bacteria. Non-limiting examples of baked compositions include a bread, a cake, a muffin, a pie, a tart, a pastry, a food bar, a granola bar, a quiche, a cookie, a pizza, a baked corn chip, a baked tortilla chip, a baked potato chip, a baked cracker, and baked treats for companion animals. In some embodiments, a baked composition comprises flour. In certain embodiments, a baked composition is a good that is heated, e.g., baked (exposure of dry heat).

In certain embodiments, a baked composition includes a fat. Non-limiting examples of fats include oils, butters, shortenings, artificial lipids, and synthetic fats. Alternatively or in addition a baked composition comprises a fat substitute. In certain embodiments, a baked composition also includes a sugar, or a sugar substitute. In various embodiments, a baked composition comprises an artificial sweetener.

In some embodiments, the composition is a dry mix for a baked composition including a flour and inactivated, non-viable, or dead *Bacillus coagulans* bacteria or particles comprising such bacteria.

In certain embodiments, the composition is bread that contains inactivated, non-viable, or dead *Bacillus coagulans* bacteria or particles comprising such bacteria. Any method of making bread may be used. In various embodiments, bread includes flour and water. In some embodiments, salt is also present. In certain embodiments, a leavening agent such as yeast, egg, baking powder, or baking soda is used. In some embodiments, the bread is quick bread, i.e., bread leavened with a leavening agent other than yeast or eggs (such as baking powder or baking soda). In various embodiments, a baked composition is a yeast-leavened composition within which the inactivated, non-viable, or dead *Bacillus coagulans* bacteria or particles comprising such bacteria are interspersed (e.g., by addition and mixing into dough or batter before leavening and/or cooking). Non-limiting examples of flour include wheat flour, rice flour, corn flour, rye flour, potato flour, millet flour, baking flour, graham flour, and quinoa flour. In various embodiments, the flour is self-rising or comprises self-rising flour. In some embodiments, a baked composition such as bread also contains an amount of sugar, spices, fruit (such as raisins, pumpkins, bananas, strawberries, blueberries, and the like), vegetables (such as onion or zucchini, and the like), nuts, or seeds (such as caraway, sesame or poppy seeds). In some embodiments, an oil (vegetable oil, corn oil, olive oil, grape seed oil, nut oil or fruit oil), butter, shortening, artificial lipid, synthetic fat, or a fat substitute such as olestra is also present. In certain embodiments, a sugar, sugar substitute, or artificial sweetener such as saccharin, sucralose or aspartame is present. Non-limiting examples of baked compositions include, but are not limited to, buns, rolls, bagels, cookies, and pastries.

In various embodiments, the inactivated, non-viable, or dead *Bacillus coagulans* bacteria, or particles comprising such bacteria, are impregnated into the baked composition during the manufacturing process of the baked composition (e.g., added to the batter or dough mix). In some embodiments, the inactivated, non-viable, or dead *Bacillus coagulans* bacteria, or particles comprising such bacteria, are added to the exterior of the baked composition (e.g., as a coating on at least a portion of the exterior surface of the baked composition).

Non-Limiting Examples of Non-Dairy Milk-Like Compositions

In certain embodiments, the composition is a non-dairy milk-like composition containing inactivated, non-viable, or dead *Bacillus coagulans* bacteria or particles comprising such bacteria. Such compositions may provide benefits (e.g., probiotic benefits) to subjects who are vegans, desire a decreased milk cholesterol content, are lactose intolerant, exhibit allergies towards milk proteins, or cannot tolerate or do not wish to consume animal products or by-products.

In various embodiments, a dairy product is a food or drink product made from or containing the milk of a mammal such as a cow, sheep, or goat. A "milk-like composition" does not contain the milk of a mammal. In some embodiments, a milk-like composition has an appearance and/or texture of cow's milk. In certain embodiments, a milk-like composition comprises a liquid from a pressed or pulverized flower, seed, grain, nut, or legume. In various embodiments, a milk-like composition is produced from peas, peanuts, lentils, beans (e.g., soy beans), almonds, cashews, pecans, macadamias, hazelnuts, walnuts, barley, oats, rice, spelt, hemp seeds, pumpkin seeds, quinoa, lupines, sesame seeds, sunflower seeds, and/or coconuts.

In some embodiments, the composition comprises a non-dairy milk-like composition such as milk, cheese, yoghurt, ice cream, pudding, cream cheese, sour cream, coffee creamer, kefir, cottage cheese or mayonnaise. In certain embodiments, a non-dairy milk-like composition includes inactivated, non-viable, or dead *Bacillus coagulans* bacteria, or particles comprising such bacteria, combined with a non-dairy milk-like composition, such as those made from plantmilk, which can be derived from grains (barley, oat, rice, spelt), legumes (peas, peanuts, lentils, beans, soy), nuts (almonds, cashews, pecans, macadamias, hazelnuts, walnuts), and seeds (hemp, pumpkin, quinoa, lupines, sesame, pumpkin, sunflower, coconut).

Non-Limiting Examples of Compositions and Uses for Exercise, Strength, Recovery and Performance Included herein are sports nutrition compositions comprising inactivated, non-viable, or dead *Bacillus coagulans* bacteria or particles comprising such bacteria. In various embodiments, the sports nutrition compositions help increase the benefit of exercise, e.g., by decreasing recovery time, increasing or promoting strength, increasing or promoting endurance, and/or improving (e.g., enhancing or speeding up) the healing of injuries. In some embodiments, sports nutrition compositions comprise a large amount of calories per unit dose to assist a subject in gaining weight, e.g., muscle weight. A unit dose of the compositions described herein is the amount of composition administered to a consumer in a single dose, i.e., one serving. Unit-dose packaging is the packaging of a single dose, e.g., in a non-reusable container. For example, a unit dose refers to a physically discrete unit suitable as unitary doses for an individual, each unit containing a predetermined quantity of active material calculated to produce the desired effect, in association with a suitable carrier, diluent, or excipient. In certain embodiments, packaging may include, e.g., single or multiple unit dosages.

Compositions that provide a large amount of calories to assist a subject in gaining weight are referred to as "weight gainers." In various embodiments, a composition comprises between about 100 and about 10,000 food calories (kcal) per unit dose (i.e., serving), e.g., between 250 and 5,000 kcal, between 500 and 3,000 kcal, between 750 and 2,500 kcal, or between 1,000 and 2,000 kcal, e.g., about 1,000 kcal, about 1,100 kcal, about 1,200 kcal, about 1,300 kcal, about 1,400 kcal, about 1,500 kcal, about 1,600 kcal, about 1,700 kcal, about 1,800 kcal, about 1,900 kcal, or about 2,000 kcal.

In some embodiments, a composition does not comprise a large amount of calories. In certain embodiments, a composition comprises between about 10 and 500 kcal, e.g., between about 20 and 250 kcal, between about 50 and 200 kcal, or between about 100 and 150 kcal, e.g., about 100 kcal, about 110 kcal, about 120 kcal, about 130 kcal, about 140 kcal, or about 150 kcal.

In certain embodiments, a composition comprises protein. For example, the protein comprises about 1% to about 99% by weight of the composition, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% by weight of the composition. For example, the composition comprises between 1 gram and 500 grams of protein, e.g., about 10 grams, about 15 grams, about 20 grams, about 25 grams, about 30 grams, about 35 grams, about 40 grams, about 45 grams, about 50 grams, about 55 grams, about 60 grams, about 65 grams, about 70 grams, about 75 grams, about 80 grams, about 85 grams, about 90 grams, about 95 grams, about 100 grams, about 150 grams, about 200 grams, about 250 grams, about 300 grams, about 350 grams, about 400 grams, about 450 grams, or about 500 grams of protein. In various embodiments, a sports nutrition composition comprises purified or processed protein, such as soy protein, whey protein, rice protein, hemp seed protein, casein protein, or milk protein. In some embodiments, the composition comprises isoleucine, alanine, leucine, arginine, lysine, aspartate, aspartic acid, methionine, cysteine, phenylalanine, threonine, tryptophan, glycine, valine, proline, histidine, serine, tyrosine, asparagine, selenocysteine, pyrrolysine, glutamate, glutamic acid, and/or glutamine.

In certain embodiments, a sports nutrition composition comprises creatine, calcium, sodium caseinate, a whey peptide, or lactoferrin.

In various embodiments, a composition comprises an ingredients such as sodium, potassium, sugar, carbohydrates, dietary fiber, vitamin A, vitamin C, calcium, iron, vitamin D, vitamin E, thiamin, riboflavin, niacin, vitamin B6, folate, vitamin B12, biotin, pantothenic acid, phosphorus, iodine, magnesium, zinc, selenium, copper, manganese, chromium, or molybdenum. In some embodiments, a composition comprises a glucose polymer, a protein blend (e.g., whey protein concentrate, whey protein isolate, egg albumin, milk protein isolate, and partially hydrolyzed whey protein), rice protein concentrate, brown rice concentrate, taurine, L-glutamine, non-dairy creamer (e.g., sunflower oil, a corn syrup solid, sodium caseinate, a monoglyceride, a diglyceride, dipotassium phosphate, tricalcium phosphate, soy lecithin, and/or a tocopherol), a natural and artificial flavor, xantham gum, calcium citrate, potassium citrate, dipotassium phosphate, cellulose gum, tricalcium phosphate, magnesium aspartate, rice starch, carrageenan, a vitamin or mineral (e.g., ascorbic acid, niacinamide, d-alpha tocopheryl succinate, d-calcium pantothonate, zinc citrate, pyridoxine hydrochloride, ferrous fumarate, thiamine mononitrate, riboflavin, manganese amino acid chelate, betacarotene, copper gluconate, folic acid, biotin, potassium iodide, chromium polynicotinate, molybdenum amino acid chelate, selenomethionine, cyanocobalamin, and/or cholecalciferol), sucralose, acesulfame potassium, and/or lactase.

In certain embodiments, a sports nutrition composition comprises an inactive ingredient such as an excipient, binder, or filler. Fillers fill out the size of the compositions, making it practical to produce and convenient for a subject to use. In various embodiments, by increasing the bulk volume, the fillers make it possible for the final product to have the proper volume for handling by an individual. Non-limiting examples of fillers include xantham gum, cellulose gum, lecithin, lactose, sucrose, glucose, mannitol, sorbitol, calcium carbonate, and magnesium stearate.

In some embodiments, a composition does not comprise certain ingredients. In certain embodiments, the composition does not include a sugar (e.g., glucose, fructose, galactose, maltose or lactose), gluten, aspartame, and/or artificial coloring.

In certain embodiments, a composition comprises protein powder, a ready to drink protein shake, a protein bar, a protein bite, or a protein gel.

In various embodiments, included herein is a dry mix sports nutrition composition comprising inactivated, non-viable, or dead *Bacillus coagulans* bacteria or particles comprising such bacteria. In some embodiments, the dry mix includes soy protein, whey protein, rice protein, hemp seed protein, and/or casein protein. In certain embodiments, a sports nutrition composition includes creatine, calcium, sodium caseinate, whey peptides, and/or lactoferrin.

Also provided herein are methods for increasing lean muscle development, exercise recovery, and muscle repair. In various embodiments, a method provided herein comprises the administration of a sports nutrition composition comprising inactivated, non-viable, or dead *Bacillus coagulans* bacteria, or particles comprising such bacteria, prior to, during, and/or after an exercise period. In some embodiments, the composition is administered within 60 minutes of an exercise period (e.g., before or after), e.g., within 15 minutes, within 30 minutes, or within 45 minutes of the exercise period. In certain embodiments, the composition is administered within 2 hours, within 5 hours, or within 8 hours of an exercise period.

In various embodiments, a sports nutrition composition is suitable for animal consumption. In some embodiments, a sports nutrition composition is suitable for human consumption. In certain embodiments, the subject is a human being who desires to increase muscle development, strength, recovery, endurance, or lean body mass, of an animal, e.g., livestock or performance animal such as a work animal (such as a police or military dog) or a race horse, for which an increase in muscle development or strength is desired.

In some embodiments, a sports nutrition composition includes a protein, amino acid such as branched-chain amino acid (BCAA), glutamine, essential fatty acid, meal replacement product, prohormone, creatine, thermogenic product, and/or testosterone booster. BCAAs include leucine, isoleucine, and valine.

Protein products may come in various forms, including protein powder, and ready to drink protein shakes, bars, bites, and gels. In certain embodiments, a protein product may have a flavor such as pineapple, orange, fruit punch, mixed berry, mango, cookies and cream, strawberry, strawberry banana, French vanilla, vanilla, vanilla ice cream, vanilla milkshake, banana, banana cream, Dutch chocolate, mocha cappuccino, double rich chocolate, chocolate caramel, chocolate milkshake, extreme milk chocolate, chocolate mint, chocolate chip, and chocolate. In various embodiments, protein powder is mixed with water, milk or juice (e.g., grapefruit juice, grape juice, and orange juice), resulting in a form known as a "protein shake" (as in milkshake) or "pudding."

In some embodiments, the composition is a meal replacement product (MRP) comprising inactivated, non-viable, or dead *Bacillus coagulans* bacteria or particles comprising such bacteria. In certain embodiments, MPRs are either pre-packaged powdered drink mixes or edible bars designed to replace prepared meals. In various embodiments, a MRP is high in protein, low in fat, has a low to moderate amount of carbohydrates, and contains a wide array of vitamins and minerals. In some embodiments, a MRP uses whey protein, casein (e.g., calcium caseinate or micellar casein), soy protein, and/or egg albumin as a protein source. In certain embodiments, a carbohydrate is derived from maltodextrin, oat fiber, brown rice, and/or wheat flour. In various embodiments, a compositions such as MRPs comprise flax seed oil.

In various embodiments, a sports nutrition composition provided herein comprises a bodybuilding ingredient such as calcium, sodium caseinate, whey peptide, a glutamine peptide, L-glutamine, calcium alpha-ketoglutarate, isolated/free amino acids, lactoferrin, conjugated linoleic acid, medium chain triglycerides, or creatine (e.g., creatine monohydrate).

In some embodiments, sports nutrition composition ingredients are blended together as dry ingredients.

In certain embodiments, a sports nutrition composition is ready for immediate use or for storage in a sterile package, e.g., a 3-ounce package (e.g., a bag or a bottle), a 6-ounce package, a 9-ounce package, a 12-ounce package, a 15-ounce package, an 18-ounce package, a 24-ounce package, a 48-ounce package, 80-ounce package, or 100-ounce package. In various embodiments, a dried powder is packaged in unit dose quantities, e.g., 5 grams, 10 grams, 20 grams, 30 grams, 40 grams, 50 grams, 60 grams, 70 grams, 80 grams, 90 grams, or 100 gram packets. In some embodiments, a dried powder is packaged in bulk, e.g., about 500 grams, about 600 grams, about 700 grams, about 800 grams, about 900 grams, about 1,000 grams, about 1,250 grams, about 1,500 grams, about 1,750 grams, about 2,000 grams, about 2,250 grams, about 2,500 gram, or about 3,000 gram containers. In certain embodiments, the sports nutrition composition is stored in a sterile package at room temperature prior to consumption.

Non-Limiting Examples of Oil and Fatty Acid Compositions

Also included herein are compositions comprising an omega-3 fatty acid and inactivated, non-viable, or dead *Bacillus coagulans* bacteria, or particles comprising such bacteria. In various embodiments, the omega-3 fatty acid comprises eicosapentaenoic acid or docosahexaenoic acid. In some embodiments, the omega-3 fatty acid has been produced by microalgae. In certain embodiments, the omega-3 fatty acid is in oil. In various embodiments, the oil comprises seafood oil. In some embodiments, the oil comprises shellfish oil or fish oil. In certain embodiments, the oil comprises krill oil. In various embodiments, the oil comprises salmon oil, cod oil, herring oil, anchovy oil, sardine oil, or pollock oil, tuna oil, catfish oil, flounder oil, lake trout oil, grouper oil, halibut oil, mahi mahi oil, orange roughy oil, red snapper oil, shark oil, swordfish oil, tilefish oil, or mackerel oil. In some embodiments, the oil comprises cod oil, such as cod liver oil.

In certain embodiments, the composition is encapsulated in a soft-shelled capsule or a soft gelatin capsule. In various embodiments, the oil has been processed to remove an impurity (such as a toxin, polychlorinated biphenyl, or mercury). In some embodiments, the inactivated, non-viable, or dead *Bacillus coagulans* bacteria, or particles comprising such bacteria, and an oil are encapsulated together.

In certain embodiments, the composition comprises a preservative.

In various embodiments, the omega-3 fatty acid comprises eicosapentaenoic acid and/or docosahexaenoic acid.

In some embodiments, the oil is converted to ethyl esters. In certain embodiments, the oil is subjected to trans-esterification. In various embodiments, the oil is subjected to molecular or vacuum distillation to remove other fats and undesirable elements and to concentrate the oil. In some embodiments, an ingredient such as acid clay is added to remove a pungent smell from fish oil.

EMBODIMENTS

Embodiments include P1 to P72 following:
Embodiment P1. A composition comprising particles that comprise inactivated, non-viable, or dead *Bacillus coagulans* bacteria in an amount that is effective to increase the level of at least one growth factor in a subject.
Embodiment P2. The composition of Embodiment P1, wherein at least 95% of the particles comprise at least one dimension of less than 420 μm and at least 75% of the particles comprise at least one dimension of less than 180 μm.
Embodiment P3. The composition of Embodiment P1 or P2, wherein at least one dimension of each of the particles is between about 5 μm and 750 μm.
Embodiment P4. The composition of any one of Embodiments P1-P3, wherein the at least one growth factor comprises an immune-activating or anti-inflammatory growth factor.
Embodiment P5. The composition of any one of Embodiments P1-P4, wherein the composition is less than about 0.001% water by weight.
Embodiment P6. The composition of any one of Embodiments P1-P5, wherein the at least one growth factor is granulocyte colony-stimulating factor (G-CSF) or granulocyte macrophage colony-stimulating factor (GM-CSF).
Embodiment P7. The composition of any one of Embodiments P1-P6, wherein the effective amount is also effective to increase the level of interleukin-1 receptor antagonist (IL1RA), interleukin-6 (IL-6), or interleukin-10 (IL-10) in the subject.
Embodiment P8. The composition of any one of Embodiments P1-P8, wherein the level is the level of the at least one growth factor in a bodily fluid of the subject.
Embodiment P9. The composition of Embodiment P8, wherein the bodily fluid is blood, plasma, or serum.
Embodiment P10. The composition of any one of Embodiments P1-P9, wherein the inactivated, non-viable, or dead *Bacillus coagulans* bacteria comprise inactivated, non-viable, or dead *Bacillus coagulans* vegetative bacteria.
Embodiment P11. The composition of Embodiment P10, wherein the inactivated, non-viable, or dead *Bacillus coagulans* bacteria comprise inactivated, non-viable, or dead *Bacillus coagulans* vegetative bacteria and spores.
Embodiment P12. The composition of Embodiment P10 and P11, wherein the cell wall surface areas of the inactivated, non-viable, or dead *Bacillus coagulans* vegetative bacteria are at least about 75% intact compared to the cell wall surface areas of corresponding viable *Bacillus coagulans* vegetative bacteria.
Embodiment P13. The composition of any one of Embodiments P10-P12, wherein the inactivated, non-viable, or dead *Bacillus coagulans* vegetative bacteria have at least about 90% of the mass of corresponding viable *Bacillus coagulans* bacteria.
Embodiment P14. The composition of any one of Embodiments P1-P13, wherein the inactivated, non-viable, or dead *Bacillus coagulans* bacteria can be identified as containing *Bacillus coagulans* genomic DNA by sequencing.
Embodiment P15. The composition of any one of Embodiments P1-P14, wherein the inactivated, non-viable, or dead *Bacillus coagulans* bacteria comprise at least one 500 kilobase portion of the *Bacillus coagulans* genome.
Embodiment P16. The composition of any one of Embodiments P1-P15, wherein the inactivated, non-viable, or dead *Bacillus coagulans* bacteria comprise at least one 1000 kilobase portion of the *Bacillus coagulans* genome.
Embodiment P17. The composition of any one of Embodiments P1-16, further comprising an excipient.
Embodiment P18. The composition of any one of Embodiments P1-P17, further comprising a β-glucan, maltodextrin, inulin, initosol, trehalose, micro-crystalline cellulose (MCC), calcium lactate, magnesium stearate, fructo-oligosaccharide (FOS), or gluco-oligosaccharide (GOS).

Embodiment P19. The composition of any one of Embodiments P1-P18, wherein the inactivated, non-viable, or dead *Bacillus coagulans* bacteria are lyophilized.

Embodiment P20. The composition of Embodiment 19, wherein the inactivated, non-viable, or dead *Bacillus coagulans* bacteria have been lyophilized and then combined with an aqueous solution.

Embodiment P21. The composition of any one of Embodiments P1-P20, further comprising a surfactant or an emulsifier.

Embodiment P22. The composition of Embodiment 21, wherein the surfactant comprises polysorbate 20 or polysorbate 80.

Embodiment P23. The composition of any one of Embodiments P1-P22, which is a food or beverage composition.

Embodiment P24. The composition of Embodiment P23, comprising tea, coffee, or an alcoholic beverage.

Embodiment P25. The composition of Embodiment P23, comprising a fermented food or beverage.

Embodiment P26. The composition of Embodiment P23, comprising a grain-based composition.

Embodiment P27. The composition of Embodiment P23, comprising a baked composition.

Embodiment P28. The composition of Embodiment P23, comprising a confection.

Embodiment P29. The composition of Embodiment P23, comprising an omega-3 fatty acid.

Embodiment P30. The composition of Embodiment P23, comprising a dairy composition.

Embodiment P31. The composition of Embodiment P23, comprising a non-dairy milk-like composition.

Embodiment P32. The composition of Embodiment P23, comprising a sports nutrition composition.

Embodiment P33. The composition of Embodiment P23, which is animal feed.

Embodiment P34. The composition of Embodiment P23, wherein the animal feed comprises feed for a work animal, a companion animal, livestock, or aquaculture.

Embodiment P35. The composition of any one of Embodiments P1-P34, wherein the effective amount is also effective to increase the level of at least one immune activating cytokine in the subject.

Embodiment P36. The composition of Embodiment 35, wherein the at least one immune activating cytokine comprises interleukin-1 beta (IL-1β), interleukin-6 (IL-6), interleukin-17A (IL-17A), Tumor Necrosis Factor-α (TNF-α), or interferon gamma (IFNγ).

Embodiment P37. The composition of any one of Embodiments P1-P36, wherein the effective amount is also effective to increase the level of at least one immune activating chemokine in the subject.

Embodiment P38. The composition of Embodiment P37, wherein the at least one immune activating chemokine comprises monocyte chemoattractant protein-1 (MCP-1), macrophage inflammatory protein 1-alpha (MIP-1α), or macrophage inflammatory protein-1β (MIP1β).

Embodiment P39. The composition of any one of Embodiments P1-P38, wherein the effective amount is also effective to increase the level of at least one anti-inflammatory cytokine in the subject.

Embodiment P40. The composition of Embodiment P39, wherein the at least one anti-inflammatory cytokine comprises IL-1RA or IL-10.

Embodiment P41. The composition of any one of Embodiments P1-P40, wherein the growth factor increases tissue repair, stem cell differentiation, or stem cell proliferation.

Embodiment P42. A method of increasing tissue repair in a subject, comprising administering an effective amount of the composition of any one of Embodiments P1-P41 to the subject.

Embodiment P43. The method of Embodiment P42, wherein the subject has an injury.

Embodiment P44. The method of Embodiment P42 or P43, wherein the subject has traumatic brain injury.

Embodiment P45. The method of any one of Embodiments P42-P44, wherein the subject has had a stroke.

Embodiment P46. The method of any one of Embodiments P42-P45, wherein the subject has arthritis.

Embodiment P47. The method of Embodiment P46, wherein the arthritis is osteoarthritis.

Embodiment P48. The method of Embodiment P46, wherein the arthritis is rheumatoid arthritis.

Embodiment P49. The method of any one of Embodiments P42-P48, wherein the subject does not have a respiratory, mucous membrane, skin, or gastrointestinal infection.

Embodiment P50. The method of any one of Embodiments P42-P49, wherein the effective amount reduces inflammation in the subject.

Embodiment P51. The method of any one of Embodiments P42-P50, wherein the effective amount increases the level of G-CSF or GM-CSF in the subject.

Embodiment P52. The method of any one of Embodiments P42-P51, wherein the effective amount increases the level of IL1RA, IL-6, or IL-10 in the subject.

Embodiment P53. The method of any one of Embodiments P42-P52, wherein the tissue is muscle tissue.

Embodiment P54. A method of increasing physical performance in a subject, comprising administering an effective amount of the composition of any one of Embodiments P1-P41 to the subject.

Embodiment P55. The method of Embodiment P54, wherein increasing physical performance comprises reducing muscle soreness.

Embodiment P56. The method of Embodiment P55, wherein the muscle soreness is post-exercise muscle soreness.

Embodiment P57. The method of any one of Embodiments P54-P56, wherein increasing physical performance comprises increasing physical strength or endurance.

Embodiment P58. The method of any one of Embodiments P54-P57, wherein increasing physical performance comprises decreasing post-exercise recovery time.

Embodiment P59. The method of any one of Embodiments P54-P58, wherein increasing physical performance comprises increasing muscle mass.

Embodiment P60. The method of any one of Embodiments P54-P59, wherein the subject desires increased physical performance.

Embodiment P61. The method of any one of Embodiments P54-P60, wherein the subject is an athlete.

Embodiment P62. The method of any one of Embodiments P54-P61, wherein the subject is a police officer or a member of an armed force.

Embodiment P63. The method of any one of Embodiments P54-P60, wherein the animal is a performance animal, a companion animal, or a work animal.

Embodiment P64. A method of increasing lean muscle development, recovery, strength, or repair in a subject, comprising administering an effective amount of the composition of any one of Embodiments P1-P41 to the subject.

Embodiment P65. A composition comprising *Bacillus coagulans* peptidoglycan or lipoteichoic acid in an amount that is effective to increase the level of at least one growth factor in a subject.

Embodiment P66. The composition of Embodiment P65, comprising both peptidoglycan and lipoteichoic acid.

Embodiment P67. The composition of Embodiment P65 or P66, wherein the peptidoglycan or lipoteichoic acid is purified peptidoglycan or lipoteichoic acid.

Embodiment P68. The composition of any one of Embodiments P65-P67, which does not comprise a viable *Bacillus coagulans* bacterium.

Embodiment P69. The composition of any one of Embodiments P65-P68, further comprising a β-glucan.

Embodiment P70. The composition of any one of Embodiments P65-P69, which is a food or beverage composition.

Embodiment P71. The composition of Embodiment P70, comprising
 (a) tea, coffee, or an alcoholic beverage;
 (b) a fermented food or beverage;
 (c) a grain-based composition;
 (d) a baked composition;
 (e) a confection;
 (f) an omega-3 fatty acid;
 (g) a dairy composition;
 (h) a non-dairy milk-like composition;
 (i) a sports nutrition composition; or
 (j) animal feed.

Embodiment P72. A composition comprising whole dead *Bacillus coagulans* bacteria in an amount that is effective to increase the level of at least one growth factor in a subject following ingestion, wherein said growth factor comprises granulocyte colony-stimulating factor (G-CSF), granulocyte macrophage colony-stimulating factor (GM-CSF). interleukin-1 receptor antagonist (IL1RA), interleukin-6 (IL-6), or interleukin-10 (IL-10).

Additional embodiments include Embodiments 1 to 35 following:

Embodiment 1. A method of increasing physical performance in a subject, comprising administering an effective amount of composition comprising inactivated, non-viable, or dead *Bacillus coagulans* bacteria to the subject.

Embodiment 2. The method of Embodiment 1, wherein the inactivated, non-viable, or dead *Bacillus coagulans* bacteria comprise inactivated, non-viable, or dead *Bacillus coagulans* spores.

Embodiment 3. The method of Embodiment 1 or 2, wherein bacteria comprises at least 85% *Bacillus coagulans* spores.

Embodiment 4. The method of any one of Embodiments 1-3, wherein the inactivated, non-viable, or dead *Bacillus coagulans* bacteria comprise inactivated, non-viable, or dead *Bacillus coagulans* vegetative bacteria.

Embodiment 5. The method of any one of Embodiments 1-4, wherein the bacteria are *Bacillus coagulans* GBI-30 (ATCC Designation No. PTA-6086), bacteria.

Embodiment 6. The method of any one of Embodiments 1-5, wherein increasing physical performance comprises reducing muscle soreness.

Embodiment 7. The method of Embodiment 6, wherein the muscle soreness is post-exercise muscle soreness.

Embodiment 8. The method of any one of Embodiments 1-7, wherein increasing physical performance comprises increasing physical strength or endurance.

Embodiment 9. The method of any one of Embodiments 1-8, wherein increasing physical performance comprises decreasing post-exercise recovery time.

Embodiment 10. The method of any one of Embodiments 1-9, wherein increasing physical performance comprises increasing muscle mass.

Embodiment 11. The method of any one of Embodiments 1-10, wherein increasing physical performance comprises increasing lean muscle development, recovery, strength, or repair in the subject.

Embodiment 12. The method of any one of Embodiments 1-11, wherein the subject desires increased physical performance.

Embodiment 13. The method of any one of Embodiments 1-12, wherein the subject is an athlete, a police officer, or a member of an armed force.

Embodiment 14. The method of any one of Embodiments 1-12, wherein the subject is a performance animal, a companion animal, or a work animal.

Embodiment 15. The method of any one of Embodiments 1-14, wherein the subject has an injury or arthritis, or has had a stroke.

Embodiment 16. The method of any one of Embodiments 1-15, wherein the subject does not have a respiratory, mucous membrane, skin, or gastrointestinal infection.

Embodiment 17. The method of any one of Embodiments 1-16, wherein the effective amount is effective to reduce inflammation in the subject.

Embodiment 18. The method of any one of Embodiments 1-17, wherein the effective amount is effective to increase the level of at least one growth factor in a subject.

Embodiment 19. The method of Embodiment 18, wherein the level is the level of the at least one growth factor in a bodily fluid of the subject.

Embodiment 20. The method of Embodiment 19, wherein the bodily fluid is blood, plasma, or serum. Embodiment 21. The method of Embodiment 18, wherein the growth factor increases tissue repair, stem cell differentiation, or stem cell proliferation.

Embodiment 22. The method of Embodiment 18, wherein the effective amount is effective to increase the level of granulocyte colony-stimulating factor (G-CSF) or granulocyte macrophage colony-stimulating factor (GM-CSF) in the subject.

Embodiment 23. The method of any one of Embodiments 1-22, wherein the effective amount is effective to increase the level of interleukin-1 receptor antagonist (IL1RA), interleukin-6 (IL-6), or interleukin-10 (IL-10) in the subject.

Embodiment 24. The method of any one of Embodiments 1-23, wherein the effective amount is effective to increase the level of at least one immune activating cytokine in the subject.

Embodiment 25. The method of Embodiment 24, wherein the at least one immune activating cytokine comprises interleukin-1 beta (IL-1β), interleukin-6 (IL-6), interleukin-17A (IL-17A), Tumor Necrosis Factor-α (TNF-α), or interferon gamma (IFNγ).

Embodiment 26. The method of any one of Embodiments 1-25, wherein the effective amount is effective to increase the level of at least one immune activating chemokine in the subject.

Embodiment 27. The method of Embodiment 26, wherein the at least one immune activating chemokine comprises monocyte chemoattractant protein-1 (MCP-1), macrophage inflammatory protein 1-alpha (MIP-1α), or macrophage inflammatory protein-1β (MIPIβ).

Embodiment 28. The method of any one of Embodiments 1-27, wherein the composition is less than about 0.001% water by weight.

Embodiment 29. The method of any one of Embodiments 1-28, wherein the composition further comprises an excipient.

Embodiment 30. The method of any one of Embodiments 1-29, wherein the composition further comprises a β-glucan, maltodextrin, inulin, initosol, trehalose, micro-crystalline cellulose (MCC), calcium lactate, magnesium stearate, fructo-oligosaccharide (FOS), or gluco-oligosaccharide (GOS).

Embodiment 31. The method of any one of Embodiments 1-30, wherein the inactivated, non-viable, or dead *Bacillus coagulans* bacteria are lyophilized.

Embodiment 32. The method of any one of Embodiments 1-30, wherein the inactivated, non-viable, or dead *Bacillus coagulans* bacteria have been lyophilized and then combined with an aqueous solution.

Embodiment 33. The method of any one of Embodiments 1-32, wherein the composition further comprises a surfactant or an emulsifier.

Embodiment 34. The method of any one of Embodiments 1-33, wherein the composition is a food or beverage composition.

Embodiment 35. The method of Embodiment 34, wherein the food or beverage composition comprises:
 (a) tea, coffee, or an alcoholic beverage;
 (b) a fermented food or beverage;
 (c) a grain-based composition;
 (d) a baked composition;
 (e) a confection;
 (f) an omega-3 fatty acid;
 (g) a dairy composition;
 (h) a non-dairy milk-like composition;
 (i) a sports nutrition composition; or
 (j) feed for a work animal, a companion animal, livestock, or aquaculture.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 45° C. After fermentation, the *B. coagulans* bacterial cells or spores are collected using standard methods (e.g., filtration, centrifugation) and the collected cells and spores can be lyophilized, spray-dried, air-dried, or frozen. The supernatant from the cell culture is collected and used as an extracellular agent secreted by *B. coagulans*.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

Example 2: Preparation of *Bacillus coagulans* Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g $MnSO_4$. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3: Inactivated Probiotic *Bacillus coagulans* GBI-30 Induces Complex Immune Activating, Anti-Inflammatory, and Regenerative Markers In Vitro This study was done to test a new consumable health product, made by heat-killing a probiotic gut bacteria. It was previously shown that this strain of gut bacteria activates human immune cells and helps mature certain immune cells that are of importance for detecting foreign antigens. The inactivation (e.g., heat-killing) process allows the bacterium to be used in broader applications, such as foods where a living bacterium could spoil the food, or give it a very limited shelf life. It was important to show that the heat-killed bacteria had similar properties to the live bacteria.

In order to test this, blood samples from healthy humans were used, and a part of the white blood cells that include immune cells and stem cells was isolated. The blood samples contained the same types of cells as in the blood circulation in the intestinal walls, where antigens from the gut are presented to immune cells. The cells were cultured with the inactivated bacteria for 24 hours. The immune cells were examined for their activation status. The liquid culture medium was tested for secreted biomarkers.

It was found that the heat-killed bacteria had similar effects as the live ones with respect to immune activation and anti-inflammatory effects. Surprisingly, effects that showed that the human cells secreted growth factors important for tissue repair after trauma and injury were also found.

The gut microbial community, "gut microbiome", has a vast impact on the health of the human host (The Human Microbiome Project Consortium. Nature 2012; 486(7402): 207-214; Shreiner et al. Curr Opin Gastroenterol. 2015; 31(1):69-75). An integral collaboration exists between microbial forms colonizing the gut, and our immune function, metabolism, and brain function (Galland J Med Food 2014; 17(12):1261-72). The interaction between gut microbes and host cells and tissue takes place in several ways, including via bacterial cell wall components and secreted metabolites. The most immediate and direct interaction between microbes and host cells involves the outer layers of bacterial cell wall components engaging with receptors on immune cells such as dendritic cells directly sampling antigens in the gut lumen. This interaction presents different types of bacterial cell wall components of Gram-positive versus Gram-negative bacteria. Gram-negative bacteria present lipopolysaccharides which are recognized by Toll-Like Receptor-4 (TLR-4) (Gioannini and Weiss Immunol Res. 2007; 39(1-3):249-60), whereas the outer cell walls of Gram-positive bacteria present teichoic acid and lipoteichoic acid to immune cells, recognized by TLR-2 (Schwandner et al. J Biol Chem 1999; 274:17406-17409). For many pathogenic bacteria, lipoteichoic acid is associated with virulence (Kang et al. Arch Pharm Res. 2016; 39(11): 1519-1529), whereas lipoteichoic acid from beneficial probiotic bacteria trigger complex beneficial immune modulation. Lipoteichoic acid has been widely used as a model TLR-2 ligand to explore a wide variety of immune activating mechanisms at the cellular and molecular level, and interestingly has proven to exert both pro-inflammatory (Paustian et al. PLoS One. 2013; 8(1):e54804; Cheng et al. Cytokine. 2013; 61(2):499-505) and anti-inflammatory (Kim et al. Mol Cells. 2012; 33(5):479-86; Kim et al. Mol Immunol. 2011; 48(4):382-91) activities in vitro. The structural complexity of lipoteichoic acid is suggested to impact the host immune response. The chemical composition of lipoteichoic acid differs between microbes, and between strains of similar microbes. This is of high importance in triggering diverse effects on host cells, and likely one of the key factors in the highly selective immune-modulating effects induced by different microbial strains.

The consumption of beneficial probiotic bacteria is associated with a range of health benefits tied to inflammation regulation, including gastrointestinal disease (Korpela et al. PLoS One 2016; 11(4):e0154012), respiratory tract infections (Lenoir-Wijnkoop et al. PLoS One. 2016; 11(11): e0166232), neuro-immune and neuropsychiatric disorders (Wang et al. Brain Behav Immun. 2014; 38:1-12), satiety and psychosocial behavior in obese individuals (Sanchez et al. Nutrients. 2017; 9(3)), and alleviation of symptoms of anxiety and depression (Wallace et al. Ann Gen Psychiatry. 2017; 16:14), as a result of the extensive communication between the gastrointestinal and central nervous systems, also referred to as the "gut-brain axis (Dinan et al. Gastroenterol Clin North Am. 2017; 46(1):77-89). While the consumption of probiotic bacteria is considered highly safe, there are many useful applications for inactivated probiotic strains, such as increased shelf life, as well as usefulness in many types of food products where metabolically active, living bacteria may spoil the appearance of the food. Inactivated probiotic bacteria also have a use in specific clinical situations involving immune-compromised individuals where there could potentially be a risk of translocation of gut bacteria into the blood stream. Inactivated probiotic bacteria can be produced by heating, leaving the outer bacterial cell wall as the main mechanism of interaction with host immune cells. Heat-killed *Lactobacillus plantarum* L-137 (HK L-137) has been widely studied over the past decades for its effects in rodents and humans. Animal studies have shown that consumption of HK L-137 offers protection against influenza virus infection, associated with increased production of interferons, suggesting a general support of anti-viral immune defense activity (Maeda et al. Int Immunopharmacol. 2009 August; 9(9):1122-5). Clinical trials have shown that the daily intake of HK L-137 supports a healthy immune function, including enhanced acquired immune responses and TH1 related immune function (Hirose et al. J Nutr. 2006 December; 136(12):3069-73), and reduced incidence of upper respiratory tract infections (Hirose et al. J Nutr Sci. 2013 Dec. 6; 2:e39). Consumption was also associated with improved oral health (Iwasaki et al. Oral Health Prev Dent. 2016; 14(3):207-14). The heat-killed bacteria are also known to exert anti-allergic (Murosaki et al. J Allergy Clin Immunol. 1998 July; 102(1):57-64) and anti-tumor (Guo et al. Bull Cancer. 2015 March; 102(3):204-12) effects, in part due to potent induction of IL-12 and interferons (Arimori et al. Immunopharmacol Immunotoxicol. 2012 December; 34(6):937-43) by lipoteichoic acids on the bacterial surfaces. Furthermore, the L-137 strain has higher levels of lipoteichoic acids exposed on the surface, with higher amounts of alanine, than the closely related *Lactobacillus plantarum* JCM1149 strain (Hatano et al. Int Immunopharmacol. 2015 April; 25(2):321-31); this correlates with the higher induction of IL-12 by the L-137 strain than by the JCM1149 strain (Hirose et al. Microbiol Immunol. 2010 March; 54(3):143-51).

Another group of lactic acid-producing probiotic bacteria includes several unique strains of the spore-forming *Bacillus coagulans* (previously classified as *Lactobacillus sporogenes*). The teichoic acid from *Bacillus coagulans* walls has a higher lipid content than most Gram-positive bacteria, and is a glycerophosphate polymer substituted with two neutral sugars, glucose and galactose. It is unique in lacking amino acid substituents otherwise considered a characteristic of teichoic acids (Forrester and Wicken Microbiology, 1 Jan. 1966, 42: 147-154).

Cell walls from the live GBI-30 strain has demonstrated immune modulating and anti-inflammatory effects in vitro (Jensen et al. BMC Immunol. 2010; 24:11-15). It was previously shown that immune modulating effects of the *Bacillus coagulans* GBI-30 strain were associated both with the cell wall fraction and with the metabolites produced by the live bacterial in vitro (Benson et al. World J Gastroenterol. 2012 Apr. 28; 18(16):1875-83). The probiotic strain was further shown to prolong the survival and reduce symptoms in mice infected with *Clostridium difficile* (Fitzpatrick et al. Gut Pathog. 2011 Oct. 20; 3(1):16; Fitzpatrick et al. Gut Pathog. 2012 Oct. 22; 4(1):13). Clinical studies showed that consuming GBI-30 helped alter the gut microbiome by increasing the numbers of beneficial bacteria (Nyangale et al. Anaerobe. 2014 December; 30:75-81), and ex vivo testing of blood from elderly humans who had consumed GBI-30 for 28 days showed increased anti-inflammatory cytokine responses (Nyangale et al. J Nutr. 2015 July; 145(7):1446-52). Results from a recent clinical trial suggest that consumption of GBI-30 supports exercise performance and helps reduce exercise-induced muscle damage (Jager et al. Peer J. 2016 Jul. 21; 4:e2276).

Recently, heat-inactivated *Bacillus coagulans* GBI-30 bacteria have been produced for oral consumption. The work presented here was undertaken to document whether the immune activating and anti-inflammatory properties associated with the cell walls of the live GBI-30 strain were protected in the inactivated product. An important focus for this work was to document the biological activities of the inactivated bacteria when presented to human immune cells in a cell culture system that allows cross-talk between antigen-presenting monocytes and dendritic cells with lymphocytes and natural killer cells, and thus mimics events in the gut mucosal immune tissue.

Materials and Methods

Reagents

Phosphate-buffered saline, Roswell Park Memorial Institute 1640 (RPMI-1640) medium, penicillin-streptomycin 100×, interleukin-2 (IL-2), and lipopolysaccharide (LPS) were purchased from Sigma-Aldrich Co. (St Louis, Mo., USA). CD69 fluorescein isothiocyanate, CD56 phycoerythrin, CD3 peridinin chlorophyll protein, CD25 brilliant violet 421 and heparin Vacutainer tubes were purchased from BD Biosciences (Franklin Lakes, N.J., USA). The Bio-Plex Pro™ human cytokine 27-Plex was purchased from Bio-Rad Laboratories Inc. (Hercules, Calif., USA).

Inactivated *Bacillus coagulans* GBI-30 (Staimune™)

Inactivated *Bacillus coagulans* GBI-30 (ATCC Designation Number PTA-6086) bacteria were provided by Ganeden Biotech. Bacterial numbers were 15 billion ($1.5 \times 10^{10}$) (CFU) per gram. Inactivated bacteria were diluted in physiological saline and added to cell cultures at doses from $0.78 \times 10^6$-$100 \times 10^6$ inactivated bacteria/mL cell culture.

Peripheral Blood Mononuclear Cell Cultures

Healthy human volunteers between the age of 50 and 60 years served as blood donors upon informed consent, as approved by the Sky Lakes Medical Center Institutional Review Board (FWA 2603). Freshly drawn peripheral venous blood samples in sodium heparin were layered onto Lympholyte-Poly, and centrifuged for 35 minutes at 1800 rpm (450 g). The upper PBMC-rich interface was harvested using sterile transfer pipettes into new vials, and washed twice with 10 mL PBS, without calcium or magnesium, by centrifugation at 2400 rpm for 10 minutes. The cells were resuspended into RPMI 1640 with 10% fetal bovine serum, L-glutamine, and antibiotics (penicillin and streptomycin) to a cell density of $10^6$/mL. Triplicate cultures were established for each of the eight doses of inactivated GBI-30 tested. Untreated cell cultures (negative controls were established in hexaplicate. Two sets of positive control cultures were established in triplicates: One set using LPS (10 ng/mL), and another set using IL-2 (100 IU/mL) to activate the immune cells by two different pathways.

Cytokine Testing

Supernatants were harvested from the human immune cell 24-hour cultures, and the levels of 27 cytokines, chemokines, and growth factors were analyzed. Testing was performed on culture supernatants from cell cultures treated with the six higher doses of inactivated GBI-30. The following markers: Interleukin (IL)-1beta, IL-1ra, IL-2, IL-4, IL-5, IL-6, IL-7, IL-8, IL-9, IL-10, IL-12 (p70), IL-13, IL-15, IL-17, eotaxin, basic fibroblast growth factor (FGF), granulocyte-colony stimulating factor (G-CSF), granulocyte-macrophage colony-stimulating factor (GM-CSF), interferon (IFN)-gamma, interferon gamma-induced protein 10 (IP-10), monocyte chemoattractant protein-1 (MCP-1; MCAF), macrophage inflammatory protein (MIP)-1alpha, MIP-1beta, platelet-derived growth factor (PDGF)-BB, regulated on activation, normal T cell expressed and secreted (RANTES), tumor necrosis factor (TNF)-alpha, and vascular endothelial growth factor (VEGF) were quantified using Bio-Plex protein arrays (Bio-Rad Laboratories Inc.) and utilizing xMAP technology (Luminex, Austin, Tex., USA).

Statistical Analysis

Averages and standard deviations for each data set were calculated using Microsoft Excel. Statistical analysis was performed using the 2-tailed, independent t-test. Statistical significance was indicated when $p<0.05$, and a high level of significance when $p<0.01$.

Results

Immune Cell Activation

Figure 1B:
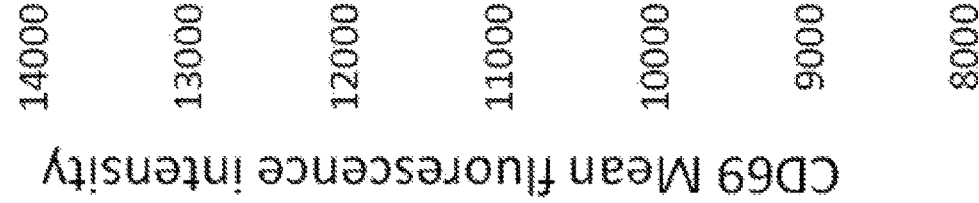

Immune cell activation by inactivated *Bacillus coagulans* GBI-30 was determined by measuring cell-surface expression of the activation marker CD69. The gating on cells with different forward and side scatter properties allowed analysis of CD69 expression on lymphocytes versus monocytes/macrophages (FIG. 1). Treatment of both cell types with inactivated GBI-30 for 24 hours resulted in activation across a broad dose range. The results for CD69 expression on lymphocytes showed that even at the lowest dose the CD69 expression was not returning to baseline, and suggests that much lower doses would still have been able to activate lymphocytes (FIG. 1A). In contrast, the most robust and statistically significant activation of monocytes was in a narrower dose range, returning towards baseline at the lowest dose shown (FIG. 1B).

Figure 2A:
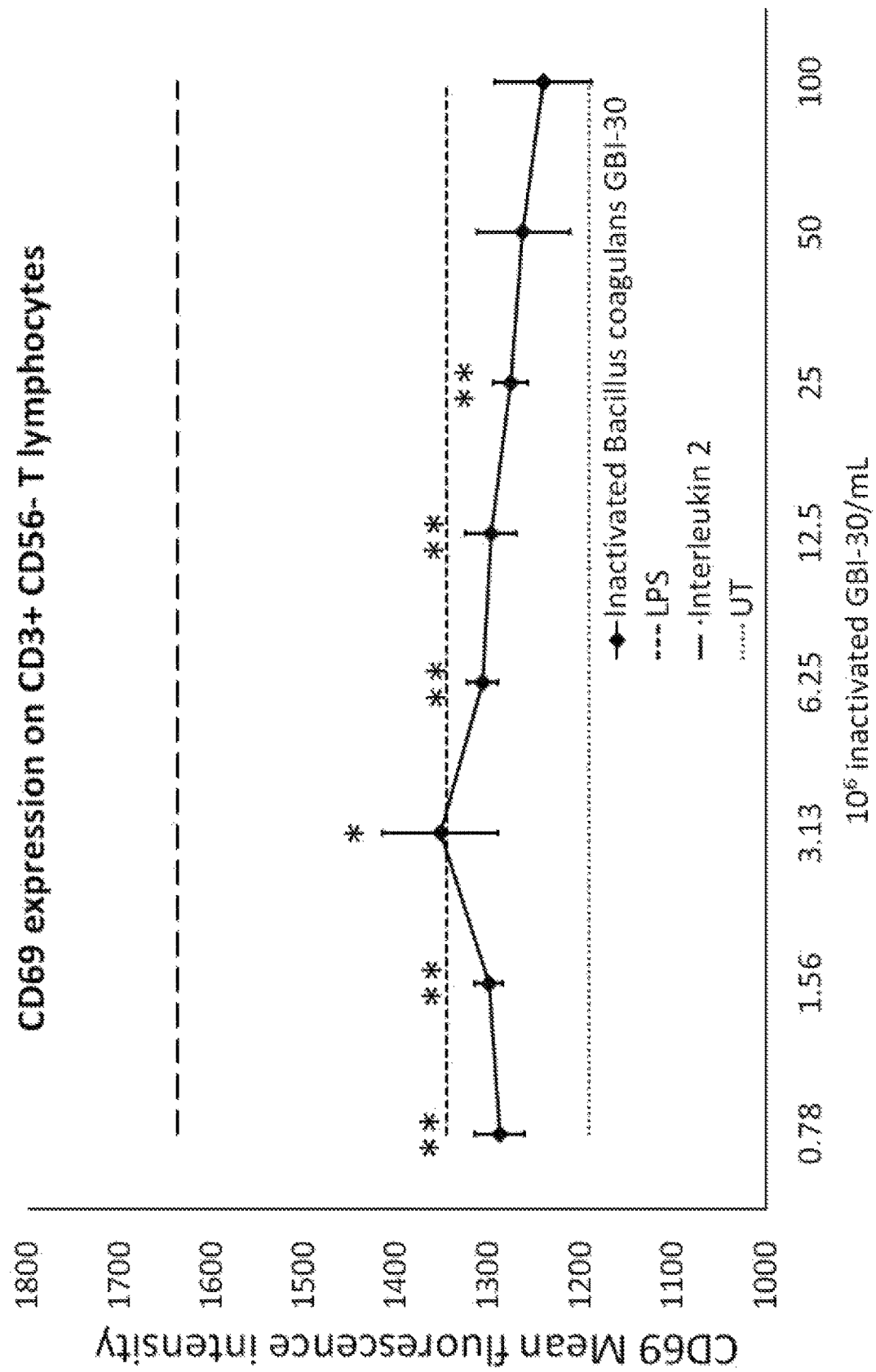
FIGS. 2A-D are graphs showing the expression of the CD69 cellular activation marker on immune cell subsets. CD69 expression on T lymphocytes (FIG. 2A), NKT cells (FIG. 2B), NK cells (FIG. 2C), and non-T non-NK cells (FIG. 2D) in human PBMC cultures treated for 24 hours with serial dilutions of inactivated *Bacillus coagulans* GBI-30. Mean fluorescence intensity for CD69 expression is shown. Data presented as mean±standard deviation from triplicate cultures and represents one of three separate experiments using PBMC cells from three different healthy human donors. Abbreviations: LPS, Lipopolysaccharide; UT, untreated. Notes: *P<0.05; **P<0.01.
Figure 2B:
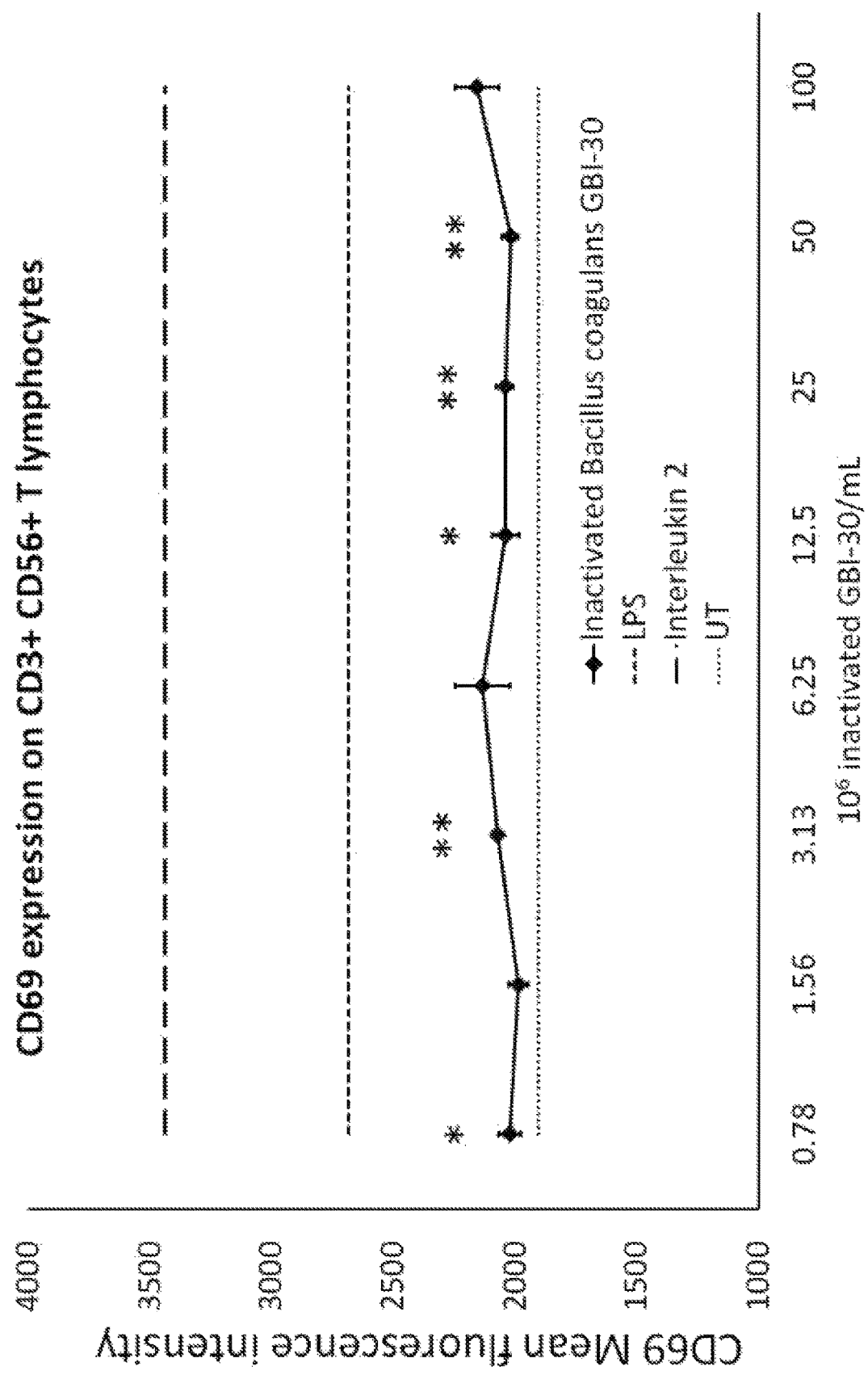
Figure 2C:
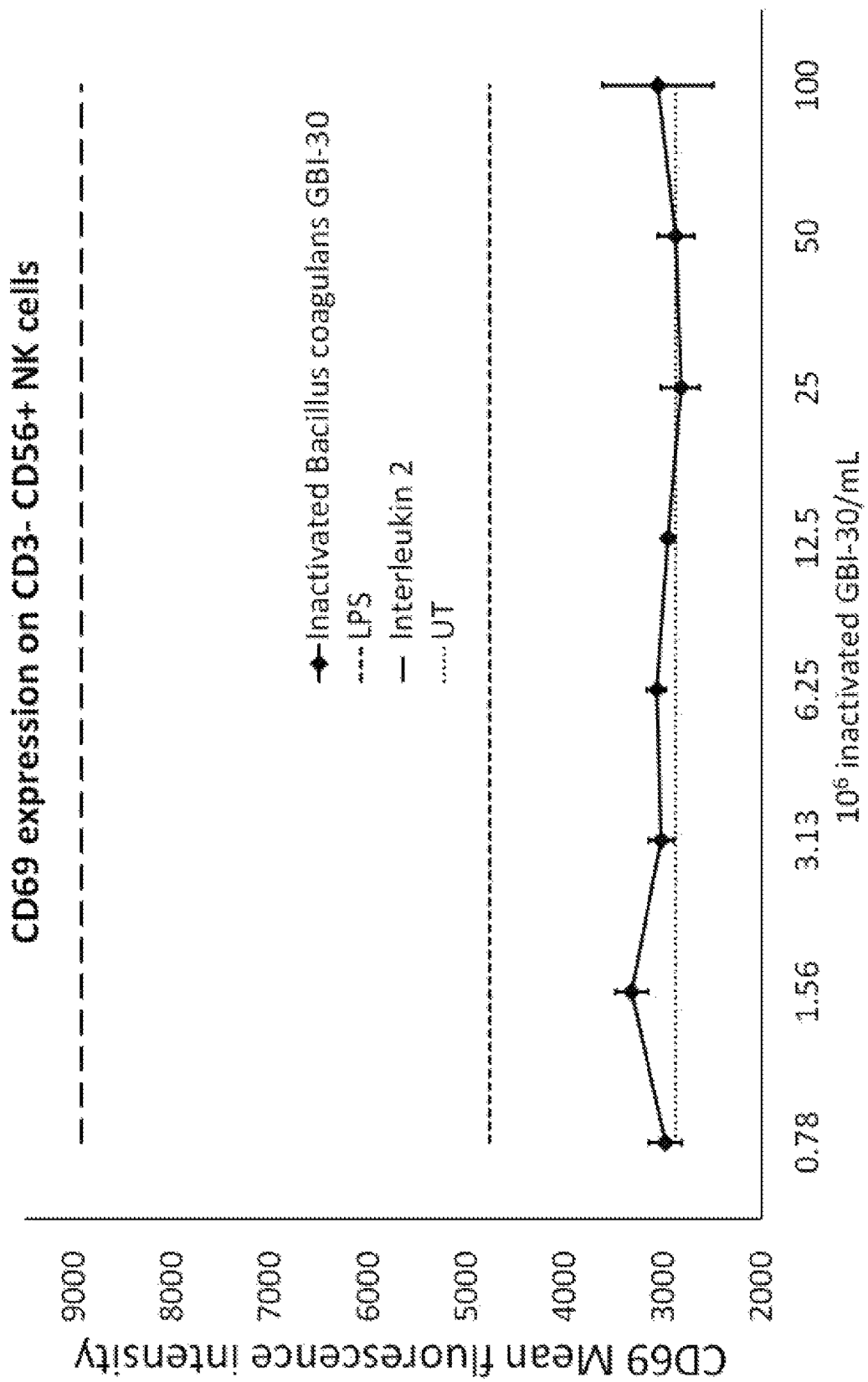
Figure 2D:
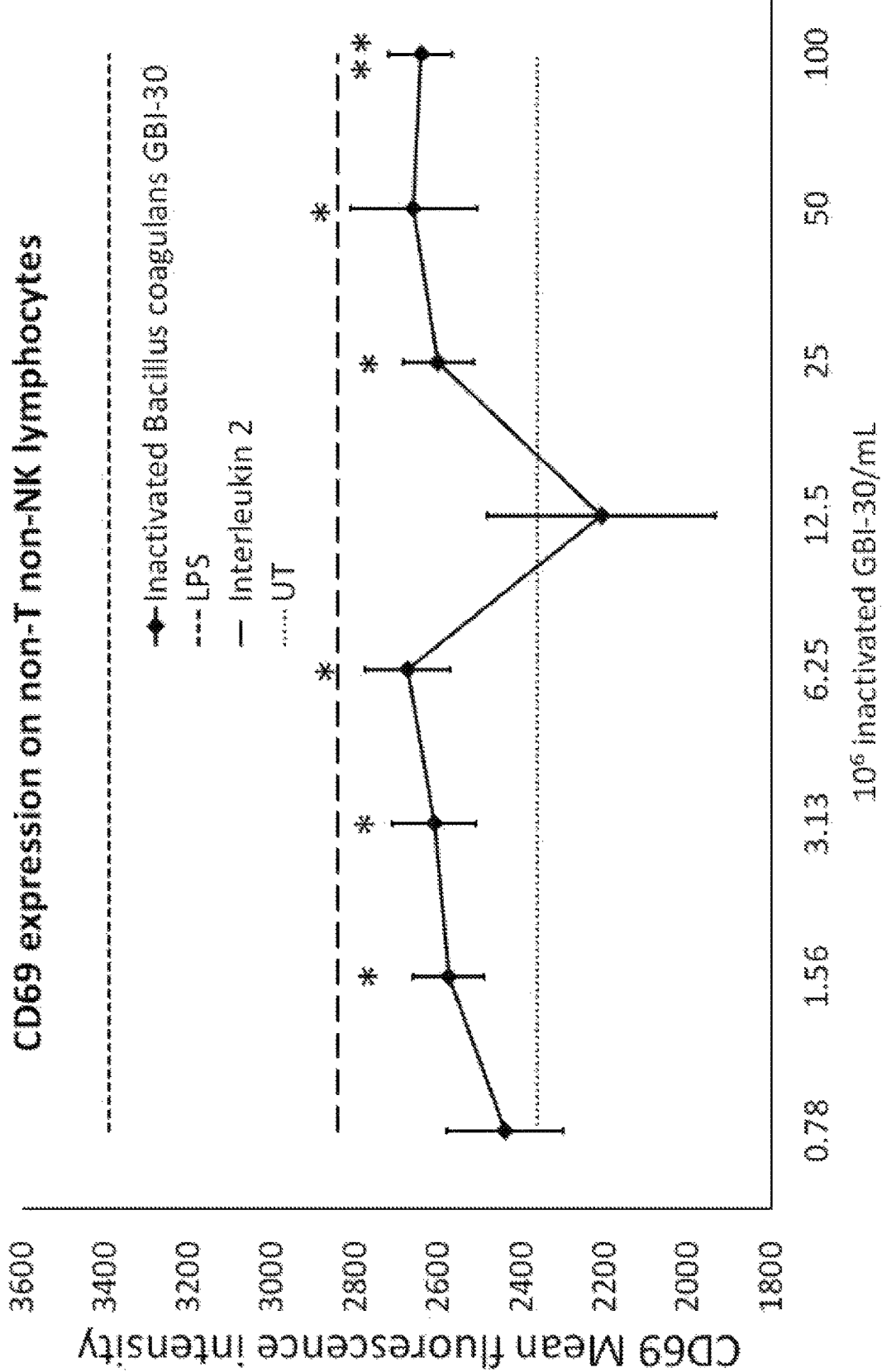
Figure 3A:
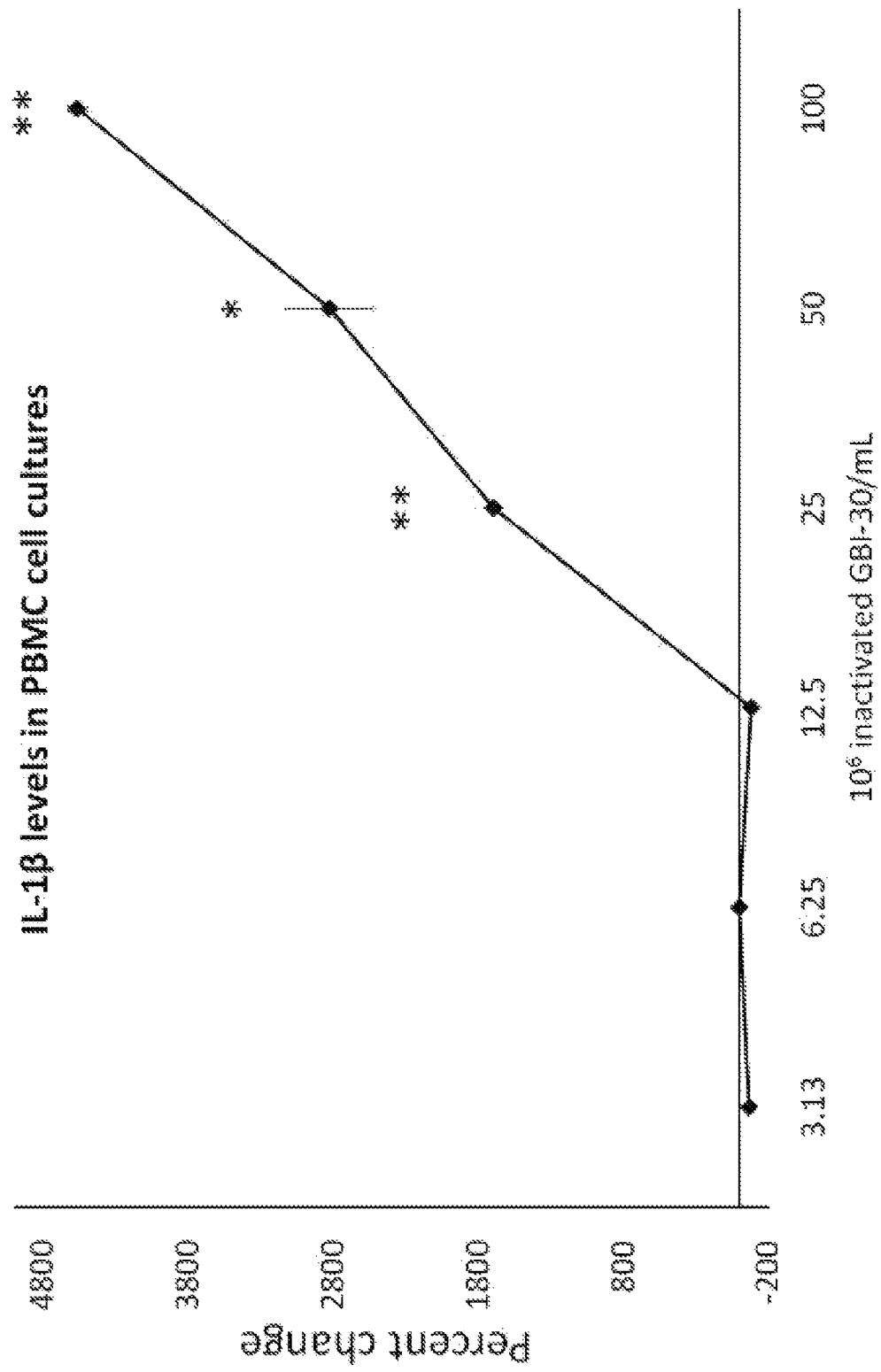
FIGS. 3A-D are graphs showing changes in proinflammatory cytokine levels in human PBMC cultures. Changes in cytokine levels in human PBMC cultures treated for 24 hours with serial dilutions of inactivated *Bacillus coagulans* GBI-30 are shown as percent change from untreated cell cultures. Mean fluorescence intensity for CD69 expression is shown. Data presented as mean±standard deviation from duplicate testing of culture supernatants from one of three separate experiments using PBMC cells from three different healthy human donors. Notes: *P<0.05; **P<0.01.
Figure 3B:
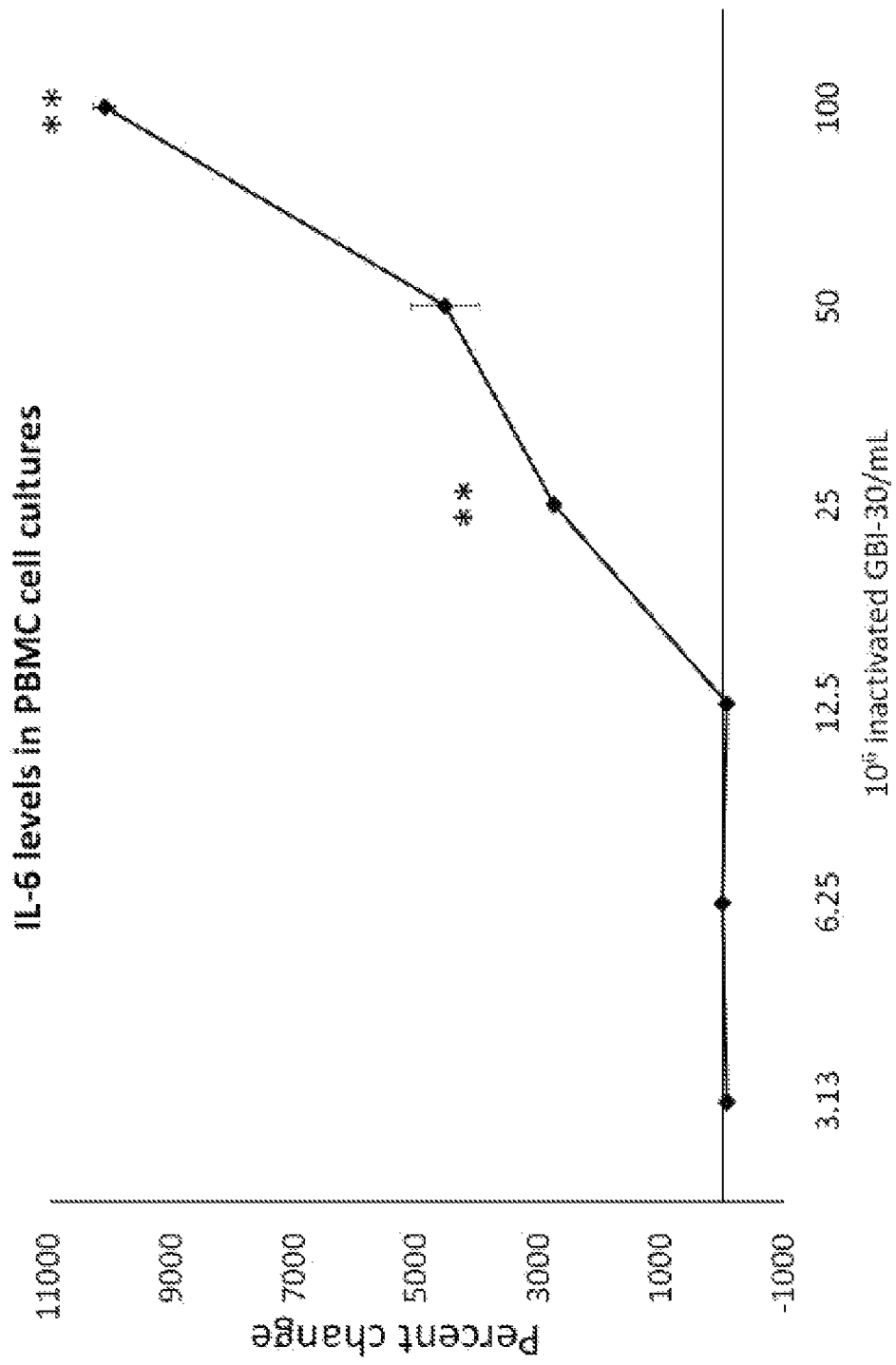
Figure 3C:
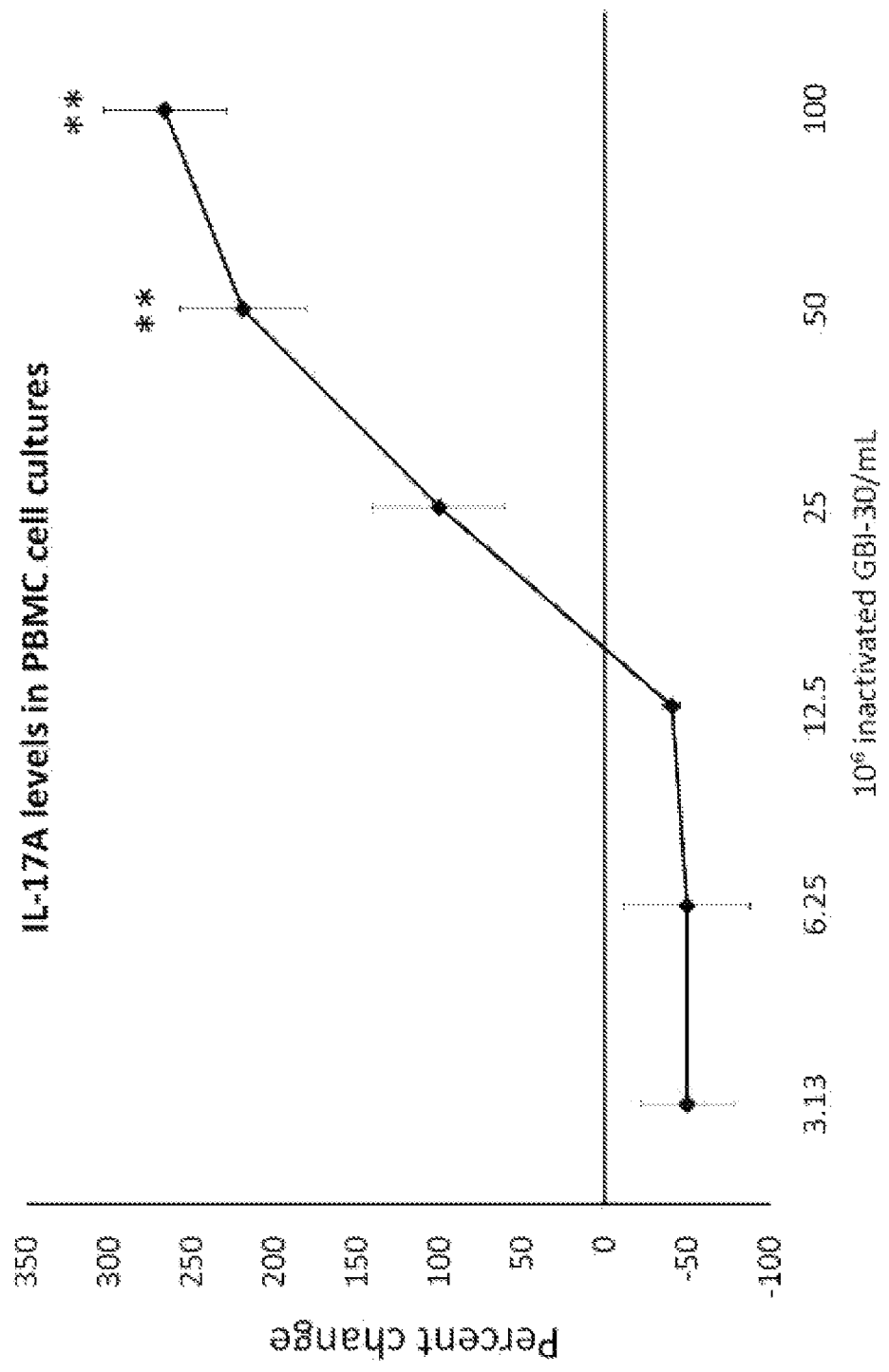
Figure 3D:
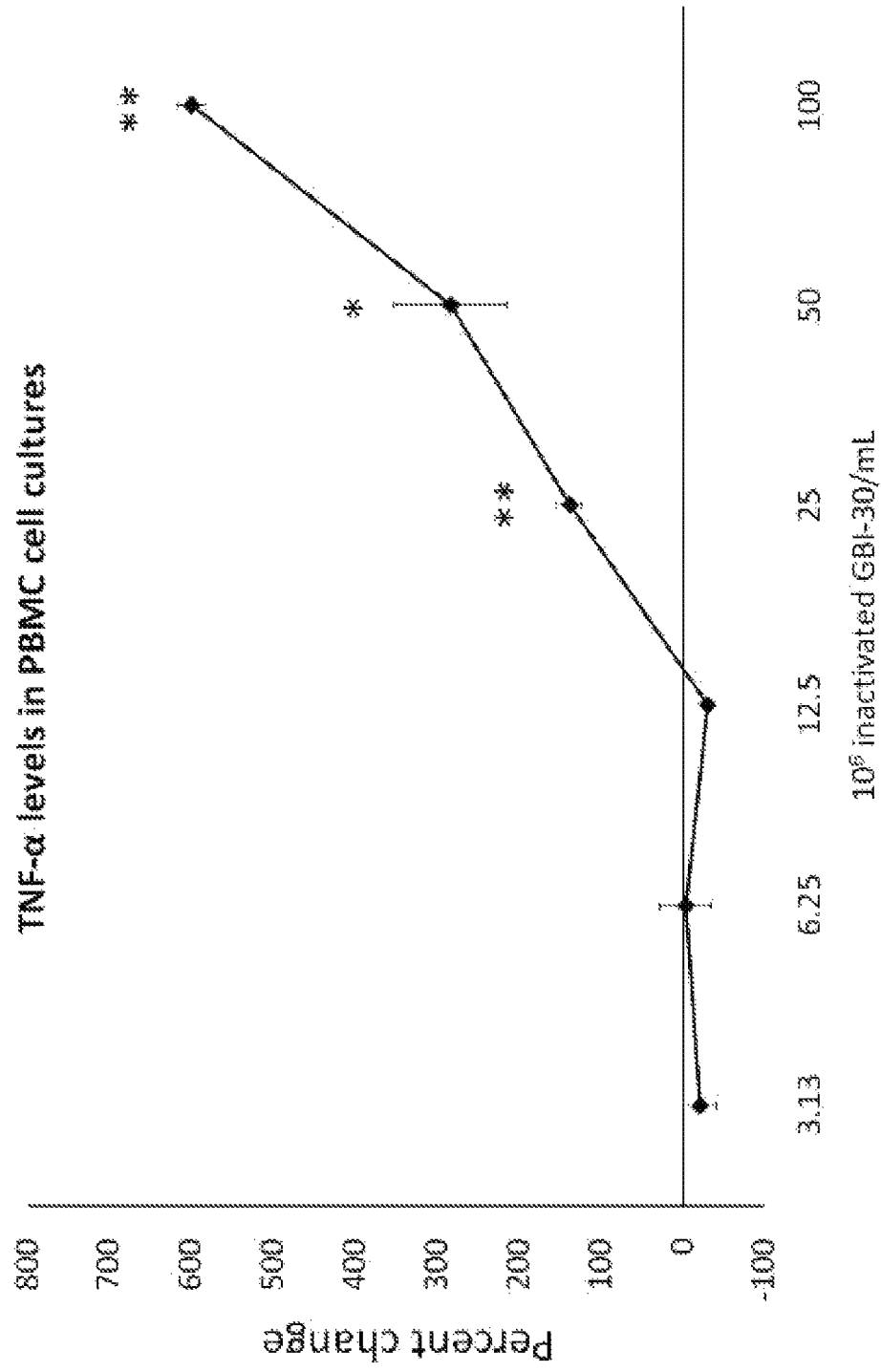
Figure 4A:
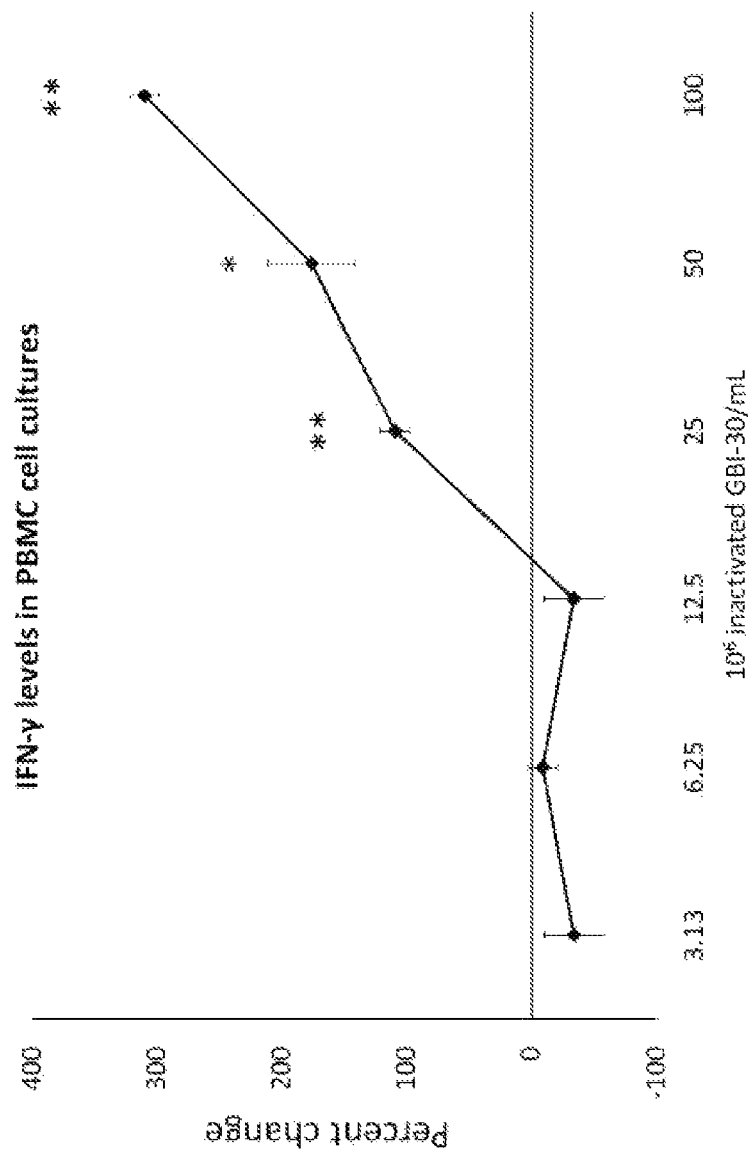
FIGS. 4A-D are graphs showing changes in levels of cytokines involved in anti-viral immunity in human PBMC cultures. Changes in cytokine levels in human PBMC cultures treated for 24 hours with serial dilutions of inactivated *Bacillus coagulans* GBI-30 are shown as percent change from untreated cell cultures. Mean fluorescence intensity for CD69 expression is shown. Data presented as mean±standard deviation from duplicate supernatants from one of three separate experiments using PBMC cells from three different healthy human donors. Notes: *P<0.05; **P<0.01.
Figure 4B:
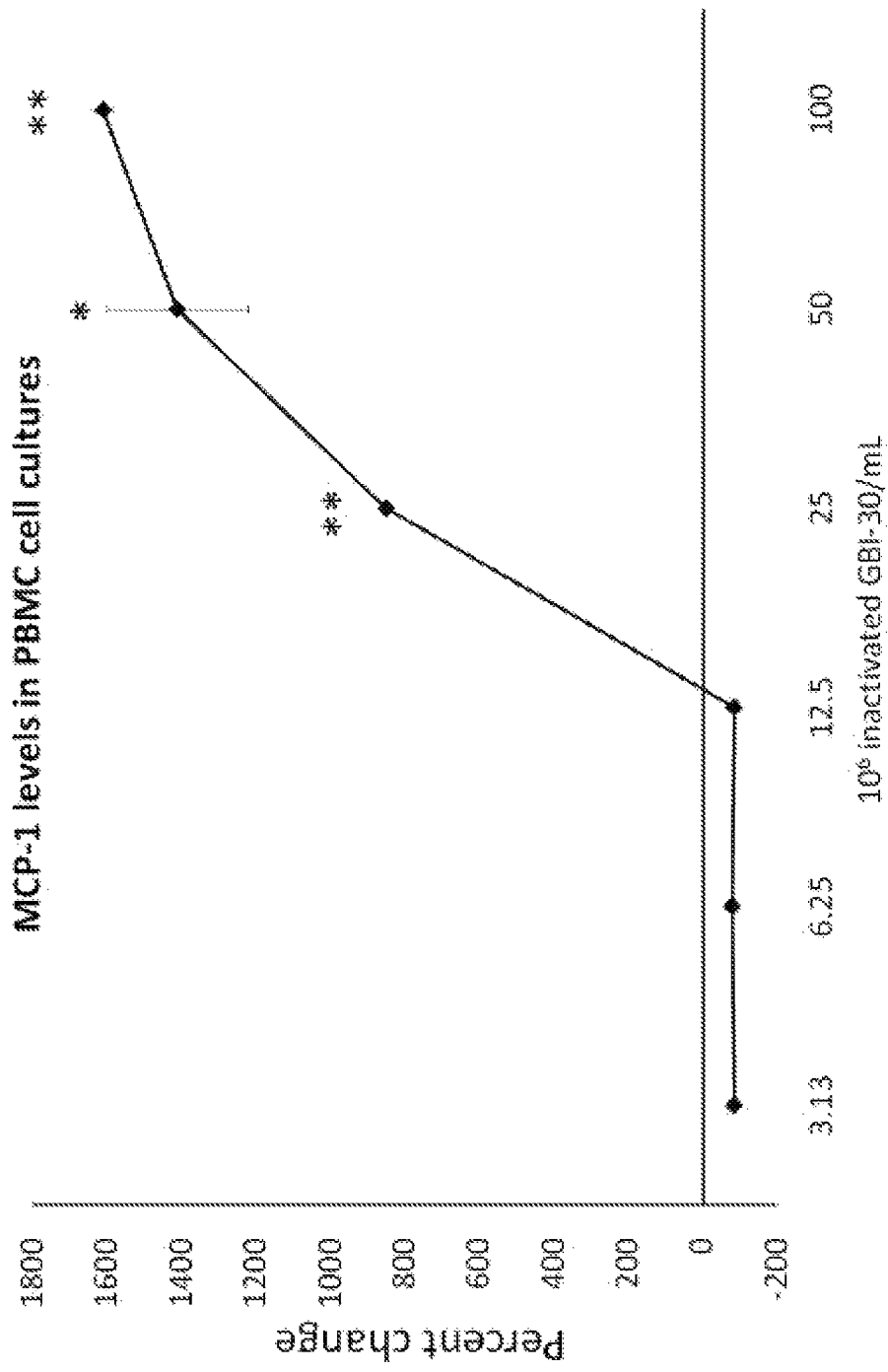
Figure 4C:
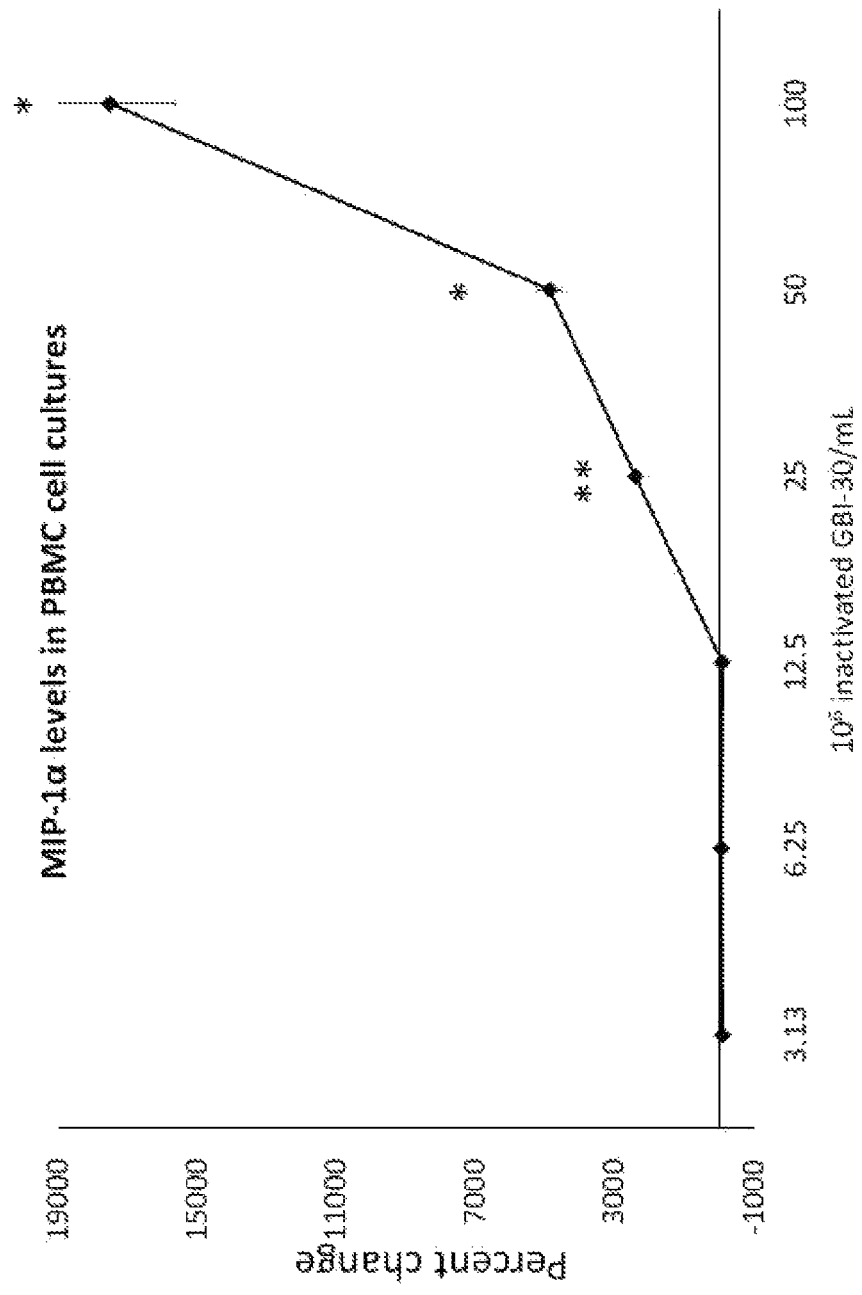
Figure 4D:
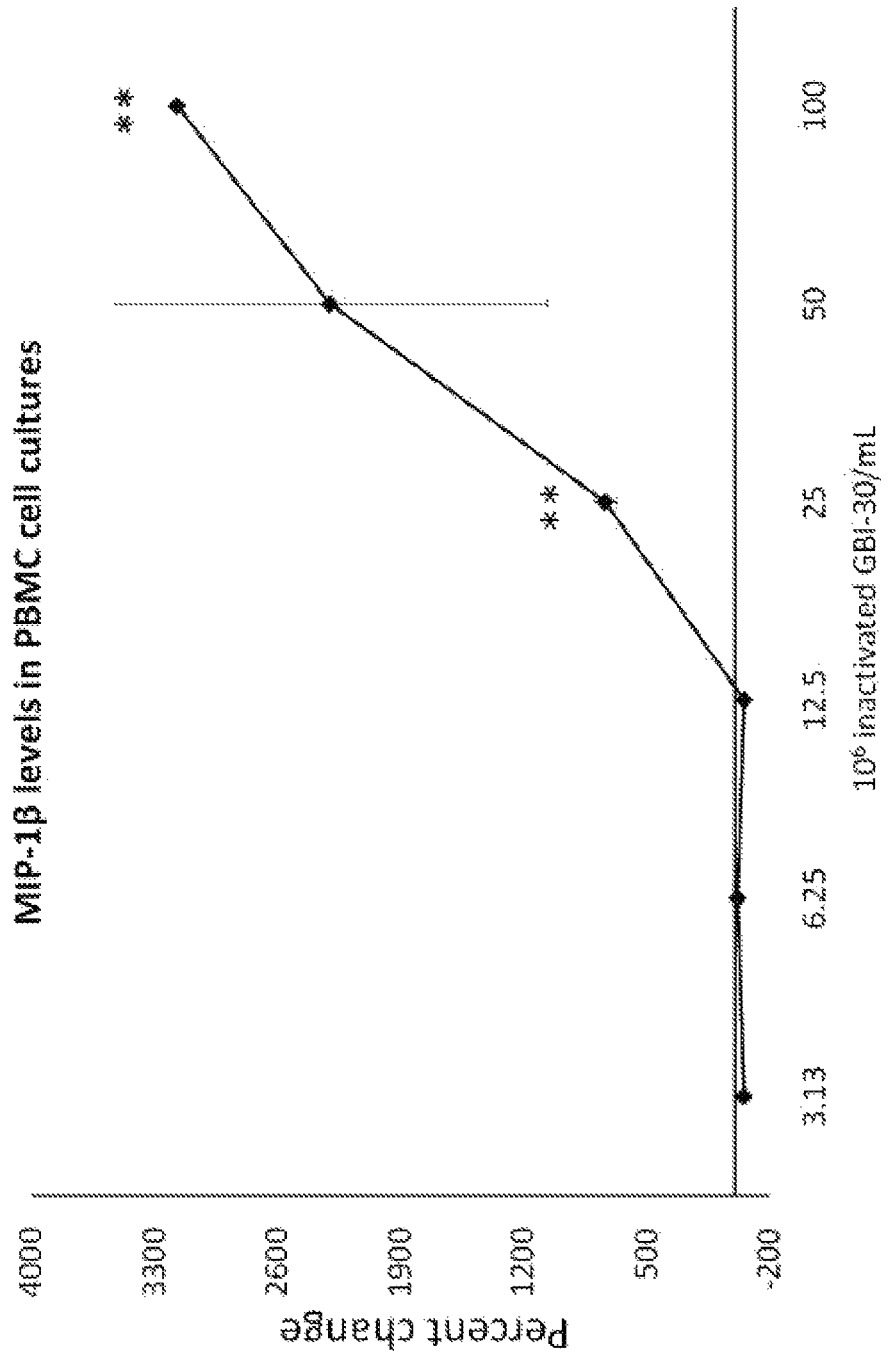

The use of fluorescently labeled antibodies to CD3, CD56, and CD69 allowed the monitoring of changes to lymphocyte subsets, including CD3+T lymphocytes, CD3+ CD56+ NKT cells, CD3-CD56+NK cells, and non-T non-NK lymphocytes. Treatment of PBMC cultures with GBI-30 for 24 hours led to activation of T lymphocytes, NKT cells, NK cells, and non-T non-NK cells (FIG. 2). T lymphocyte activation was seen across a broad dose range, and at the third-lowest dose ($3.13 \times 10^6$ bacteria/mL) the CD69 expression was as robust as for LPS-induced CD69 expression (FIG. 2A). The T lymphocyte activation remained highly significant even at the lowest dose of GBI-30. Activation of NKT cells was also observed across the entire dose range, and at some doses the activation was highly significant, compared to untreated control cultures (FIG. 2B). NK cell activation was most robust at the lower doses, and less prominent at higher doses (FIG. 2C). The CD69 expression in the non-T non-NK lymphocyte population was seen for a broad dose range as well, returning to baseline at the lowest dose tested (FIG. 2D). Lipopolysaccharide (LPS) was used as a positive control (10 ng/mL) and resulted in an increase in CD69 expression on all cell types. IL-2 (was used as a second positive control (100 IU/mL), and also showed an increase in CD69 on all cell types.

Occasionally, a large variation in CD69 expression was seen within one set of triplicate cultures, as reflected by large error bars, and in some cases, an average response in the triplicate set appears out of line with the overall dose response. Without being bound by any scientific theory, it is suggested that this is due to the nature of the test product, where the inactivated bacteria may clump within a culture well instead of dispersing, thus not providing optimal interaction between bacteria and PBMC cells within those wells. An example is the very low CD69 expression on non-T non-NK lymphocytes at the dose of $12.5 \times 10^6$ GBI-30/mL, where only one of the three triplicate culture wells showed the CD69 expression level comparable to the dose above and the dose below (FIG. 2D).

Immune-Activating Cytokines

Supernatants from the PBMC cultures exposed to inactivated *Bacillus coagulans* GBI-30 for 24 hours were simultaneously assayed for the levels of 27 different cytokines, chemokines, and growth factors, using a magnetic bead-based array and Luminex xMAP technology. Increases in the levels of cytokines with various immune activating and regulating properties were seen. This included robust upregulation of certain proinflammatory cytokines, including IL-1β, IL-6, IL-17, and TNF-α (FIG. 3). Increases were also seen for the cytokines IL-4, IL-7, IL-8, IL-9, and IL12p70 (data not shown). Furthermore, increases were seen for four biomarkers involved in anti-viral immune defense activity, namely Interferon-gamma (IFN-γ) and the three chemokines MCP-1, MIP1α, and MIP1β (FIG. 4).

Anti-Inflammatory Cytokines

Figure 5A:
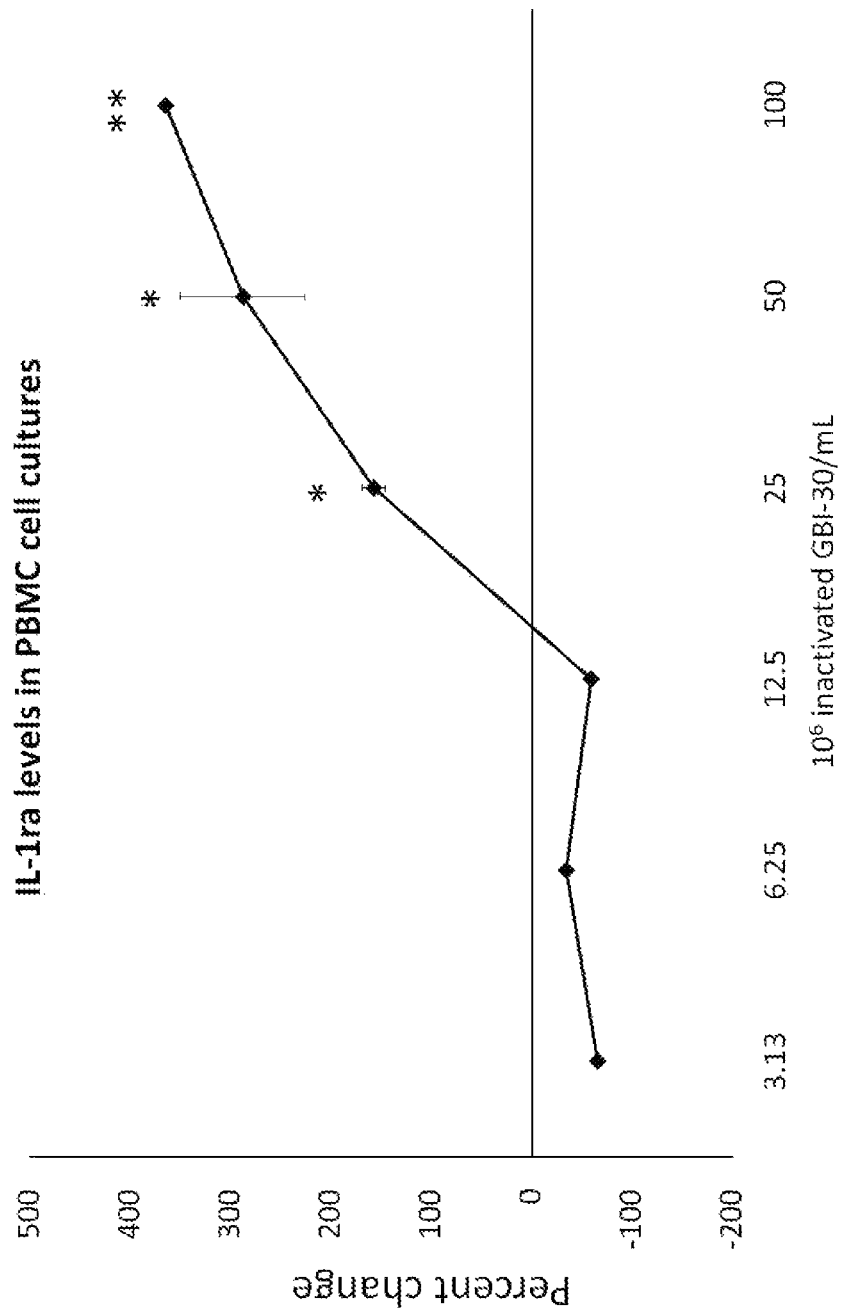
FIGS. 5A and B are graphs showing changes in anti-inflammatory cytokine levels in human PBMC cultures treated for 24 hours. Changes in cytokine levels in human PBMC cultures treated for 24 hours with serial dilutions of inactivated *Bacillus coagulans* GBI-30 are shown as percent change from untreated cell cultures. Mean fluorescence intensity for CD69 expression is shown. Data presented as mean±standard deviation from duplicate supernatants from one of three separate experiments using PBMC cells from three different healthy human donors. Notes: *P<0.05; **P<0.01.
Figure 6A:
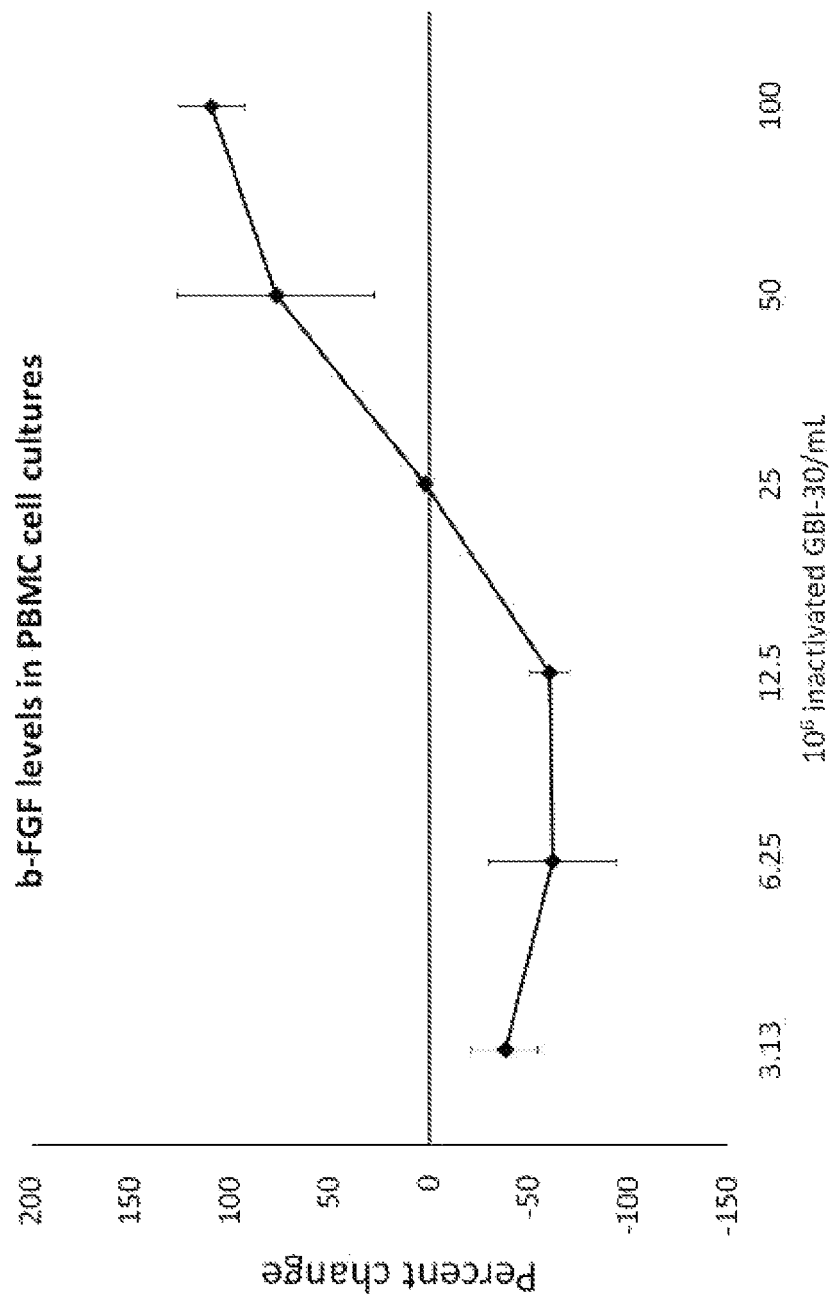
FIGS. 6A-D are graphs showing changes in growth factor levels in human PBMC cultures treated for 24 hours. Changes in growth factor levels in human PBMC cultures treated for 24 hours with serial dilutions of inactivated *Bacillus coagulans* GBI-30 are shown as percent change from untreated cell cultures. Mean fluorescence intensity for CD69 expression is shown. Data presented as mean±standard deviation from duplicate supernatants from one of three separate experiments using PBMC cells from three different healthy human donors. Notes: *P<0.05; **P<0.01.
Figure 6B:
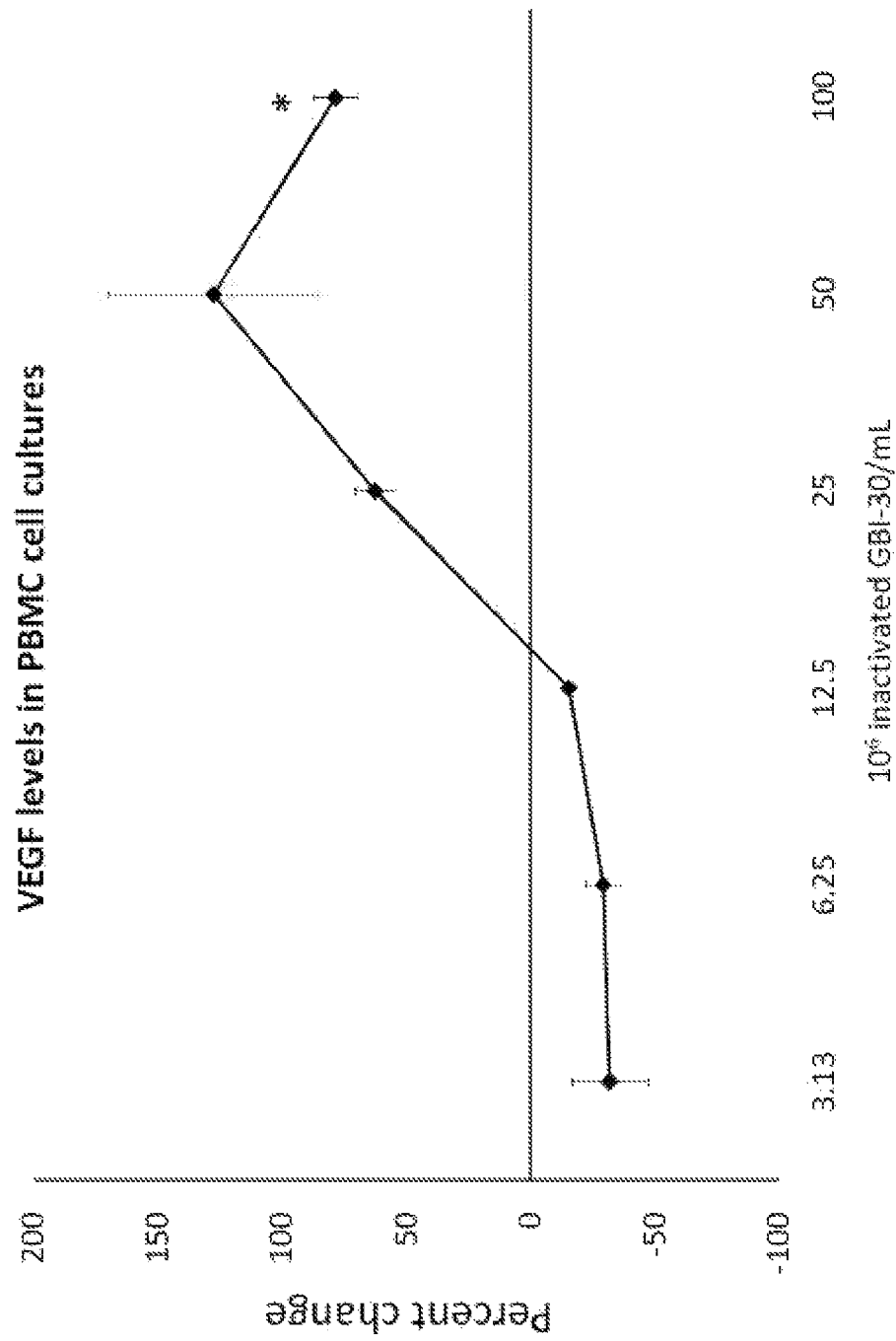
Figure 6C:
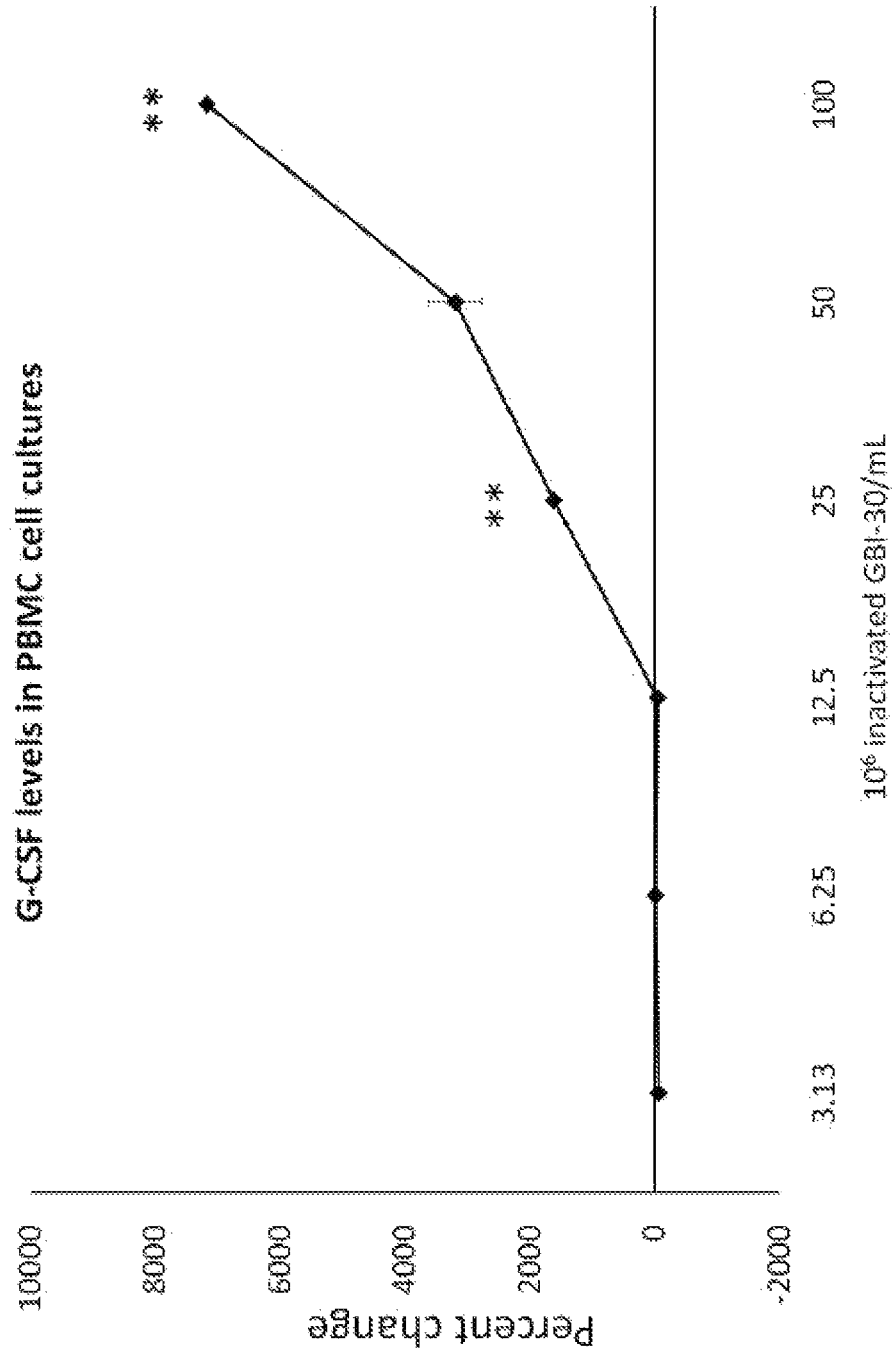
Figure 6D:
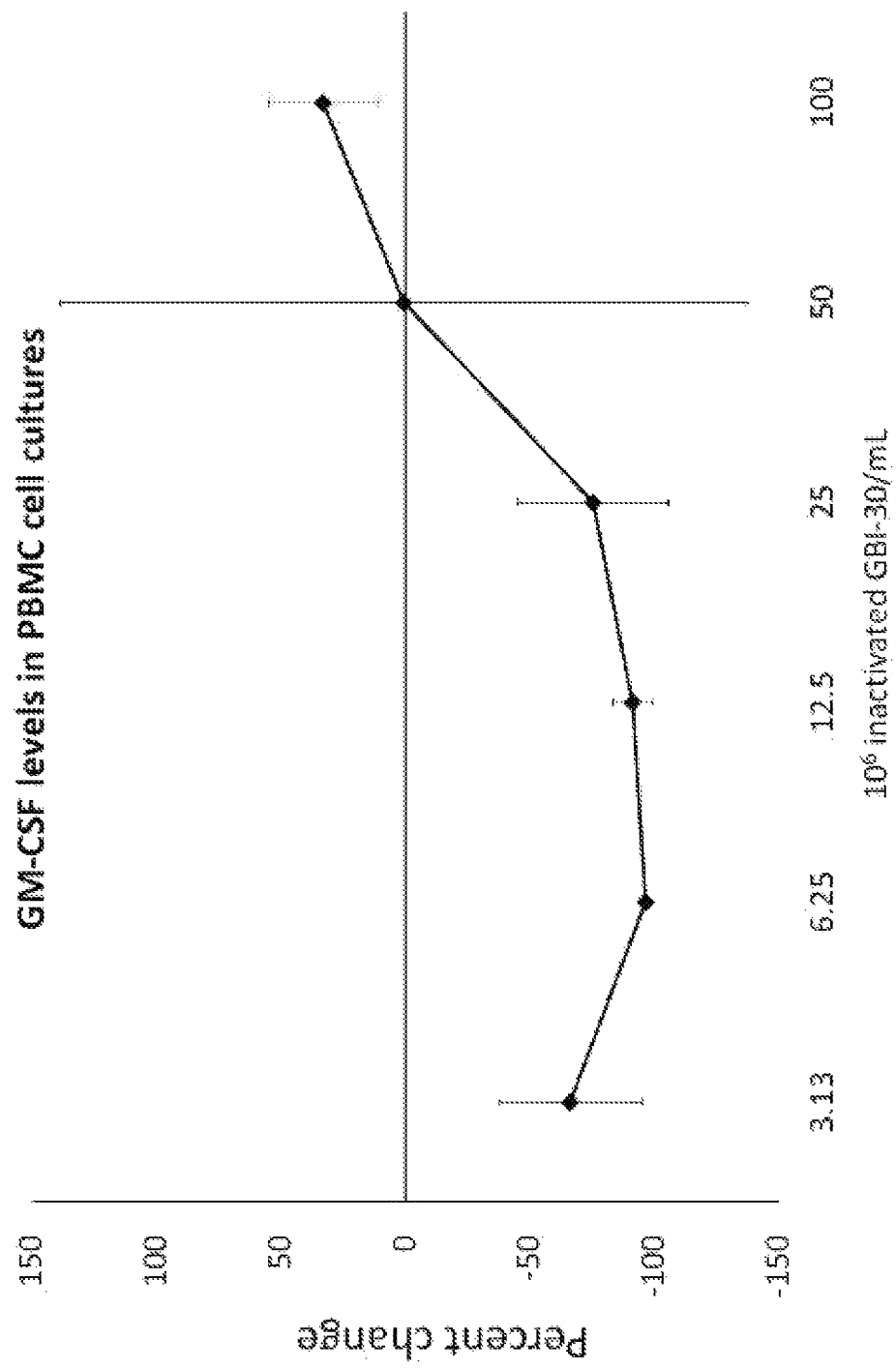

In parallel to increases in immune activating, pro-inflammatory cytokines, higher doses of the inactivated GBI-30 also triggered robust increases in the two anti-inflammatory cytokines IL-1ra and IL-10 (FIG. 5). The increases were comparable between the two anti-inflammatory cytokines, with an approximal 300-fold increase above the levels in untreated cell cultures.

Growth Factors

The exposure of human PBMC cells to inactivated GBI-30 triggered complex changes in growth factor production (FIG. 6). Bi-phasic dose responses were seen for the two growth factors basic Fibroblast Growth Factor (bFGF) and Vascular Endothelial Growth Factor (VEGF), known to play a role in cardiovascular health and wound healing (FIGS. 6A and 6B). Highly selective changes were seen for the growth factors Granulocyte-Colony Stimulating Factor (G-CSF)

and Granulocyte Macrophage-Colony Stimulating Factor (GM-CSF), both having differential effects on stem cell biology (FIGS. 6C and 6D), where treatment of PBMC with inactivated GBI-30 led to a very strong increase in G-CSF production, in contrast to a mild reduction in GM-CSF production.

Inactivated Probiotic *Bacillus coagulans* GBI-30 Induces Complex Immune Activating, Anti-Inflammatory, and Regenerative Markers In Vitro A goal for this study was to document the immune activating and anti-inflammatory effects of heat-inactivated probiotic strain *Bacillus coagulans* GBI-30 (ATCC Designation Number PTA-6086) (Staimune™) on human immune cells in vitro.

In vitro cultures of human peripheral blood mononuclear cells from healthy blood donors were treated with heat-inactivated GBI-30 for 24 hours. After incubation, the cells were stained with fluorochrome-labeled monoclonal antibodies for CD3, CD56, and CD69 to monitor cellular activation by flow cytometry. The culture supernatants were tested for cytokine profile using a 27-plex Luminex array, including pro- and anti-inflammatory cytokines, chemokines, and growth factors.

Inactivated GBI-30 induced the CD69 early activation marker on CD3+CD56− T lymphocytes, $CD3^+CD56^+$ NKT cells, $CD3^-CD56^+$ NK cells, and also some cells within the $CD3^-CD56^-$ non-T non-NK cell subset. Culture supernatants showed robust increases in the immune activating cytokines IL-1b, IL-6, IL-17A, and TNF-α. IFN-γ was increased, along with three chemokines MCP-1, MIP-1α and MIP-1β. The two anti-inflammatory cytokines IL-1ra and IL-10 were increased, as well as growth factors involved in repair and stem cell biology, namely VEGF, bFGF, and G-CSF. In contrast, GM-CSF levels showed a mild decrease, showing a highly selective growth factor response.

The inactivated GBI-30 activated human immune cells, altered the production of immune activating and anti-inflammatory cytokines and chemokines. Of special importance is the demonstration of a selective upregulation of growth factors involved in post-injury and post-inflammation repair and regeneration. This suggests that important immunogenic cell wall components, such as lipoteichoic acid, are undamaged after the heat-inactivation and retain the complex beneficial biological activities associated with live GBI-30 cell walls. The cell wall from *Bacillus coagulans* GBI-30 has complex biological properties, including both immune activating and anti-inflammatory properties.

Inactivated GBI-30 triggered an increase in the CD69 activation maker on multiple human immune cell types. CD69 is an early activation marker on many cell types, and is directly involved in the molecular apparatus responsible for NK cell-mediated killing of virus-infected and transformed cells (Moretta et al. J Exp Med. 1991 Dec. 1; 174(6):1393-8; Dons'koi et al. J Immunol Methods. 2011 Sep. 30; 372(1-2):187-95; Clausen et al. Immunobiology. 2003; 207(2):85-93). In addition, CD69 has broad range of functions, and also is important for T-cell/B-cell interactions, homing into appropriate tissue environments, and the process of generating and maintaining immunological memory (Schoenberger. Proc Natl Acad Sci USA. 2012 May 29; 109(22):8358-9; Cibrián and Sánchez-Madrid. CD69: from activation marker to metabolic gatekeeper. Eur J Immunol. 2017 May 5. doi: 10.1002/eji.201646837). The ability of inactivated GBI-30 to induce CD69 on multiple cell types indicates a broad effect involving cells from both the innate and the adaptive immune systems. Cell types in the non-T non-NK subset of cells, include dendritic cells, B lymphocytes, circulating hematopoietic, mesenchymal, and endothelial stem cells. Work on live GBI-30 showed that exposure of human mononuclear phagocytes triggered a favorable maturation of antigen-presenting cells toward both macrophage and dendritic cell phenotypes. This is important, since dendritic cells are first-line antigen-presenting cells in gut mucosal immune tissue, capable of unique surveillance activity and antigen recognition across intact epithelial barriers (Allen et al. Front Immunol. 2016 Jun. 10; 7:231), and therefore represents the initial cell type that encounters consumed GBI-30 in vivo.

Inactivated GBI-30 triggered robust increases in the production of multiple cytokines, chemokines, and growth factors. The current data spans a broader range of cytokines, chemokines, and growth factors than previously tested for live GBI-30. This has helped confirm the potent immune activating properties of GBI-30. It also demonstrated biological properties associated with anti-viral and regenerative functions. The increases in the biomarkers IFNγ, MCP-1, MIP-1α, and MIP-1β, involved in antiviral immune defense mechanisms and cellular recruitment, is of special importance. IFNγ has direct anti-viral properties, activates macrophages, and enhances NK cell killing activity of transformed cells. The three chemokines facilitate recruitment of immune cells to sites of inflammation, whether caused by injury or infection. The increase in two anti-inflammatory cytokines IL-1ra and IL-10 points to the complexity of inactivated GBI-30 immune modulation. Without being bound by any scientific theory, this effect represents a later part of the cascade triggered to resolve the initial pro-inflammatory immune activation, and limit the inflammatory process in space and time.

Several growth factors known to play specific roles in endogenous regeneration were upregulated in the cultures of human mononuclear cells. Two growth factors VEGF and bFGF were upregulated in immune cells treated with inactivated GBI-30, and are inducers of neovascularization, also known as angiogenesis. Normal functions for VEGF and bFGF involve crucial mechanisms of repair and formation of new blood vessels and muscle after injury and exercise, in part via mesenchymal stem cells (Supanc et al. J Tissue Eng Regen Med. 2017 Jan. 12). This is an important function in the process of recovery from trauma, such as muscle injury, traumatic brain injury, and stroke. In addition, highly selective, contrasting effects were seen for the two stem cell growth factors, namely G-CSF and GM-CSF. Inactivated GBI-30-treated PBMC cultures showed a robust increase in G-CSF levels, reaching over 7000-fold above untreated cultures at the highest dose of GBI-30, in contrast to mildly reduced GM-CSF levels. This is an important differentiation, since G-CSF supports stem cells to produce neutrophils, whereas GM-CSF promotes production of more cell types, including eosinophils, involved in immune defense against multi-cellular parasites and also involved in inflammation in allergies and asthma. In addition, VEGF, FGF, and G-CSF is used therapeutically to support stem cell mobilization, migration, and tissue repair (Chan et al. Neurochem Int. 2017 Apr. 12. pii: S0197-0186(16)30432-6). Therefore, the selective effect of GBI-30 on growth factor production may be directly beneficial in repair and regeneration of the gut mucosal tissue, for example in situations of ulceration, as well as systemically, via effects on many cell types, including inflammation-modulating mesenchymal stem cells (Lee et al. J Dent Res. 2016 October; 95(11):1274-81; Sica and Mantovani. J Clin Invest. 2012 March; 122(3):787-95). Mesenchymal stem cells are able to sense signals from, and migrate into injured, inflamed, and ischemic tissue.

They can cross the blood-brain barrier, and contribute to repair of brain injuries such as stroke. Interestingly, it has been shown that treatment of mesenchymal stem cells from healthy human donors with IL-1, TNF-α, and IFN-γ production contributed to a strong increase in G-CSF production by the mesenchymal stem cells (Redondo-Castro et al. Stem Cell Res Ther. 2017 Apr. 17; 8(1):79); and subsequently, the increase in G-CSF re-programmed LPS-activated microglial cells to secrete fewer inflammatory mediators. This sequential process may apply to events when mononuclear cells, which include various types of stem cells, are exposed to inactivated GBI-30, and may suggest a cascade of events where an initial immune activating signal upregulated production of pro-inflammatory cytokines, followed by anti-inflammatory processes intended to resolve the inflammation, combined with reparative growth factors.

Without being bound by any scientific theory, three observations from the current work reported here are of key importance in validation of similar biological activities of the inactivated, heat-treated GBI-30, compared to the immune modulating properties of non-heated cell wall fractions from living *Bacillus coagulans* BC-30: (1) Both are capable of increasing the CD69 activation marker on lymphocytes, (2) both are able to increase production of the pro-inflammatory cytokine IL-6, and (3) both are capable of increasing the anti-inflammatory cytokine IL-10. This suggest that cell wall components, including lipoteichoic acid, has remained at least partially preserved by the inactivation process.

A direct dose comparison to the previous in vitro work is not feasible. Previous work on the cell wall's immune activating properties was performed on material that went through repeated freeze/thaw and bead-milling cycles, thus breaking down the cell walls into small fractions, each capable of engaging appropriate receptors on the surface of the PBMC cells. In contrast, the current work involved the addition of intact bacteria to the cell cultures.

The complex effects of GBI-30 suggest possible multi-facetted clinical responses after consumption, involving immune activation, anti-inflammatory effects, and effects involving stem cell mobilization, homing, and re-programming involved in accelerated repair. The direct effects of GBI-30 are expected to translate to immune activation at the level of the gut mucosa, and trigger rapid systemic effects. This is different from a study on the live *Bacillus coagulans* where ingested spores will give rise to living bacteria that can colonize the intestinal tract, and where an important part of the biological effects is due to secreted bacterial metabolites. Future work on inactivated GBI-30 should include a human clinical study to examine acute effects, using the study design previously published by our team on efficacious immune modulating natural products (Jensen et al. J Med Food. 2011 September; 14(9):1002-10; Jensen et al. Prev Med. 2012 May; 54 Suppl:S124-9), as well as nutraceutical products that have effects on human stem cell biology (Jensen et al. Cardiovasc Revasc Med. 2007 July-September; 8(3):189-202; Drapeau et al. J Stem Cell Res Ther 2015, 5:287).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of increasing physical performance in a subject, the method comprising:
    administering an effective amount of a composition comprising inactivated, non-viable, or dead *Bacillus coagulans* bacteria to the subject to increase the physical performance in the subject,
    wherein the inactivated, non-viable, or dead *Bacillus coagulans* bacteria comprise inactivated, non-viable, or dead *Bacillus coagulans* spores,
    wherein the composition is a food or beverage, and
    wherein the composition is administered during an exercise period of the subject, within 60 minutes before the exercise period of the subject, and/or within 60 minutes after the exercise period of the subject.

2. The method of claim 1, wherein bacteria comprises at least 85% *Bacillus coagulans* spores.

3. The method of claim 1, wherein the inactivated, non-viable, or dead *Bacillus coagulans* bacteria further comprise inactivated, non-viable, or dead *Bacillus coagulans* vegetative bacteria.

4. The method of claim 1, wherein the bacteria are *Bacillus coagulans* GBI-30 (ATCC Designation No. PTA-6086), bacteria.

5. The method of claim 1, wherein increasing the physical performance in the subject comprises reducing muscle soreness, increasing physical strength or endurance, decreasing post-exercise recovery time, increasing muscle mass, increasing lean muscle development, recovery, strength, or repair in the subject.

6. The method of claim 1, wherein increasing the physical performance in the subject comprises reducing muscle soreness, and wherein the muscle soreness is post-exercise muscle soreness.

7. A method of increasing physical performance in a subject, the method comprising:
    administering an effective amount of a composition comprising inactivated, non-viable, or dead *Bacillus coagulans* bacteria to the subject to increase the physical performance in the subject, wherein the inactivated, non-viable, or dead *Bacillus coagulans* bacteria comprise inactivated, non-viable, or dead *Bacillus coagulans* spores,
    wherein the composition is a food or beverage composition,
    wherein the effective amount is effective to reduce inflammation in the subject,
    wherein the subject has an injury or arthritis, or has had a stroke, and
    wherein the composition is administered during an exercise period of the subject, within 60 minutes before the exercise period of the subject, and/or within 60 minutes after the exercise period of the subject.

8. The method of claim 1, wherein the subject does not have a respiratory, mucous membrane, skin, or gastrointestinal infection.

9. The method of claim 1, wherein the effective amount is effective to reduce inflammation in the subject, increase the level of at least one growth factor in a subject, increase the level of granulocyte colony-stimulating factor (G-CSF) or granulocyte macrophage colony-stimulating factor (GM-CSF) in the subject, increase the level of interleukin-1 receptor antagonist (IL1RA), interleukin-6 (IL-6), or interleukin-10 (IL-10) in the subject, increase the level of at least one immune activating cytokine in the subject, and/or increase the level of at least one immune activating chemokine in the subject.

10. The method of claim 9, wherein the level is the level of the at least one growth factor in a bodily fluid of the subject.

11. The method of claim 10, wherein the bodily fluid is blood, plasma, or serum.

12. The method of claim 9, wherein the growth factor increases tissue repair, stem cell differentiation, or stem cell proliferation.

13. The method of claim 9, wherein the at least one immune activating cytokine comprises interleukin-1 beta (IL-1β), interleukin-6 (IL-6), interleukin-17A (IL-17A), Tumor Necrosis Factor-α (TNF-α), or interferon gamma (IFNγ).

14. The method of claim 9, wherein the at least one immune activating chemokine comprises monocyte chemoattractant protein-1 (MCP-1), macrophage inflammatory protein 1-alpha (MIP-1α), or macrophage inflammatory protein-1β (MIP1β).

15. The method of claim 1, wherein the composition is less than about 0.001% water by weight.

16. The method of claim 1, wherein the composition further comprises an excipient.

17. The method of claim 1, wherein the composition further comprises a β-glucan, maltodextrin, inulin, initosol, trehalose, micro-crystalline cellulose (MCC), calcium lactate, magnesium stearate, fructo-oligosaccharide (FOS), or gluco-oligosaccharide (GOS).

18. The method of claim 1, wherein the inactivated, non-viable, or dead *Bacillus coagulans* bacteria are lyophilized.

19. The method of claim 1, wherein the inactivated, non-viable, or dead *Bacillus coagulans* bacteria have been lyophilized and then combined with an aqueous solution.

20. The method of claim 1, wherein the composition further comprises a surfactant or an emulsifier.

21. The method of claim 1, wherein the food or beverage composition comprises:
    (a) tea, coffee, or an alcoholic beverage;
    (b) a fermented food or beverage;
    (c) a grain-based composition;
    (d) a baked composition;
    (e) a confection;
    (f) an omega-3 fatty acid;
    (g) a dairy composition;
    (h) a non-dairy milk-like composition;

(i) a sports nutrition composition; or
(j) feed for a work animal, a companion animal, livestock, or aquaculture.

22. The method of claim 1, wherein the composition is administered during an exercise period of the subject.

23. The method of claim 1, wherein the composition is administered within 60 minutes before or after the exercise period of the subject.

* * * * *